(12) United States Patent
Herder et al.

(10) Patent No.: US 8,567,394 B2
(45) Date of Patent: Oct. 29, 2013

(54) INHALATION DEVICE FOR DRUGS IN POWDER FORM

(75) Inventors: Martin Herder, Rodgau (DE); Gerhard Ludanek, Nidderau (DE); Ingo Mett, Frankfurt (DE)

(73) Assignee: Almirall, S.A., Barcelona (ES)

( * ) Notice: Subject to any disclaimer, the term of this patent is extended or adjusted under 35 U.S.C. 154(b) by 1074 days.

(21) Appl. No.: 12/520,252

(22) PCT Filed: Dec. 21, 2007

(86) PCT No.: PCT/EP2007/011372
§ 371 (c)(1),
(2), (4) Date: Aug. 11, 2009

(87) PCT Pub. No.: WO2008/077623
PCT Pub. Date: Jul. 3, 2008

(65) Prior Publication Data
US 2010/0012120 A1 Jan. 21, 2010

(30) Foreign Application Priority Data
Dec. 22, 2006 (DE) .................. 10 2006 062 196

(51) Int. Cl.
*A61M 15/00* (2006.01)
*A61M 16/00* (2006.01)

(52) U.S. Cl.
USPC ............................... 128/203.19; 128/203.15

(58) Field of Classification Search
USPC ............. 128/203.12, 203.15, 203.19, 203.21, 128/203.23, 205.24
See application file for complete search history.

(56) References Cited

U.S. PATENT DOCUMENTS

| | | | |
|---|---|---|---|
| 2,470,297 A | 5/1949 | Fields |
| 2,587,215 A | 2/1952 | Priestly |
| 4,274,403 A | 6/1981 | Struve |
| 5,033,463 A | 7/1991 | Cocozza |
| 5,113,855 A | 5/1992 | Newhouse |

(Continued)

FOREIGN PATENT DOCUMENTS

| | | |
|---|---|---|
| CA | 2093809 A1 | 2/1993 |
| CA | 2090227 C | 11/2004 |

(Continued)

OTHER PUBLICATIONS

International Preliminary Report on Patentability mailed Jul. 2, 2009 in priority International Application No. PCT/EP2007/011372.

(Continued)

*Primary Examiner* — Jackie Ho
*Assistant Examiner* — Peter S Vasat
(74) *Attorney, Agent, or Firm* — Faegre Baker Daniels LLP

(57) ABSTRACT

To provide an inhalation device which has improved use properties, particularly advanced moisture protection while in use, an inhalation device (1) for powder drugs is proposed comprising at least one storage chamber (13) for accommodating a plurality of drug powder doses and a dosing device which includes at least one dosing slider (15) which is movable approximately with a translatory movement in a dosing slider passage (16) at least from a filling position into an emptying position, wherein the inhalation device (1) further includes a device for inhalation-triggered automatic movement of the dosing slider (15) from its filling position into the emptying position and a return device for automatic movement of the dosing slider (15) back into the filling position.

51 Claims, 29 Drawing Sheets

(56) References Cited

U.S. PATENT DOCUMENTS

| | | |
|---|---|---|
| 5,239,992 A | 8/1993 | Bougamont et al. |
| 5,301,666 A | 4/1994 | Lerk et al. |
| 5,320,714 A | 6/1994 | Brendel |
| 5,435,301 A | 7/1995 | Herold et al. |
| 5,505,196 A | 4/1996 | Herold et al. |
| 5,840,279 A | 11/1998 | Narodylo et al. |
| 5,881,719 A | 3/1999 | Gottenauer et al. |
| 6,029,661 A | 2/2000 | Whaley et al. |
| 6,071,498 A | 6/2000 | Narodylo et al. |
| 6,182,655 B1 | 2/2001 | Keller et al. |
| 6,209,538 B1 | 4/2001 | Casper |
| 6,718,972 B2 | 4/2004 | O'Leary |
| 6,752,147 B1 | 6/2004 | Goldemann et al. |
| 7,131,441 B1 * | 11/2006 | Keller et al. ............. 128/203.15 |
| 7,258,118 B2 | 8/2007 | Goede et al. |
| 2003/0136405 A1 | 7/2003 | Goede et al. |

FOREIGN PATENT DOCUMENTS

| | | |
|---|---|---|
| DE | 846770 C | 8/1952 |
| DE | 3535561 A1 | 5/1986 |
| DE | 3901963 C1 | 8/1990 |
| DE | 4400083 A1 | 7/1995 |
| DE | 4400084 A1 | 7/1995 |
| DE | 19523516 C1 | 10/1996 |
| DE | 19522415 A1 | 1/1997 |
| DE | 19522416 A1 | 1/1997 |
| DE | 19825434 A1 | 8/1999 |
| DE | 10202940 A1 | 7/2003 |
| EP | 0416950 A1 | 3/1991 |
| EP | 0416951 A1 | 3/1991 |
| EP | 0640354 A2 | 3/1995 |
| EP | 0865302 A1 | 9/1998 |
| EP | 1051212 A1 | 11/2000 |
| EP | 1386630 A1 | 2/2004 |
| EP | 1616592 A1 | 1/2006 |
| FR | 2701653 A1 | 8/1994 |
| GB | 2165159 A | 4/1986 |
| WO | WO92/00771 A1 | 1/1992 |
| WO | WO92/09322 A1 | 6/1992 |
| WO | WO93/03782 A1 | 3/1993 |
| WO | WO9311773 A1 | 6/1993 |
| WO | WO93/16748 A2 | 9/1993 |
| WO | WO93/24167 A1 | 12/1993 |
| WO | WO95/31237 A1 | 11/1995 |
| WO | WO99/09092 A1 | 2/1999 |
| WO | WO99/47199 A1 | 9/1999 |
| WO | WO00/74754 A2 | 12/2000 |

OTHER PUBLICATIONS

Canadian Office Action mailed May 2, 2013 in related Canadian application No. 2673553.

* cited by examiner

A

B

C

INHALATION DEVICE FOR DRUGS IN POWDER FORM

The invention concerns an inhalation device for drugs in powder form comprising at least one storage chamber for accommodating a plurality of drug powder doses and a dosing device which includes at least one dosing slider which is movable approximately with a translatory movement in a dosing slider passage at least from a filling position into an emptying position.

BACKGROUND OF THE INVENTION

In the field of treating bronchial diseases but also other diseases in which medication can be effected by way of the respiratory tract, it is known to apply medicaments in powder form, besides the atomisation of solutions or suspensions to afford inhalable aerosols. Many different examples of such medicaments are described in the literature, purely by way of example we refer to WO 93/11773, EP 0 416 950 A1 and EP 0 416 951 A1. A usual form of application in that respect is a supply by way of an inhalation device or inhaler.

In the case of inhalers for powder drugs, such inhalers are known both for the application of an individual dose, and also inhalation devices which have a store for a multiplicity of drug doses. In regard to the latter it is known either to provide separate storage chambers for a respective individual dose or an individual receiving chamber for accommodating a plurality of doses of a medicament.

In the case of inhalers which have a plurality of individual doses in separate storage chambers, those are known in which individual chambers of the inhaler are respectively filled with a drug dose. An example of such an inhaler is described in U.S. Pat. No. 5,301,666 A. It is however also known for a plurality of drug powder doses to be respectively separately disposed in the spaces or chambers of so-called blister packs. An example of such a blister pack for use with an inhaler is described in DE 44 00 083 C2. Such a blister pack which at the same time is in the form of a disposable inhaler is described for example in DE 44 00 084 A1.

An inhalation device into which blister packs can be fitted which include respective separate storage chambers for individual doses of a powder drug and which can be emptied successively by means of the inhalation device is described for example in DE 195 23 516 C1.

Many different examples of inhalers with a storage chamber for a plurality of drug doses are described in the state of the art. An example with a replaceable storage container is described in German patent specification 846 770, and another one is described in WO 95/31237.

A serious problem in inhalation systems in which a plurality of doses of a medically effective substance is disposed in a common storage chamber is apportioning an individual dose for an individual inhalation operation. A large number of proposed solutions have been set forth in that respect as described for example in U.S. Pat. Nos. 2,587,215 A and 4,274,403 A. Other forms of arrangements for dosing an individual drug powder dose from a storage chamber for a plurality of drug doses are also described in WO 92/09322, WO 93/16748, WO 93/03785, U.S. Pat. No. 6,029,661 A and DE 35 35 561 C2 as well as GB 2 165 159 A. An interchangeable cartridge for accommodating a plurality of doses of a drug powder with an integrated dosing slider is known from DE 195 22 415 A1.

A further serious problem in the inhalation of drug powder is the breakdown of the galenic powder formulations into particles which can reach the lungs. The active substances administered in that way are generally brought together with carrier substances in order to achieve reasonable dosability of the medically active substance and in order to set further properties of the drug powder which for example can involve storage capability.

Approaches involving the design configurations of powder inhalers which are intended to provide for the provision of particles which are capable of reaching the lungs in an air flow are described for example in EP 0 640 354 A2, U.S. Pat. Nos. 5,505,196 A, 5,320,714 A, 5,435,301 A, 5,301,666 A, DE 195 22 416 A1 and WO 97/00703. In that respect proposals are also known for using auxiliary energy for producing the airflow, for example from ZA-A 916741.

It is quite generally also known in regard to the use of medicaments for inhalation in powder form for active substances to be combined by the application of prefabricated active substance mixtures. Corresponding proposals are to be found in EP 0 416 951 A1 and WO 93/11773, for example for the combination of salmeterol with fluticasone or formoterol with budesonide.

WO 00/74754 and many other publications over more than twenty years describe that a serious problem arises in regard to moisture, particularly with powder inhalers. In that respect moisture can not only have a disadvantageous effect on the pharmaceutically active medicament composition but in particular can adversely affect the interplay of physical and chemical parameters of the combination of active substance and adjuvant substances. As a result for example lumps can occur or breakdown of the inhaled powder into particles capable of reaching the lungs can be impeded. All those circumstances can lead to problems in regard to dosability and the effectiveness of administration of a medicament powder.

To alleviate those disadvantages various attempts have already been made in the past to reduce the penetration of moisture into a powder inhaler by the use of seals. In addition attempts were made to reduce the detrimental effects of moisture which has penetrated into the inhaler, by the provision of drying agents in order to absorb the moisture and in particular to keep down the level of air humidity in the storage chambers. Sealed dosing cavities in a multi-dose powder inhaler as well as a multi-digit counting mechanism are known from WO 92/00771. It will be noted however that dosing is only described by way of a rotary movement of a frustoconical dosing member.

Measures for moisture protection of medicament in powder form for inhalation in respect of dosing by means of a dosing slider are described for example in DE 102 02 940 A1, US 2003 0136405 A and WO 03/061742 A2.

STATE OF THE ART

Particularly with conventional aerosol inhalers, it was in many cases considered that actuation for dose delivery from the aerosol container and the fact of sucking in an airflow by the patient using it has to be co-ordinated, was a disadvantage. That considerably reduces the reliability of application of the medicament into the lung. Many different solutions have therefore been proposed in order to decouple actuation by the patient from the inhalation process and thus application of the dose. The difficulty in synchronizing the inhalation with the manual operation of the distributor part of an inhaler is for instance discussed in U.S. Pat. No. 5,239,992 A.

Numerous inventors have therefore already concerned themselves with the problem of inhalation-triggered dose delivery in the case of inhalers, for decades. For example DE 39 01 963 C1 discloses automatic actuation of a valve of an aerosol container. In that respect the invention described in that document includes sensor devices as well as an electronic control and various proposals for an actuating mechanism driven by electric motor means. In the Figures the patent specification includes a whole series of proposals for possible design configurations of the actuating mechanism which are all based on a rotary drive movement by means of an electric motor and provide for conversion into very small travel movements which are required for the actuation of a valve of an aerosol container which is under pressure.

However, from U.S. Pat. No. 5,113,855 A a proposal is known to at all separate the dosing and aerolization of medicament powder totally from the inhalation step to avoid the need for any triggering.

An inhalation-triggered opening and closing movement of a closure of a dosing passage is known from WO 99/47199 and WO 99/06092. In accordance with the disclosures in those documents, a spring-loaded closure of a dosing passage is moved by way of a valve flap which is disposed in a main air passage and which is actuated by the inhalation flow of the patient. The closure is pulled away upon corresponding deflection of the valve flap from the opening of the dosing passage and returns due to spring force into its starting position when the valve flap is no longer held open by the airflow. It will be appreciated however that this arrangement also does not have any seal as that dosing flap is only intended to close a dosing passage and is not in communication with a storage container for powder drugs. The actual dose delivery operation is effected by opening an individual dose blister in well-known form. Evidently the aim is only to ensure that no medicament powder passes into the air passage extending straight from the front rearwardly through the device, and probably trickles out when the inhaler is in an inclined position.

FR 2 709 653 A discloses a dosing device which is spring loaded from depressing a knob by the user, and the dosing device is released by a flap to move to a discharge position when a patient exerts suction in the inhalation duct.

Inhalation-triggered delivery of a dose from an aerosol container under pressure is known for example by prior use by Fujisawa Deutschland GmbH. In the case of the aerosol inhaler which is marketed by that corporation under the mark Junik® Autohaler® the aerosol container is biased by the user prior to the inhalation operation, insofar as a lever is used to compress a compression coil spring which presses against the container. The aerosol container is held by a movable frame connected to an air flap. When the air flap is deflected by the inhalation suction of the patient or otherwise mechanically, the frame is pivoted away to such an extent that the aerosol container can move with respect to the dosing valve which is held in a firm seat, to such an extent that the dosing valve opens to deliver a dose. In that respect the biasing of the spring is sufficient to overcome the closing force of the dosing valve. The aerosol container remains in the last position until the lever is pivoted back into its starting position again by the user. What is very troublesome for the user is the relatively hard and loud triggering impact upon activation of the dosing operation due to the quite high spring biasing and the comparatively large mass of the aerosol container, which is moved in the triggering operation.

Another inhalation-triggered opening of an aerosol container for dosing purposes by means of a spring which is activated by the actuation of a protective cap is known from WO 93/24167 (Norton Health Care Ltd., GB). The aerosol container is held in a readiness position by an evacuated and sealed intermediate chamber against the force of the spring. The dosing operation is effected by way of an airflow-actuated valve which permits venting of the intermediate chamber and thus release of the spring and a downward movement of the aerosol container. As the dosing valve of the aerosol container is held fast the movement of the container leads to an opening movement of the valve and thus delivery of an aerosol dose. That patent application at the same time also describes dose counting with an index ring which is advanced by way of a stepping mechanism with each dosing stroke movement. When a predetermined number of doses have been taken the ring disappears from the viewing window and can show an "empty" marking. Biasing of the spring is effected by way of a pivotal movement of a cap which actuates a receiving holding means for the aerosol container by way of a cam disc and a linkage, and in so doing compresses the spring.

The connection of a display formed by a ring which is moved progressively behind a viewing window, with an interchangeable powder cartridge, with a device for blocking the inhaler, is known from EP 1 616 592 A1. The blocking device is controlled by way of a groove in the ring and engages into the actuating mechanism for powder dosing. Similarly to the above-described document, the display however does not afford any possible way of dose-accurately reading off the doses which are still present in the storage container. Intervention of the blocking device can also not be predicted in accurate dosing relationship.

An MDPI in which the dosing element is actuated by way of a protective cap, with a refillable storage container having a plug which can serve as a container for a drying agent, and a dose counting mechanism, are known in principle from WO 93/03782.

EP 0 865 302 B1 discloses an inhaler in which a filled dosing cavity passes into a closure means upon further opening of a protective cap, and is closed by the closure means. A valve plate is releasable from its rest position in order to advance the closure means, in which case the advance movement of the closure means is permitted, against adjustable arresting means, only upon the application of a defined minimum intensity of inhalation by a patient, and the dosing cavity is opened only with the advance movement of the closure means so that the dose of medicament powder can be inhaled. That arrangement is highly special and complicated and expensive but does not prevent the loss of a dose which has not yet been inhaled, without affording particular protection from moisture. Upon actuation by a patient without inhalation occurring, the apportioned drug dose can remain for any period of time outside the storage means and in that case is exposed to atmospheric influences.

DE 198 25 434 C2 and EP 1 051 212 B1 disclose inhalers which each have a rotating dosing drum and a biasing mechanism which both activates a spring and also compresses an air volume, the mechanism being actuated by pivotal movement of a non-removable protective cap. Also described is a variant in which the biasing force for the metering operation is only produced by way of a rotary leg spring. The leg spring, triggered by the inhalation flow, drives the dosing drum of the inhaler from a filling position into an emptying position.

It is known from WO 95/31237 A1 to provide a spring on a dosing slider of an inhaler. The dosing slider can be pressed directly by hand by the user from a filling position into an emptying position against the force of a spring so that, after the dosing slider is released, it is pushed back by the spring into the filling position again.

None of the known documents however describes an arrangement which would make it possible for the drug supply including the dose pending for delivery to be protected from moisture and other detrimental influences independently of the operating behaviour of the patient as the user.

DESCRIPTION OF THE INVENTION

Therefore the problem of the invention is to provide an inhalation device which has improved use properties.

In accordance with the invention that problem is solved by an inhalation device for powder drugs comprising at least one storage chamber for accommodating a plurality of drug powder doses and a dosing device which includes at least one dosing slider which is movable approximately with a translatory movement in a dosing slider passage at least from a filling position into an emptying position, wherein the inhalation device further includes a device for inhalation-triggered automatic movement of the dosing slider from its filling position into the emptying position and a return device for automatic movement of the dosing slider back into the filling position.

Unlike the situation with previously known inhalers, the invention makes it possible for the first time for a dose of a powder medicament to be kept within the particularly moisture-protected region of the storage chamber, independently of any operating actions on the part of a patient, until actual inhalation. It is thus possible for the drug powder dose to be protected from ambient moisture for as long as possible and to avoid corresponding disadvantageous effects. In addition the automatic return of the dosing slider into its filling position immediately after dose delivery ensures that the hermetic moisture protection for the storage chamber is interrupted only for the shortest possible period, namely the moment of dispensing the apportioned drug dose. That provides that the remaining stored supply of drug is particularly effectively protected from moisture.

The inhaler according to the invention for the first time offers for a medicament stored supply with a plurality of drug powder doses, practically the same protection from ambient influences, as was hitherto only possible in individual dose blisters. In comparison with known inhalers for blister packs however it was possible to achieve a greater degree of economy, as well as better dose dispensing and thus better reproducibility of the medication. In addition the configuration of an inhalation device according to the invention affords the further advantage that overdosing of drug by multiple activation of the inhaler without effective inhalation is not possible. Finally, it cannot happen with the inhalation device according to the invention that, by virtue of actuation by the patient, a drug dose is presented which, upon careless or awkward handling with the inhalation device, could trickle out of the device prior to actual inhalation or could collect at unsuitable locations in the device. That therefore also affords particular protection against unintended under-dosing of the medicament upon inhalation by the user.

Preferably an inhalation device according to the invention is characterised in that the dosing slider passage with the at least one dosing slider and the storage chamber is sealed off relative to the environment at least in the filling position of the dosing slider.

In a particularly desirable embodiment of the invention the at least one storage chamber has at least one outlet opening through which the powder drug can issue under the influence of the force of gravity and the dosing slider has at least one dosing cavity, wherein the dosing cavity in the filling position is under the outlet opening and the dosing slider is movable out of its filling position into the emptying position approximately transversely with respect to the outflow direction of the drug powder from the outlet opening of the at least one storage chamber.

In order to provide for breath-triggered dosing and application of the drug powder, which is independent of the actual mechanical biasing of the inhaler by the patient, the inhaler preferably further includes a mouthpiece having an inhalation opening and an air passage which is in flow communication with the mouthpiece and through which a patient can suck an airflow for inhalation, wherein the dosing cavity in the emptying position of the dosing slider is in the air passage.

Desirably arranged in the air passage is a trigger device for signaling when a predetermined minimum airflow in the air passage is exceeded. Thus dosing of the drug powder can be triggered when a predetermined minimum airflow is exceeded.

In a particularly advantageous feature the inhalation device has a valve device in the air passage in order to substantially close the air passage, wherein the valve device is operatively connected to the trigger device for inhalation-triggered opening of a substantial part of the flow cross-section of the air passage when a predetermined minimum airflow in the air passage is signaled as being exceeded, in particular the valve device is part of the device for inhalation-triggered automatic movement of the dosing slider. By virtue of that arrangement, upon an inhalation by the patient, firstly a suction airflow is built up in the suction passage, which is already ready upon inhalation-triggered opening of the dosing passage cross-section and thus ensures complete emptying of the one dosing cavity of the dosing slider.

In a preferred embodiment the trigger or valve device comprises a pivotably mounted, directly or indirectly spring-loaded flap arranged in the air passage, wherein the air passage in the region of the flap is of a cross-sectional area which is large in relation to the inhalation opening, in order to ensure reliable reproducible triggering even if a weakened patient can only inhale at a low flow rate.

Particularly advantageously the flap is pivotable about a pivot axis and the pivot axis extends through or close to the centre of gravity of the flap. That provides that the flap is balanced about the pivot axis and thus in the event of an impact against the device, for example if the device is dropped, no moments induced by the mass of the flap occur about the pivot axis, thus preventing improper triggering of the device for inhalation-triggered automatic movement of the dosing slider.

In another advantageous embodiment of the invention the flap is coupled to a thrust rod which is operatively connected to the device for inhalation-triggered automatic movement of the dosing slider in such a way that the device for inhalation-triggered automatic movement of the dosing slider is held in a biased position by the thrust rod when the flap is in its rest position and the thrust rod releases the device for inhalation-triggered automatic movement of the dosing slider when the flap is deflected out of its rest position at least by a predetermined amount.

The coupling between the flap and the thrust rod can be formed for example by way of a toothed ring segment on the flap and a portion on the thrust rod, which is in the form of a rack. The term thrust rod may be understood in the context of the present application to also include other forms than a rod, e.g. the shape of a bent fork.

It can also be advantageous if the flap is pivotable about an axis and has a claw which is pivotable together with the flap about the axis and which holds a spring-loaded securing element and the contact face of which, with the securing element, is formed by a sliding or rolling pairing, wherein the securing element is operatively connected to the device for inhalation-triggered automatic movement of the dosing slider in such a way that the device for inhalation-triggered automatic movement of the dosing slider is held in a biased position by the securing element when the flap is in its rest position and the securing element releases the device for inhalation-triggered automatic movement of the dosing slider when the flap is deflected out of its rest position by at least a predetermined amount.

In another embodiment which is of an advantageously short structure the trigger device has a piston connected to the air passage and the air passage in the region of the piston has a cross-section which is large in relation to the inhalation opening, wherein the piston is coupled to a thrust rod which is operatively connected to the device for inhalation-triggered automatic movement of the dosing slider in such a way that the device for inhalation-triggered automatic movement of the dosing slider is held in a biased position by the thrust rod when the piston is in its rest position and the thrust rod releases the device for inhalation-triggered automatic movement of the dosing slider when the piston is deflected out of its rest position by at least a predetermined amount by a predetermined minimum airflow in the air passage, which is initiated by a user of the inhalation device.

In a particularly preferred embodiment of the invention the inhalation device according to the invention is characterised in that the device for inhalation-triggered automatic movement of the dosing slider out of its filling position into the emptying position has a drive element which can be moved into a readiness position against the force of a biasing spring and which has at least one sliding guide, an entrainment portion or a cam portion which is operatively connected to the dosing slider in its filling position and is releasably arrested in its readiness position by a trigger device, wherein the sliding guide, the entrainment portion or the cam portion is so designed that the drive element upon a movement out of the readiness position into a rest position moves the dosing slider at least into the emptying position thereof by way of one or more entrainment portions.

In a particularly preferred embodiment of the invention the inhalation device according to the invention is characterised in that the trigger device has an engagement portion interacting with a stepped stop element of the drive element, wherein the stepped stop element has a first step and the drive element is arrested in an intermediate position when the engagement portion of the trigger device interacts with the first step, and a second step and the drive element is held in its rest position when the engagement portion of the trigger device interacts with the second step, preferably, if the dosing slide is held in the emptying position by entrainment portions of the drive element and the dosing slide, respectively, in the intermediate position of the drive element. Such embodiment is particularly favourable in providing exact dosing of powdered medicaments to a patient as this embodiment does not only allow to deliver the drug powder from the storage chamber once the patient has established an inspiration flow sufficient to activate the trigger design, thus preventing the drug powder from being exposed to the atmosphere longer than needed, but also to present the drug powder to the inhalation air flow as long as the inspiration flow exceeds a predetermined threshold. Because of that removal of the full dose of drug powder presented is ensured during inhalation, thus providing best possible lung deposition at very little variations, so that the administration of medicaments via inhalation will also be possible for applications where exact reproduction of the prescribed dose is required.

Preferably the inhalation device further includes a return device for automatic movement of the dosing slider back into the filling position, the return device including a return spring. In that respect the return of the dosing slider into its filling position is not dependent on the inertia of the drive element and not substantially on the position of the inhalation device. The dosing slider is preferably connected by means of a return spring and is moved thereby back into the filling position, wherein the sliding guide, the entrainment portion or the cam portion is also so designed that in the rest position of the drive element the dosing slider can return into the filling position due to the force of the return spring. That ensures secure reliable sealing integrity for the stored drug supply, which is independent of component tolerances.

That sealing integrity is particularly reliably maintained if the drive element in its rest position is out of engagement with the dosing slider.

In an advantageous embodiment of the invention the inhalation device is characterised in that the drive element is formed by a linearly movable sliding guide carrier.

The return device for automatically moving the dosing slider back into the filling position can include a further sliding guide portion. Such an arrangement affords a positive guidance effect, as in the case of the forward movement. With such an arrangement, it is possible to prevent temporary opening of the seal at the dosing slider if for example the device falls to the ground.

It is particularly simple if the sliding guide or the cam portion is of a rectilinear configuration. Adaptation of the transmission between for example a drive spring and the dosing slider in dependence on the actuating travel can be obtained if the sliding guide or the cam portion is of a curved configuration, in particular of an eccentrically curved configuration.

Preferably a resilient element is used for storage of the energy necessary for the dosing movement.

A particularly compact arrangement with a torsion or rotary leg spring can be achieved if the sliding guide or the cam portion is of a helical configuration.

In a particularly preferred embodiment of the invention the drive element is formed by a drive rocker pivotable about a first pivot axis. That arrangement makes it possible to achieve a particularly reliable mode of operation substantially independently of manufacturing tolerances and there is a reduced risk of operational disturbances, for example after the inhalation device has been dropped.

Particularly in terms of simple and inexpensive assembly of an inhalation device according to the invention it is advantageous if the biasing spring and/or the return spring is a spring selected from a group of springs consisting of a coil spring, a spiral spring, a torsion spring, an elastically deformable shaped body and a compressed air storage means.

A particularly desirable adaptation in respect of the kinematics of the sliding guide carrier can be achieved if the biasing spring has a non-linear characteristic.

An inhalation device according to the invention is protected particularly well from inadvertent actuation if there is provided a rotary knob which is operatively connected to the sliding guide carrier and which has an operating handle, wherein the sliding guide carrier can be moved into its readiness position against the force of the biasing spring by a user with the rotary knob. Rotational actuating movements do not occur randomly and unintentionally under usual conditions, for example when putting a hand into a jacket pocket in which an inhalation device according to the invention is to be found, so that unintentional biasing of the device is avoided.

An inhalation device according to the invention can be reliably operated for patients suffering from degenerative diseases on the hands such as for example severe rheumatism, gout or arthrosis, if there is provided an actuating button operatively connected to the sliding guide carrier, wherein the sliding guide carrier can be moved into its readiness position against the force of the biasing spring with the actuating button by a user.

An embodiment of an inhalation device according to the invention, which is particularly preferred and operationally reliable and safe in respect of incorrect operation is characterised by a closure or protective cap for the mouthpiece, wherein the closure cap is non-losably connected to the inhalation device and is movable from a closure position in which the closure cap covers the mouthpiece into an operative position in which the mouthpiece is accessible to a patient. In that way it is impossible to use the inhalation device without previously activating it.

Activation of the biasing device for the sliding guide carrier by opening or closing the closure cap can be implemented if the closure cap or the sliding guide carrier has one or more entrainment portions and the closure cap is movable out of the closure position into the operative position substantially rectilinearly, or rotationally, or with a combined movement.

In an embodiment the closure cap or the sliding guide carrier has a sliding guide complementary to the entrainment portion or portions in such a way that the sliding guide carrier is movable by the movement of the closure cap out of the closure position into the operating position against the force of the biasing spring from its rest position into its readiness position.

An inhalation device according to the invention is particularly suitable in practical use if the complementary sliding guide has a track for the entrainment portion or portions so that the closure cap is also movable in the readiness position of the sliding guide into the closure position. That ensures untroubled functioning even if for any reasons the device is closed again without successful inhalation and the closure cap is later opened again.

A particularly high level of safeguard against malfunctions, particularly upon being dropped, for an inhalation device according to the invention is achieved if the track is such that the sliding guide carrier is fixed in its readiness position by entrainment portions of the closure cap independently of the trigger device when the closure cap is in its closure position.

In that respect it is particularly desirable if the complementary sliding guide is inclined with respect to the guide at an angle $\alpha$ at which no self-locking can occur, in particular between 15° and 45°, in particular if the complementary sliding guide extends non-rectilinearly.

For making use of a pivotal movement for biasing the biasing spring for the sliding guide carrier it is advantageous if the closure cap has at least one entrainment portion and the closure cap is movable out of the closure position along a guide substantially rectilinearly into an intermediate position and is pivotable out of the intermediate position into the operative position, wherein the inhalation device further has an eccentric disc operatively connected to the sliding guide carrier so that the eccentric disc is rotated by the entrainment portion of the closure cap upon the rectilinear movement thereof about a fixing axis in such a way that the sliding guide carrier is movable from its rest position into its readiness position by the movement of the closure cap out of the closure position into the intermediate position by way of the eccentric disc against the force of the biasing spring.

Alternatively it may also be advantageous if the closure cap has a pressure lever and the closure cap is pivotable out of the closure position into the operative position, wherein the pressure lever of the closure cap is pivotable about an axis in such a way that the sliding guide carrier is movable from its rest position into its readiness position by the movement of the closure cap out of the closure position into the operative position by way of the pressure lever against the force of the biasing spring.

In an embodiment which is particularly simple to operate for the user the biasing of the dosing mechanism is achieved by a purely rotational movement of the protective cap.

In another particularly preferred and advantageous embodiment of the invention the closure cap has at least one entrainment portion and a transmission rocker which is operatively connected to the driver rocker and which is pivotable about a second pivot axis and the closure cap is pivotable out of the closure position into the operative position about a third axis, wherein the at least one entrainment portion of the closure cap co-operates with at least one operative end of the transmission rocker in such a way that the drive rocker is movable out of its rest position into its readiness position by the movement of the closure cap about the third axis out of the closure position into the operative position by way of the transmission rocker against the force of the biasing spring.

That enables even patients who are under severe stress reliable and secure inhalation without particular handling operations having to be implemented. As a result an inhalation device according to the invention is also particularly suitable for patients suffering from severe acute asthma attacks or patients who must still reliably inhale a medicament under exceptional psychological and physical conditions.

It is particularly desirable if the drive rocker and the transmission rocker are in mutual engagement in such a way that their rotation takes place in opposite relationship about the first and second pivot axes. That arrangement provides that the moments involved upon triggering drug delivery substantially cancel each other out so that the patient is only slightly adversely affected by return forces which are perceived as a knock and corresponding noise. As a result acceptance of a medication with an inhalation device is markedly improved. That is the case in particular if the moment of inertia of the drive rocker about the first pivot axis and the moment of inertia of the transmission rocker about the second pivot axis are approximately equal.

In a particularly advantageous configuration the inhalation device according to the invention is characterised in that the at least one operative end of the transmission rocker is of such a configuration that the operative end is connected in positively locking relationship by the at least one entrainment portion of the closure cap upon movement of the closure cap out of the closure position into the operative position about the third axis and transmits the moment applied by the at least one entrainment portion to the transmission rocker and elastically evades the entrainment portion upon movement of the closure cap out of the operative position into the closure position. By virtue thereof it is possible for the closure cap to be moved over the mouthpiece again in a protective position even if a drug dose has not been taken.

In a particularly operationally reliable configuration the inhalation device according to the invention is characterised in that the transmission rocker has two rocker elements which are arranged on both longitudinal sides of the inhalation device pivotably about the second pivot axis and are connected together with at least one yoke, wherein the thrust rod holds the transmission rocker in the biased position of the drive rocker by engagement with the yoke when the flap is in its rest position and the thrust rod enables the travel movement of the yoke when the flap is deflected out of its rest position at least by a predetermined amount so that the transmission rocker and the drive rocker are movable by the biasing spring out of their readiness position into their rest position.

In an embodiment of an inhalation device according to the invention which is particularly protected against unintended under-dosing, there is further provided a counting device for detecting the number of delivered drug doses, wherein the counting device individually detects each dosing operation and the counting device is connected to a locking device which blocks the inhalation device upon the attainment of a predetermined number of delivered doses so that further use is no longer possible and in particular the closure cap is no longer movable into the closure position. That can prevent a patient by mistake seeking to inhale from an inhalation device which no longer has a sufficient stored supply of medicament. In that way a possibly life-threatening incorrect dosage can be very substantially avoided. In a different embodiment of the invention the same advantage will be obtained if the counting device is connected to the engagement portion of the trigger device and the stepped stop element of the drive element has an opening or recess, and the drive element is urged by the biasing spring to a blocking position, when the engagement portion engages with the opening or recess. More preferably, the drive element in its blocking position engages blockingly into the path of the closure cap so that the closure cap can no longer be moved into the closure position. Advantageously the counting device includes a dose-accurate display.

An inhalation device according to the invention operates particularly reliably in that respect if the locking device has a spring-loaded locking element which engages into a groove which is opened at a predetermined number of doses and in that case blockingly engages into the mechanism of the actuating element so that further use of the inhaler is prevented and in particular the closure cap can no longer be moved into the closure position.

Particularly clear signaling for an exhausted stored supply of medicament is achieved even for visually impaired patients if the locking device is coupled to a signal plate which is displayed upon blocking engagement into the mechanism of the actuating element or the actuating element is clearly visibly blocked.

Particularly preferably the locking device has a spring-loaded blocking rod which is movable from a rest position into a blocking position upon the attainment of a predetermined number of delivered doses and in its blocking position engages blockingly into the path of the closure cap so that the closure cap can no longer be moved into the closure position. That arrangement provides that both a particularly clear signaling action is achieved and also (futile) further use of the inhalation device and thus undesirable under-dosing is prevented.

To provide for efficient moisture protection for the powder drug disposed in a storage chamber of an inhalation device according to the invention, it is advantageous if the at least one storage chamber has at least one outlet opening through which the powder drug can issue under the influence of the force of gravity, and a filling opening which is disposed substantially in opposite relationship to the outlet opening, wherein the filling opening is sealingly closed.

In that respect an optimum sealing action which is independent of component tolerances is achieved if the filling opening is closed with an aluminium blister film and sealed with a LDPE layer.

For short series or for individual operations of filling the storage chamber, for example in the case of especially produced galenic preparations of a medicament, it is desirable, in relation to manual filling, if the filling opening is closed with a cover which screws to the wall of the storage chamber surrounding the filling opening and which is sealed in relation to the wall of the storage chamber with a seal fitted between the cover and the wall.

An embodiment of an inhalation device according to the invention which is both suitable for automation and also better protected from subsequent manipulation is characterised in that the filling opening is closed with a cover which is connected by an injection connection to the wall of the storage chamber which surrounds the filling opening, wherein an elastic seal or a yielding sealing rib on the cover and/or the wall is sealingly also braced between the cover and the wall.

Particularly good protection from moisture for the powder medicament is achieved if the storage chamber is at least partially enclosed by a wall which includes a material with a high level of water vapour diffusion resistance.

In a particularly advantageous embodiment which affords particularly good long-term moisture protection for the medicament the dosing slider passage has at its one end towards the environment an opening through which a part of the dosing slider can pass and a contact surface for a seal is provided around the opening, wherein the dosing slider has a sealing surface which is provided in a plane approximately in transverse relationship with its direction of movement out of the filling position into the emptying position.

In that respect it is particularly desirable if an elastic seal is provided on the dosing slider and/or the contact surface. Errors upon assembly can be reduced in that respect if the elastic seal is formed by injection on the dosing slider passage and/or the dosing slider.

Alternatively sealing integrity can be formed by a sealing rib on the dosing slider passage and/or the dosing slider, which is sealingly deformable by a biasing force which holds the dosing slider in the dosing slider passage.

Keeping the medicament dry is improved without mechanically loading or compacting the medicament powder when shaking the inhalation device if an encapsulated drying agent is disposed in the storage chamber, wherein the drying agent body or the drying agent capsule is fixedly pressed or latched in the cartridge body.

Particularly good acceptance in respect of an inhalation device according to the invention is achieved if the inhalation device further has a display for signaling inhalation readiness and/or successful delivery of the medicament.

An application of particles which can pass to the lungs, such application being reliable throughout the entire intended period of use of an inhalation device, even in the event of only occasional use and cleaning by the user, to achieve satisfactory hygiene, can be attained by a breaking-down device for breaking down agglomerates and the like in the drug powder in flow communication with the mouthpiece and the dosing passage, wherein the mouthpiece and the breaking-down device are removable for cleaning by the user and the mouthpiece and the breaking-down device are so adapted that they can only be removed and fitted together or are of a one-piece nature.

The inhalation device of the invention is particularly useful in a number of medical applications if the at least one storage chamber is provided by a cartridge holder device and a lid, wherein the lid has a shape capable of receiving the drug powder content of the storage chamber in an upside-down position of the inhalation device. That allows pre-mounting of the cartridge holder and the dosing slider during manufacture of the inhalation device including testing. The lid may serve as an open-top cartridge and filled with the appropriate amount of drug powder in the pharmaceutical manufacturing line, and directly inserted into the inhalation device held upside down. So the inhalation device can be delivered ready to use from the medicament manufacturer. Preferably, the lid is sealingly fixed onto the cartridge holder by snap connectors.

A especially useful embodiment of the inhalation device according to the invention is characterised in that the cartridge holder device comprises two storage chambers each covered by a lid, wherein the cartridge holder device comprises a twin dosing slider. This allows easy and accurate dosing from two different drug reservoirs, for instance for the combination of medicaments which may not be stored together to avoid degradation.

BRIEF DESCRIPTION OF THE DRAWINGS

The invention, its aspects, advantages and uses will be described in greater detail hereinafter by means of embodiments by way of example illustrated in the drawings. The embodiments illustrated in the drawings and described hereinafter are intended only to serve for better understanding and are not to be interpreted limitatively. In the drawings.

DESCRIPTION OF PREFERRED EMBODIMENTS OF THE INVENTION

Figure 1:
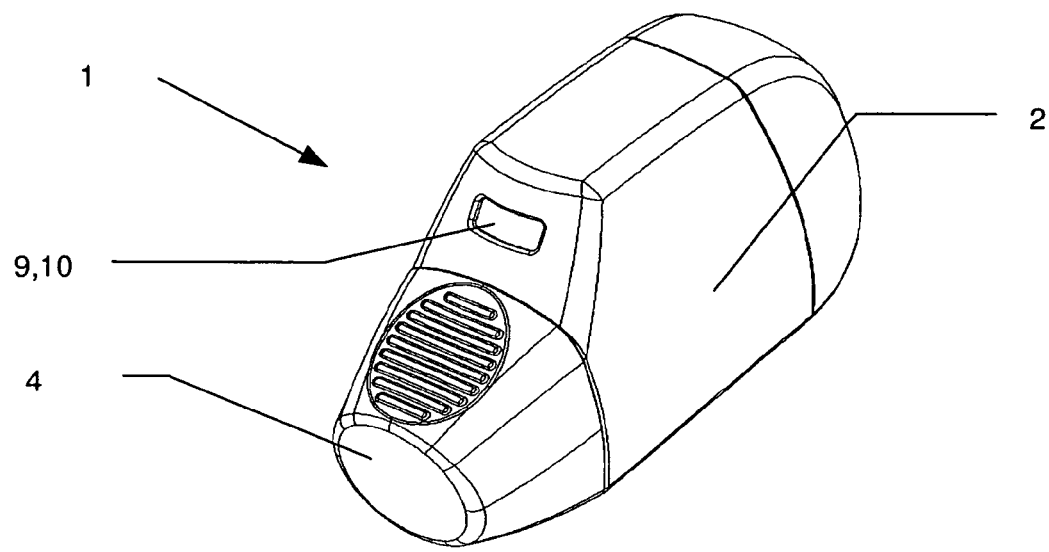
FIG. 1 shows a perspective view of an embodiment of an inhalation device according to the invention with the closure cap closed.

FIG. 1 shows a perspective view of an embodiment of an inhalation device according to the invention indicated generally by reference 1. Such an inhalation device 1 is also referred to as an inhaler. The inhalation device 1 according to the invention is provided for the delivery of a large number of individual doses of a drug in powder form. Special inhalation devices of that kind are therefore also referred to as powder inhalers and often abbreviated to MDPI (multi-dose powder inhaler). The inhaler 1 includes a housing 2. The housing 2 desirably comprises two halves with a separation line along the central axis along the inhaler 1. That means that the housing portions can be easily manufactured using plastic injection moulding and it has been found that, with such an arrangement, a powder inhaler 1 is simple to assemble. The housing 2 can also include a separate housing cover so that a separate drug powder cartridge 3 can be subsequently inserted into the assembled inhaler. The housing cover can then close the housing 2 for example with a snap connection which is no longer to be released from the exterior. Such a housing cover can also be removable if it is desired that the drug powder cartridge 3 is to be replaceable. The inhaler 1 further includes a closure cap 4 which according to the invention is non-losably connected to the housing 2. The closure cap 4 can be pivoted from its closure position into its operative position by suitable user involvement, about an axis 7. In another embodiment (FIGS. 12 and 13) the closure cap 4 can be pulled a distance away from the housing 2 in the longitudinal direction of the inhaler and preferably pivoted downwardly in order to clear a mouthpiece 5 disposed therebeneath. An inhalation opening 6 is to be found in the mouthpiece 5.

A patient can inhale a drug in powder form through the mouthpiece 5 by embracing the mouthpiece 5 with his lips and breathing in through the inhalation opening 6. After inhalation the closure cap is desirably pivoted back from its operative position (FIG. 2) into its closure position (FIG. 1) again and possibly pushed so that it again covers over the mouthpiece 5. In that way the interior of the inhaler 1 is well protected and preferably sealingly closed so that no dirt can penetrate into the interior of the inhaler. As respiration air is usually sucked out of the inhaler by the patient and thus particles which are disposed in a movable condition in the interior of the inhaler pass into the respiratory tract, keeping the interior of an inhaler 1 clean is extremely important. Furthermore, the ingress of water droplets into the interior of the inhaler 1 can be substantially prevented by the closed closure cap 4, for example if a patient is handling his inhaler in the open air in rainy weather. It is precisely under such weather conditions that there is frequently a need for medicational treatment of respiratory tract diseases.

Furthermore a transparent window 9 for a display 10 of a counting device 11 is also disposed in the housing 2 of the inhaler 1 on the side at which the mouthpiece 5 and the closure cap 4 are disposed in the closure position thereof, which hereinafter is referred as the front side 8 of the inhaler 1. By virtue thereof, a patient using the inhaler 1 can simply read off the accurate-dosage number of drug doses which have already been delivered from the drug supply stored in the inhaler or preferably an accurate-dosage number of the drug doses still available from the drug supply is displayed in such a way that it can be easily read off. In that fashion the patient is in a position to attend to replacement in good time if for example the number of remaining doses is no longer sufficient for the duration of a vacation journey. Experience has shown that such powder inhalers 1 are used in particular in relation to chronic diseases of the respiratory tract or other chronic diseases in relation to which medicaments can be administered by way of the respiratory tract, and frequently regular inhalation of a medicament is vitally necessary for the patient. A high degree of reliability in terms of the drug doses available by way of the inhaler 1 is therefore essential for such patients.

Furthermore, also displayed at the front side 8 at the inhaler 1 is a readiness display 12 which can also be seen through a transparent window 9 for showing that the inhaler 1 is ready to deliver a drug dose, and for displaying that a drug dose has been successfully dispensed from the inhaler 1. Preferably operational readiness or successful administration of a drug dose is signaled by a colour change, in which respect a green representation has proven appropriate for displaying operational readiness and a colour change to a red representation has proven appropriate for displaying successful administration. At the same time the red representation signals that the inhaler 1 is first to be prepared for renewed inhalation. In the case of the inhaler 1 according to the invention that is particularly preferably effected by actuating the closure cap 4 from the closure position into the operative position.

The provision of transparent windows 9 instead of usual openings affords particular protection from the ingress of contamination and impurities and moisture. The arrangement of the windows 9 for the display 10 and the readiness display 12 as well as the closure cap 4 which is preferably pivoted downwardly in the operative position also encourages a patient to hold the inhaler 1 correctly upon inhalation so as to ensure reliable dosing and delivery of a powder drug. Preferably in that respect the dimensioning is so selected that, when the inhaler is held inverted, the closure cap 4 which in the operative position collides with the nose of the patient if the latter endeavours to close the lips around the mouthpiece 5.

Alternatively the display 10 and/or the readiness display 12 can also be so arranged that they are covered over by the closure cap 4 in the closure position thereof. That makes it possible to achieve good protection from the ingress of contamination and water droplets even without additional transparent window elements.

In its interior the inhaler 1 includes a storage chamber 13 for accommodating a plurality of drug powder doses. The storage chamber 13 can desirably be formed in a cartridge 3. The arrangement of the storage chamber 13 in a separate cartridge 3 has the advantage that the inhaler 1 according to the invention can be manufactured and assembled independently of filling thereof with the powder drug and that manufacturing and assembly procedure does thus not have to be implemented under pharmaceutical cleanliness conditions. The separate cartridge 3 can be filled under suitable cleanliness conditions and later fitted to the inhaler 1. In addition that concept makes it possible to offer an inhaler 1 with different powder drugs without this meaning that manufacture and assembly of the inhaler, except for the cartridge 3, have to be implemented at the location of manufacture or filling of the corresponding drug. In addition this concept makes it possible for example for inhalers 1 to be kept in stock without the cartridge 3 and for cartridges 3 possibly even to be individually filled with galenic individual preparations of medicaments and fitted into the inhaler 1 from the supply in stock and made available to the patient.

Figure 3:
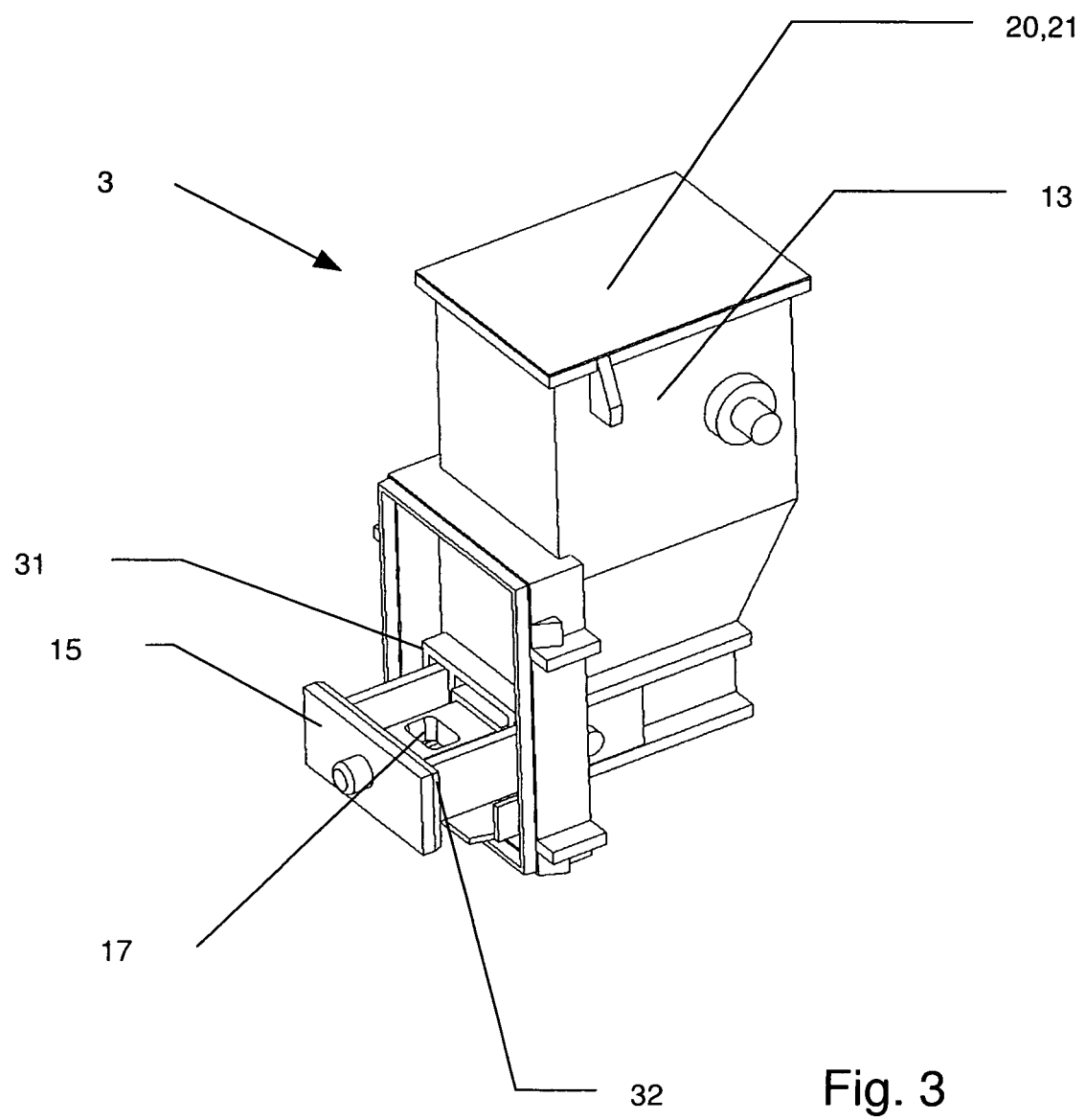
FIG. 3 shows a perspective view of the cartridge of an embodiment of an inhalation device according to the invention illustrating the principle involved.

The drug powder cartridge 3 shown in FIG. 3 with the storage chamber 13 includes an outlet opening 14 through which the powder drug can issue under the influence of the force of gravity. Furthermore a dosing device which includes a dosing slider 15 is desirably integrated into the cartridge 3. The dosing slider 15 can occupy in a dosing slider passage 16 a filling position (as can be seen for example in FIG. 17) in which a dosing cavity 17 is under the outlet opening 14 so that the powder medicament 18 in the storage chamber 13 can pass into the dosing cavity 17 under the influence of the force of gravity. Furthermore the dosing slider 15 is movable in the dosing slider passage 16 into an emptying position (shown in FIG. 3) in which the outlet opening 14 is closed by the dosing slider 15 and the dosing cavity 17 issues from the dosing slider passage 16 to such an extent that the drug powder can be taken from the dosing cavity 17 by an air flow. The movement of the dosing slider 15 from the filling position into the emptying position and from the emptying position into the filling position is effected with a translatory motion along the axis of the dosing slider passage 16. The dosing slider passage 16 has a closed bottom which at the same time forms the bottom of the dosing cavity 17 during the operation of filling the dosing cavity 17 in the filling position of the dosing slider 15.

Figure 4:
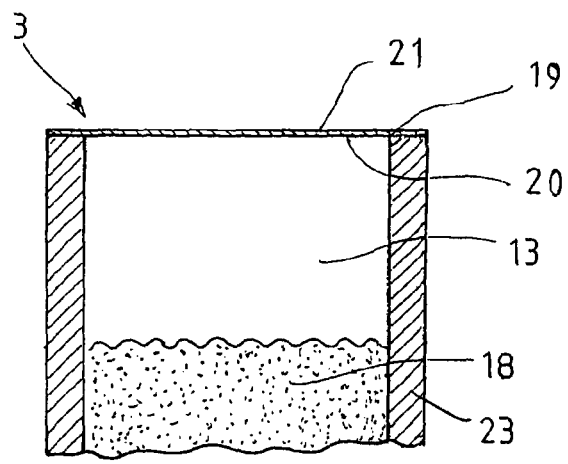
FIGS. 4 to 7 show diagrammatic views in section of various embodiments according to the invention of a closure of a cartridge from FIG. 3.

In addition the storage chamber 13 of the cartridge 3 has a filling opening 19 which is desirably disposed in opposite relationship to the outlet opening 14. The opening 19 serves to introduce the powder medicament into the storage chamber 13 in the required number of doses. The filling opening 19 is sealingly closed after the filling operation in order to ensure the purity of the medicament powder and to prevent the ingress of foreign substances. Desirably the filling opening 19 is closed with an aluminium blister layer 20 and the latter is sealed with an LDPE layer 21 comprising a low density polyethylene (FIG. 4). That manner of closing the opening can be carried out particularly well automatically and also affords the great advantage that that closure of the filling opening 19 is very substantially impenetrable for water vapour.

In practice it has been found that it is particularly important for the drug supply in the storage chamber 13 to be protected as well as possible from the ingress of moisture. There are a number of reasons for that. On the one hand the medicament can alter with interaction with moisture and in particular the medical effectiveness thereof can be impaired while on the other hand absorption of moisture in the drug powder easily results in lump formation so that it is difficult to achieve reproducible reliable dosage of the drug in use. Frequently such inhalers 1 are also used for diseases which do not constantly require medicament administration but in respect of which a suitable medicament has to be kept in readiness. In particular allergic diseases of the respiratory tract are to be considered in that respect. That means that the medicament 18 in the stored supply must remain stable and reliably dosable over a long period of time, even if a patient daily carries such an inhaler 1 about his person in his jacket pocket. The closure according to the invention for the filling opening 19 provides such long-term protection for the stored supply of medicament from the ingress of moisture.

Figure 5:
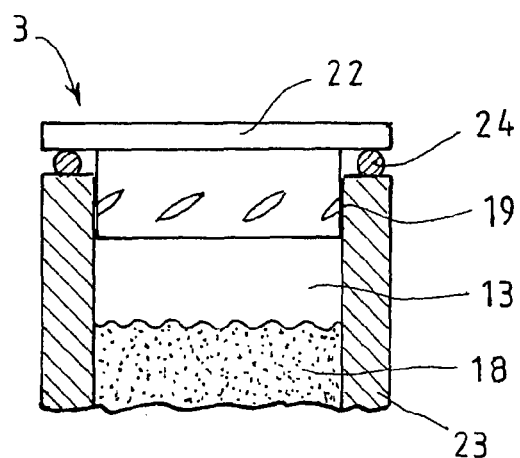

Particularly for the individual preparation of medicaments and filling thereof into a suitable cartridge 3, as already referred to hereinbefore, it may also be desirable for the filling opening 19 to be closed after the filling operation with a screw cover 22 and for a corresponding screwthread to be provided in the wall 23 of the cartridge 3, surrounding the filling opening 19 (FIG. 5). Desirably fitted between the cover 22 and the wall 23 is a seal 24 which for example can be made from a suitable TPE. Instead of an elastic seal 24 however it is also possible to provide a sealing rib 25 on the cover 22 or the wall 23 (see FIG. 6) which, when the cover 22 is fitted, is sealingly also braced between the cover 22 and the wall 23 and in that case is elastically or plastically deformed. By virtue of the arrangement with a screw cover 22, it is also possible for short series of cartridges 3 to be filled with a given medicament by hand and closed.

Figure 6:
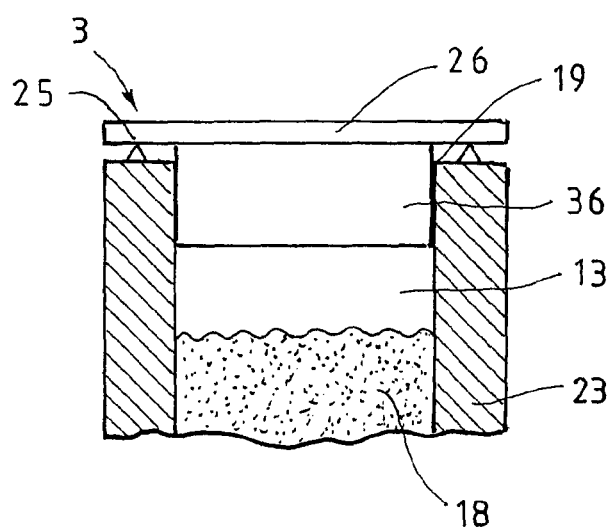

For automated filling however it may also be desirable to provide a cover 26 instead of a screw cover 22 and to join it to the wall 23 for example by ultrasound welding or to glue it in place (FIG. 6).

Figure 7:
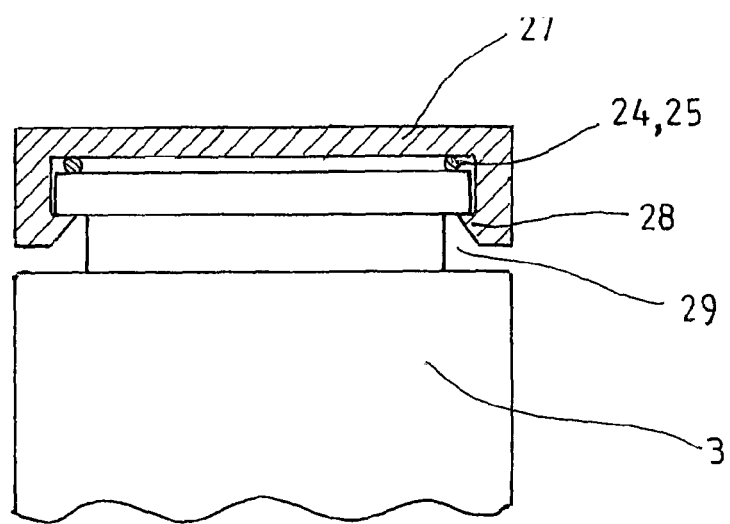

Particularly in filling processes which are carried out on a large technical scale however it may also be desirable for the cover to be in the form of a snap cover 27 and for a hook arrangement 28 and a groove 29 to be provided in the wall 23 and the snap cover 27 respectively, thus forming a spreading latching engagement or snap connection (FIG. 7). Preferably the groove 29 and the hook arrangement 28 are so arranged that, after fitment of the snap cover 27, as far as possible they can no longer be reached even with a tool so that after fitment the snap cover 27 can no longer be removed without destroying the cartridge. In the case of such a latching connection also it is desirable for an elastic seal 24 or a sealing rib 25 which upon assembly is also sealingly braced to be provided between the snap cover 27 and the wall 23.

Since, as already mentioned, the aim is to achieve a high level of sealing integrity for the cartridge 3 in relation to the ingress of moisture out of the ambient atmosphere it is desirable if the wall 23 includes a material which affords a particularly high level of water vapour diffusion resistance. Preferably however that material should still be suitable for processing by appropriate inexpensive production processes, for example by injection moulding. Some suitable materials are described for example in US 2003 013 64 05 A, to which reference is hereby directed.

Figure 8:
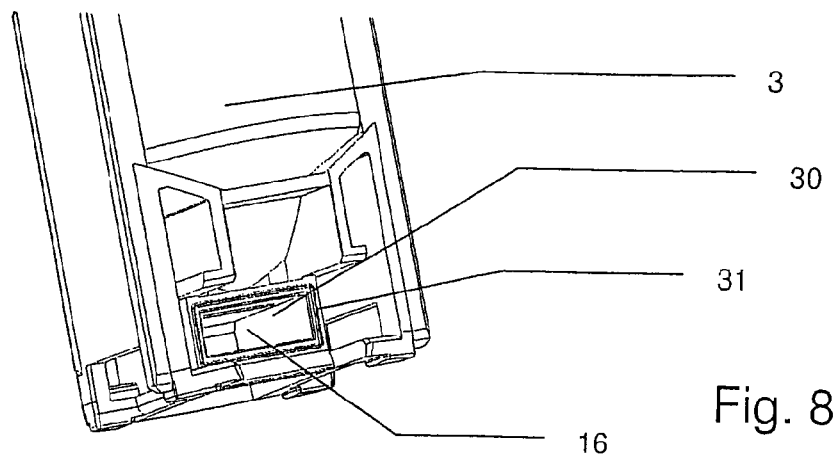
FIG. 8 shows a perspective partial view of an alternative configuration of the cartridge from FIG. 3.
Figure 9:
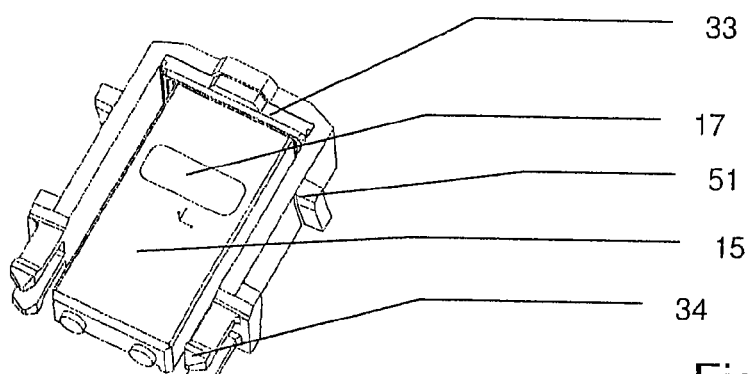
FIG. 9 shows a perspective view of a dosing slider for a cartridge as shown in FIG. 3.

Furthermore, for comprehensive moisture protection for the medicament 18 in the storage chamber 13 of the cartridge 3, it is advantageous in accordance with the invention that the dosing slider passage 16 has a corresponding opening 30 at its open end through which the dosing slider 15 can issue with the dosing cavity 17, wherein a contact surface 31 for a seal 32 is provided around the opening 30 and wherein the dosing slider 15 further has a sealing surface 33 which is arranged in a plane in approximately transverse relationship with the direction of movement out of the filling position into the emptying position (FIG. 8). In that respect it is equivalent from the point of view of the sealing function whether the elastic seal 32 is disposed on the contact surface 31 or the sealing surface 33 of the dosing slider 15, as shown in FIG. 9. Desirably the elastic seal 32 comprises a thermoplastic elastomer which is preferably injection moulded in a multi-component injection moulding procedure directly on the dosing slider 15 or the dosing slider passage 16. It will be appreciated however that it is also possible to provide a separate seal. The arrangement of the dosing slider 15 in the dosing slider passage 16 with the seal 32 can be seen from FIG. 3. Desirably the dosing slider 15 is also secured in its filling position by spring elements 34 so that the seal 32 is always slightly prestressed when the dosing slider 15 is in its filling position. That is particularly advantageous as long as the cartridge 3 is stored or transported outside the inhaler 1 in order always to achieve an optimum sealing action.

Figure 10:
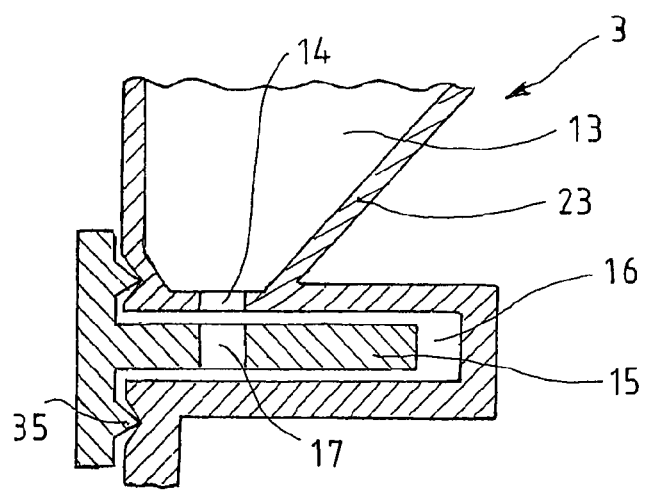
FIG. 10 shows a diagrammatic view in section of an alternative arrangement of a dosing slider in a dosing slider passage of a cartridge as shown in FIG. 3.

As an alternative to the elastic seal 32 a sealing rib 35 can also be formed on the dosing slider passage 16 or the dosing slider 15, as shown in FIG. 10. In that case the sealing rib 35 will be sealingly deformed by the biasing force which holds the dosing slider 15 in its filling position in the dosing slider passage 16 (FIG. 10).

So that, in spite of the above-described numerous and effective measures which very substantially prevent moisture from penetrating into the storage chamber 13 of the cartridge 3, any residual moisture can be absorbed or a moisture level which is required by virtue of particular properties of the medicament 18 can be set, a drying agent body or an encapsulated drying agent 36 can be disposed in the storage chamber 13 of the cartridge 3. Desirably the drying agent body or the drying agent capsule is pressed or latched in the storage chamber 13 of the cartridge 3. That measures holds the drying agent 36 away from the medicament powder 18 and in particular prevents the medicament powder 18 being mechanically loaded by the drying agent 36 in the event of vibration, shaking or shocks, in particular to prevent the medicament powder 18 from being compacted. That means that particularly reproducible dosing of the medicament powder 18 is possible, and also bridge formation of the medicament powder 18 over the outlet opening 14 is prevented and thus the overall reliability of the inhaler 1 according to the invention is improved.

Instead of the above-described preferred arrangement of a drying agent 36 in the storage chamber 13, a solid drying agent body, for example an injection moulded body of plastic material in which a drying agent is embedded, can be fixedly fitted in the form of a sleeve into the storage chamber 13. In addition a drying agent body can also be fixedly integrated in the cover 22, 26 or 27. Finally a drying agent 36 can also be incorporated as a component in a multi-component injection moulding procedure for manufacturing the wall 23 of the storage chamber 13.

Figure 12:
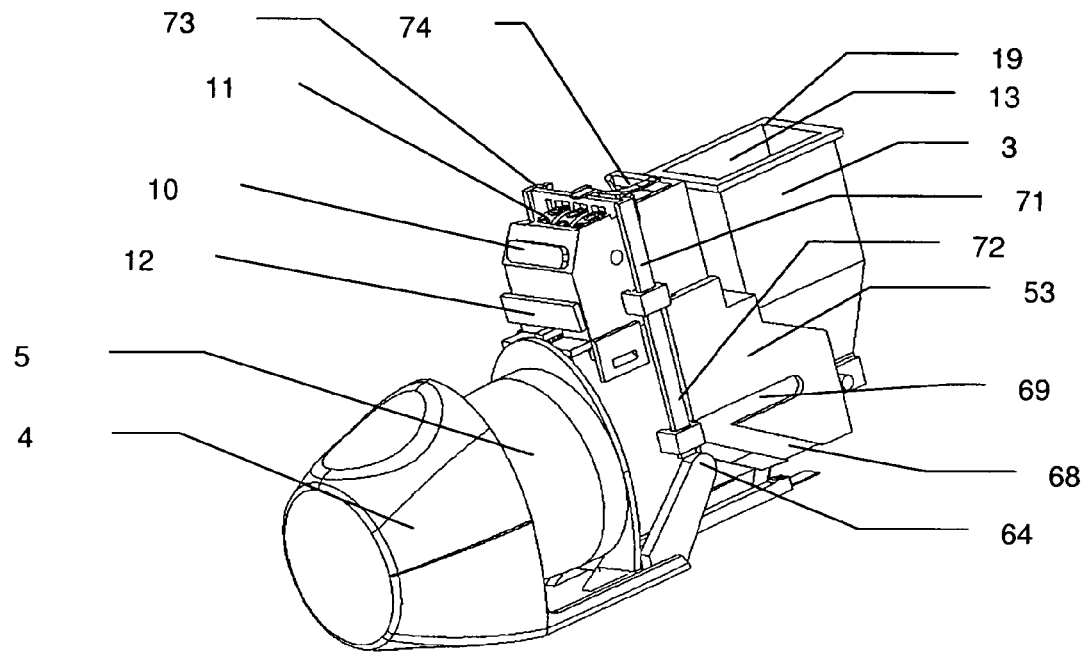
FIG. 12 shows a perspective view of a further embodiment of an inhalation device according to the invention with the housing removed, with further components being partially omitted.
Figure 13:
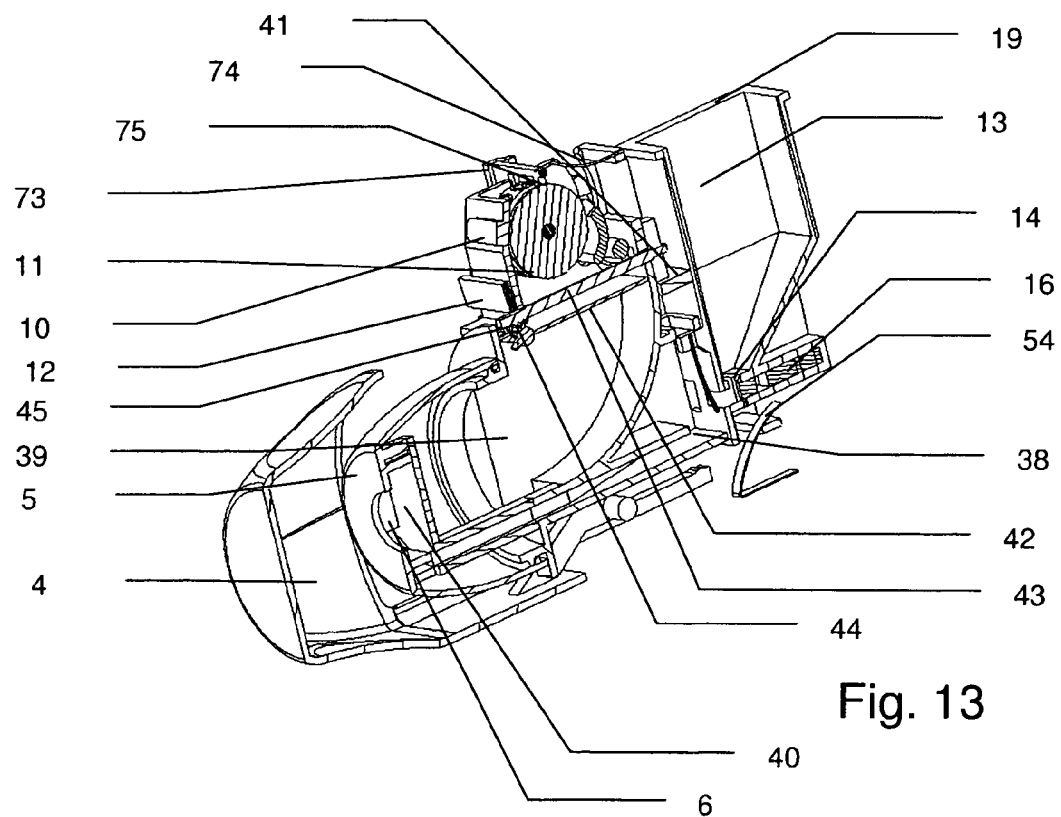
FIG. 13 shows a perspective sectional view of selected components of FIG. 12.

The structure in greater detail of an embodiment of an inhaler 1 according to the invention can be seen in FIG. 12. For the purposes of description the housing 2 and some further parts have been omitted from the illustrated view. FIG. 13 shows a sectional view of the inhaler 1 of FIG. 12. By way of example, but not necessarily so, the cartridge 3 with the storage chamber 13 for accommodating the plurality of drug powder doses is arranged in the rear region of the inhaler housing 2, as already described in detail hereinbefore. In addition the inhaler 1 includes a device for inhalation-triggered automatic movement of the dosing slider 15 out of a filling position into the emptying position and a return device for automatic movement of the dosing slider 15 back into the filling position within the dosing slider passage 16.

Those devices are described in greater detail hereinafter. Provided at the front end of the inhaler is the mouthpiece 5 which, as already mentioned, can be covered over by a closure cap 4. The inhalation opening 6 is provided in the mouthpiece 5. The mouthpiece 5 with the inhalation opening 6 is in flow communication with a dosing passage 38. A patient can suck an airflow through the dosing passage 38 upon inhalation and, by way of the dosing passage, receives the applied dose of a drug powder which is apportioned with the dosing cavity 17 of the dosing slider 15. In addition the mouthpiece 5 is in flow communication with an air passage 39. Provided within the mouthpiece 5 is a breaking-down device 40, for example in the form of a cyclone arrangement (see FIG. 13). The breaking-down device 40 is connected to the dosing passage 38 so that an airflow loaded with the medicament powder passes into the breaking-down device 40 from the dosing passage 38. The airflow is preferably strongly deflected a plurality of times in the breaking-down device 40 in order to break down agglomerates or similar accumulations of medicament powder so that the patient very substantially receives through the mouthpiece 5 drug particles which are of a uniform lung-negotiating particle size. In the embodiment shown in FIG. 13, with a parallel flow feed for the air in the dosing passage 38 and the air passage 39, the airflows thereof are brought together in the mouthpiece 5. In the embodiment shown inter alia in FIGS. 11, 17 and 18, the parallel flow path is omitted and the dosing passage 38 forms a part of the air passage 39.

In long-lasting use it is advantageous if the patient can remove and easily clean the mouthpiece 5 and the breaking-down device 40 without a tool, for example under a water tap. That is desirable in order for example to remove residues formed by respiration moisture, saliva or the like, with drug powder, from the mouthpiece and the breaking-down device 40. Bacteria or the like can also be introduced into the mouthpiece by the patient by way of the mouth, and they can also be removed in that fashion. In that respect it may also be desirable for the patient to be afforded for example a suitable cleaning solution.

After cleaning and possibly drying of the mouthpiece 5 and the breaking-down device 40 the patient re-fits those parts into the inhaler 1 in order to restore the inhaler 1 to full operability again. In that respect it is extremely important in terms of the effectiveness of medicament absorption that the breaking-down device 40 is in actual fact also fitted again and not for example the mouthpiece 5 without the breaking-down device 40. If the breaking-down device 40 is missing, there is the risk that the medicament powder is not sufficiently broken down into particles which can pass into the lungs, and accordingly the effectiveness of medicament administration is unexpectedly reduced. In order to prevent operating errors by patients who are also clumsy or unskilled the inventors found that it is desirable for the mouthpiece 5 and the breaking-down device 40 to be designed in such a way that they can only be removed and re-fitted jointly. That can be achieved by for example the mouthpiece 5 and the breaking-down device 40 being joined together upon assembly of the inhaler 1, by the formation of a snap-action connection, in such a way that a patient can no longer take those parts apart without destroying them. That is particularly suitable when the mouthpiece 5 and/or the breaking-down device 40 are of a configuration which is complicated from the production engineering point of view as that arrangement affords the advantage that the two parts can be manufactured separately. Particularly to reduce assembly costs and to avoid gaps and joins which possibly cannot be correctly cleaned or then dried, it is desirable for the mouthpiece 5 and the breaking-down device 40 to be produced in one piece for example by suitable shaping processes.

When a patient begins to draw in an airflow through the mouthpiece the dosing passage 38 is firstly closed by a valve device 41, in which respect the valve device can also be formed by another part of the inhaler being pushed in the manner of a slider into the flow path of the dosing passage 38 or by a corresponding opening being covered over. When now a patient begins with inhalation, a corresponding reduced pressure or airflow is firstly built up in the air passage 39.

Disposed in the air passage 39 is a trigger device which is described in greater detail hereinafter. That trigger device serves to signal when a predetermined minimum airflow in the air passage 39 is exceeded, in which case that minimum airflow can also be formed by the production of a predetermined reduced pressure in the air passage 39. Preferably, the air passage 39 is of a markedly enlarged flow cross-section in the region of the trigger device. In that way it is possible to produce comparatively high and uniform control forces with an element which for a large part closes the flow cross-section, even in the event of a comparatively low reduced pressure and with a low degree of scatter. In a preferred embodiment the trigger device includes a flap 42 pivotably mounted in the air passage 39. As already mentioned, in the region of the flap 42 the air passage 39 is of a cross-section which is particularly large in relation to the dosing passage 38. The flap 42 is held in the starting position preferably directly or indirectly by a spring loading. In a particularly advantageous feature the flap 42 is pivotable about a pivot axis 80 and the pivot axis 80 extends through or close to the centre of gravity of the flap 42. That provides that the flap 42 is balanced about the pivot axis 80 and thus, in the event of a knock against the inhaler 1, for example if the inhaler 1 is dropped, no moments induced by the mass of the flap 42 are generated around the pivot axis 80.

As can be seen from the diagrammatic view in FIG. 13 the flap 42 is coupled to a thrust rod 43. The thrust rod 43 is operatively connected to a device for inhalation-triggered automatic movement of the dosing slider 15, wherein the device for inhalation-triggered automatic movement of the dosing slider 15 is held directly or indirectly in a biased position by the thrust rod 43 when the flap 42 is in its rest position. The thrust rod 43 is actuated by the flap 42 when the flap 42 is moved by an inhalation flow in the air passage 39 by the patient. As will be described in greater detail hereinafter the thrust rod 43 releases the device for inhalation-triggered automatic movement of the dosing slider 15 when the flap 42 is deflected out of its rest position at least by a predetermined amount. That provides that the device for inhalation-triggered automatic movement of the dosing slider 15 is activated when a certain minimum airflow or minimum air pressure has been built up in the air passage 39 by the patient. The magnitude of the required minimum airflow or minimum reduced pressure in the air passage 39 can be set in that case by the effective cross-section of the flap 42 and a closing force which is to be overcome. In that respect the closing force can desirably be applied by a spring 99, connected to the flap 42 or the thrust rod 43 and holding the flap 42 in its rest position and therewith the thrust rod 43 in the position in which the device for inhalation-triggered automatic movement of the dosing slider 15 is held in its biased position by the thrust rod 43. In that case the thrust rod 43 can be directly or indirectly connected to the device for inhalation-triggered automatic movement of the dosing slider 15 and can be for example angled, or may have a shape of a bent fork, depending on how the device for inhalation-triggered automatic movement of the dosing slider 15 is respectively structurally designed and in what direction the thrust rod 43 is displaced by the flap 42.

As will be described in greater detail hereinafter that makes it possible to administer an appropriate dose of medicament to the patient at a time when the patient has built up a sufficiently great inhalation airflow in order to ensure that the greatest part of the medicament powder which is inhaled can pass into the lungs. In that way the moment of dose administration of the drug powder can be optimised completely independently of the operating behaviour and the co-ordination capabilities on the part of the patient and a very high level of reliability and efficiency in terms of medicament delivery to the patient is achieved irrespective of the capabilities or understanding on the part of the patient for the processes involved during inhalation. That not only enables an inhaler 1 according to the invention to be used in relation to a particularly wide circle of people, but an inhaler 1 according to the invention is therefore also particularly suitable for patients with whom medicament administration has to be effected reliably when shock conditions occur or under other panic conditions, for example in the case of spontaneous attacks. With the inhaler according to the invention a patient needs to do nothing other than suck on the mouthpiece 5 in order to receive an administration of the medicament powder which is adapted for optimum lung-negotiating capability.

A particularly compact arrangement and simple assembly can be achieved in that respect if the coupling between the flap 42 and the thrust rod 43 is formed by a toothed ring segment 44 on the flap 42 and a portion 45 on the thrust rod 43, that is in the form of a toothed rack. That arrangement and the arrangement of the dosing passage 38 and the air passage 39 can be clearly seen from FIG. 13.

Figure 14:
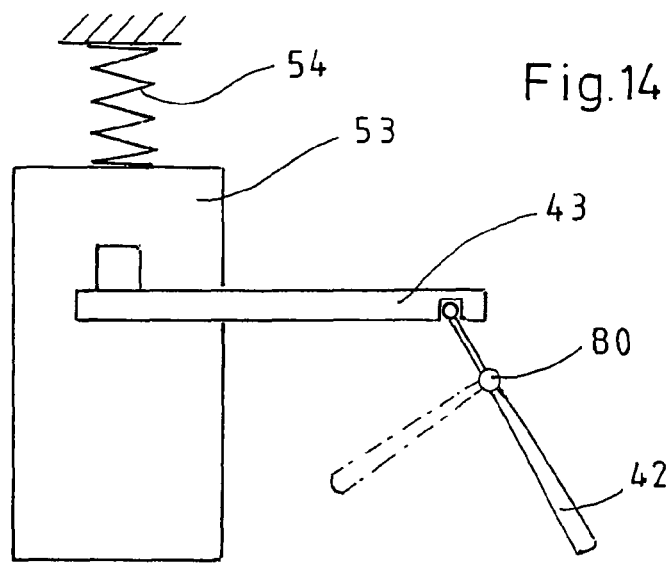
FIG. 14 shows a diagrammatic view showing the principle of a trigger arrangement of an inhalation device according to the invention.
Figure 15:
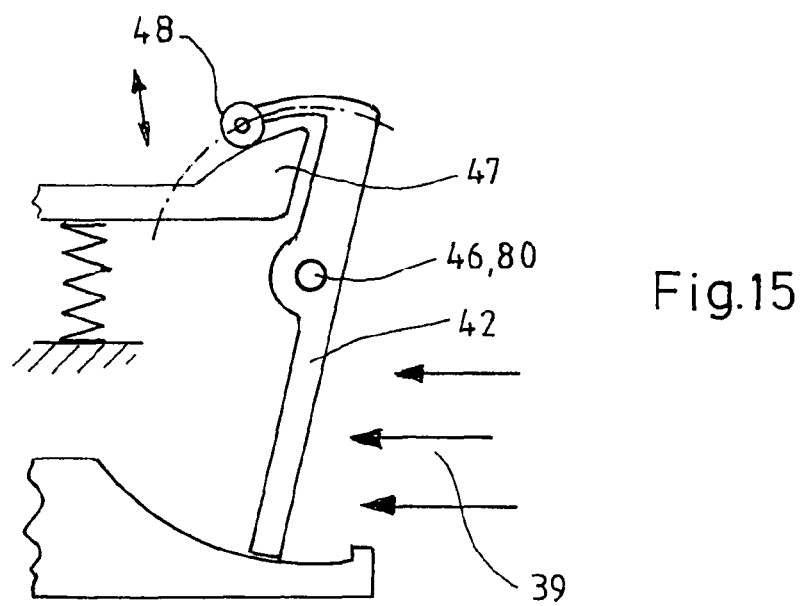
FIG. 15 shows a diagrammatic view showing the principle of another trigger arrangement of an inhalation device according to the invention.

The connection between the flap 42 and the thrust rod 43 can also be made in another suitable fashion, for example by means of a groove or opening into which an entrainment portion of the respective other part engages (FIG. 14). In an alternative embodiment which is diagrammatically shown in FIG. 15 the flap 42 is pivotable about an axis 46, wherein the axis is arranged at some distance from an end of the flap 42. The flap 42 has a claw which is pivotable together with the flap 42 about the axis 46 and which holds a spring-loaded securing element 47 and the contact face of which with the securing element 47 is formed by way of a sliding or rolling pairing, for example by a roller 48. The securing element 47 is in turn operatively connected to the device for inhalation-triggered automatic movement of the dosing slider 15, as already described hereinbefore, so that the device for inhalation-triggered automatic movement of the dosing slider 15 is released when the flap 42 is deflected out of its rest position by at least a predetermined amount by virtue of the inhalation flow on the part of the patient.

Figure 16:
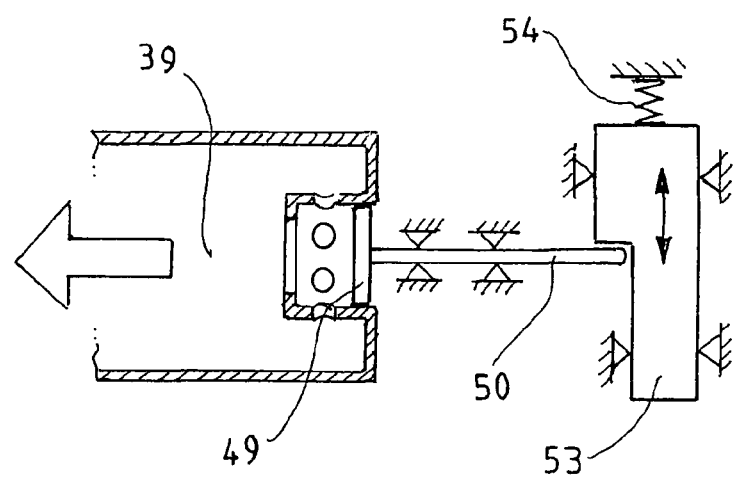
FIG. 16 shows a diagrammatic view showing the principle of a further trigger arrangement of an inhalation device according to the invention.

The trigger device can also have a piston 49 which is connected to the air passage 39 so that the face of the piston is acted upon by the reduced pressure which is applied by the patient. With such an arrangement the thrust rod is desirably formed by a piston rod 50. Desirably the piston in turn is of a comparatively large cross-sectional area in order reliably to release the device for inhalation-triggered automatic movement of the dosing slider 15 when the piston is deflected out of its rest position at least by a predetermined amount by the predetermined minimum airflow initiated by the patient in the air passage 39. Such an arrangement is diagrammatically shown in FIG. 16.

The device for inhalation-triggered automatic movement of the dosing slider 15 out of its filling position into the emptying position will be described in greater detail hereinafter with reference to the embodiment shown in FIGS. 12 and 13 of an inhaler 1 according to the invention. Desirably the dosing slider 15 includes entrainment projections 51, preferably at both sides transversely with respect to the direction of movement of the dosing slider 15. Those entrainment projections 51 of the dosing slider 15 co-operate with corresponding recesses of an actuating device for the dosing slider in the inhaler. In an advantageous embodiment those recesses are formed by two sliding guides 52 in a sliding guide carrier 53 as a drive element. The sliding guide carrier 53 is formed by a kind of frame which desirably embraces the lower region of the cartridge 3 on both sides (FIG. 12).

The sliding guide carrier 53 can assume a rest position, in the illustrated embodiment this involves an upper position. The sliding guide carrier 53 is held in that rest position by a biasing spring 54, wherein the biasing spring 54 is almost or completely relieved of stress when the sliding guide carrier 53 is in its rest position. The sliding guide carrier 53 can be moved into a readiness position, in the illustrated example in the lower position, against the force of the biasing spring 54. In that arrangement the sliding guide 52 includes a sliding guide portion 55 which is vertical in the position of use of the inhaler so that a relative movement is possible between the sliding guide carrier 53 and the entrainment projection 51 of the dosing slider 15 without the dosing slider 15 being moved out of its filling position.

Desirably the region of the sliding guide carrier 53 which includes the vertical sliding guide portion 55 is elastically deformable transversely with respect to the direction of movement of the sliding guide carrier 53. The vertical sliding guide portion 55 is of a depth which decreases in an upward direction and which in the upper region 56 of the vertical sliding guide portion forms a step, above which the sliding guide is again of the initial depth. When now the sliding guide carrier 53 is moved out of its rest position downwardly into its readiness position, the wedge effect of the upwardly decreasing depth of the vertical sliding guide portion 55 of the corresponding regions of the sliding guide carrier provide that the entrainment projections 51 of the dosing slider 15, which run in the vertical sliding guide portion 55, are elastically spread and snap back into their original position again as soon as the entrainment projections 51 have reached the upper region 56 of the vertical sliding guide portion 55 and have thus passed the step.

That arrangement is intended to ensure that, in a return movement of the sliding guide carrier 53 from its readiness position into its rest position, that is to say upwardly in the selected example, the entrainment projections 51 of the dosing slider 15 cannot run back in the vertical sliding guide portion 55.

The upper region 56 of the sliding guide 52 is connected to an oblique sliding guide portion 57 which is inclined with respect to the vertical sliding guide portion 55. When now the sliding guide carrier 53 moves out of the lower readiness position into the upper rest position, that is to say upwardly, the entrainment projections 51 of the dosing slider 15 are guided in the inclined sliding guide portion 57 so that, with a transmission relationship determined by the inclination of the inclined sliding guide portion 57 with respect to the direction of movement of the sliding guide carrier 53, the dosing slider 15 is entrained from its filling position into its emptying position in positively guided relationship. Disposed between a lower end of the inclined sliding guide portion 57 and the lower end of the vertical sliding guide portion 55 is a horizontal sliding guide portion 58 which connects the lower end of the inclined sliding guide portion 57 to the lower end of the vertical sliding guide portion 55. When the sliding guide carrier 53 reaches its upper rest position the dosing slider 15 can move with its entrainment projections 51 in the horizontal sliding guide portion 58 between its emptying position and its filling position. Desirably the dosing slider 15 is connected to a return spring 59 which draws the dosing slider 15 back into its filling position, when the upper rest position of the sliding guide carrier 53 is reached.

In its readiness position a portion 41 of the sliding guide carrier 53 covers over the dosing passage 38 above the location at which the dosing slider 15 briefly issues into the dosing passage 38. The sliding guide carrier therefore serves as a valve device 41 in order substantially to close the dosing passage 38 as long as the sliding guide carrier 53 is in its readiness position. As soon as the trigger device in the form of the flap 42 and the thrust rod 43 releases the sliding guide carrier 53 and therewith the valve device 41 and the sliding guide carrier 53 moves in a direction towards its rest position, the substantial part of the flow cross-section of the dosing passage 38 is opened. As a result, upon the beginning of an inhalation by a user of the inhalation device, a suction airflow is firstly built up in the air passage so that, upon inhalation-triggered opening of the dosing passage cross-section, there is already a suction airflow and the air does not have to be first accelerated and a reduced pressure built up. As the air passage 39 is substantially closed by the deflected flap 42, the substantial part of the airflow through the dosing passage 38 and in particular through the dosing cavity 17 of the dosing slider 15 now takes place during the time in which the dosing slider 15 is moved by the sliding guide carrier 53 into its emptying position. As a result, within a short period of time, it is possible to ensure complete emptying of the dosing cavity 17 and efficient introduction of the medicament in powder form into the lungs of a patient can be achieved.

The desirable embodiment is described with a sliding guide carrier 53 guided linearly in the housing 2. To avoid friction and jamming with unsuitable material pairing which can be caused by manufacture for example or can be caused by virtue of particular properties of the medicament, the drive element can also be in the form of a drive rocker 82. In order to achieve a movement which is as little curved as possible, it is desirable for the length of the rocker to be selected to be as great as possible. The possible rocker length however is greatly limited by the structural length of the inhaler 1. The effective rocker length can be markedly increased in relation to the actual available structural length by means of a multi-link arrangement as is known from the vehicle industry by the term Paralever. That however entails a corresponding increase in expenditure in terms of individual parts and assembly insofar as the links cannot be embodied by integral film hinges.

It is basically also conceivable for the dosing slider 15 to be connected directly to the flap 42 so that a movement of the flap 42 is transmitted directly to the dosing slider 15. It will be noted however that this requires complicated assembly procedures and the cartridge 3 cannot be so easily subsequently fitted into a completely pre-assembled inhaler 1.

Figure 22:
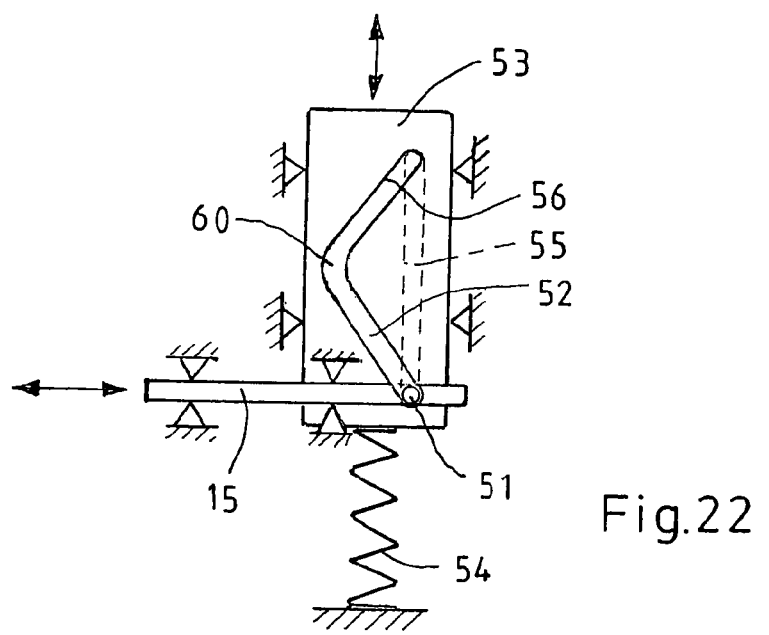
FIG. 22 shows a diagrammatic view showing the principle of an alternative sliding guide arrangement on a sliding guide carrier of an inhalation device according to the invention.
Figure 24:
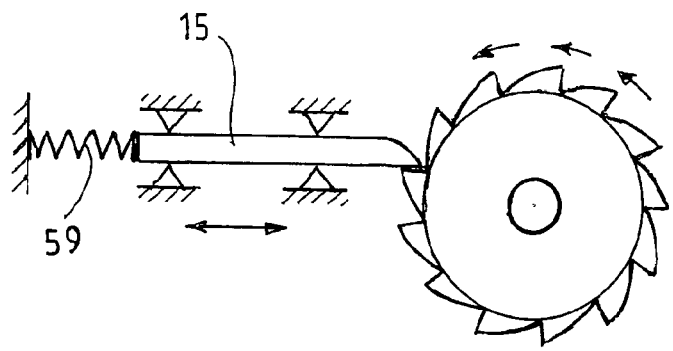
FIGS. 23 to 27 show diagrammatic views showing the principle of alternative arrangements for the actuation of the dosing slider on a sliding guide carrier as a drive element of an inhalation device according to the invention.
Figure 23:
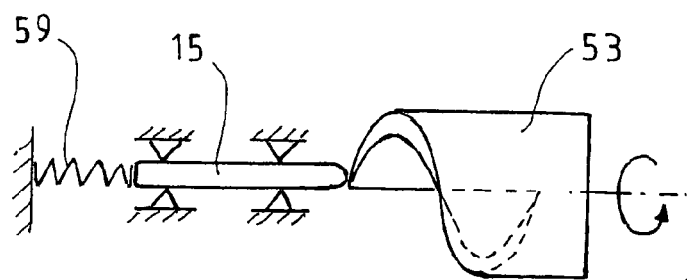
Figure 26:
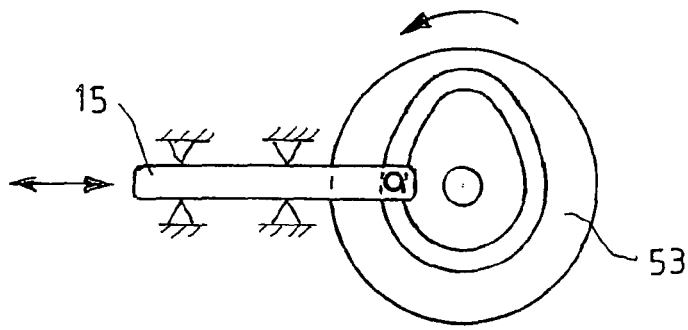
Figure 25:
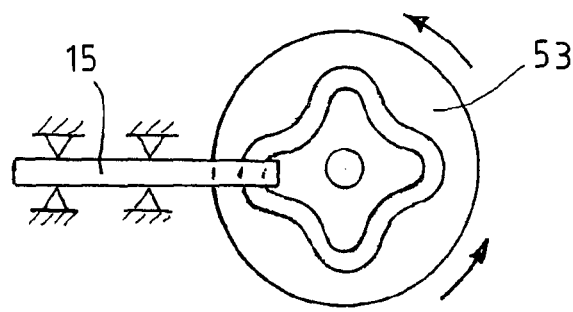
Figure 27:
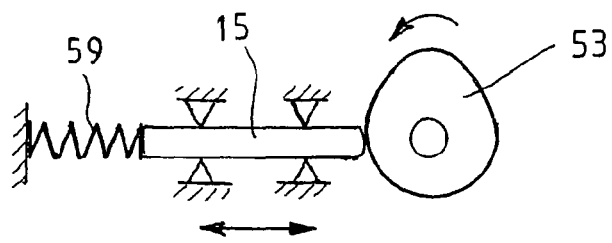

Instead of the described sliding guide configuration and return of the dosing slider 15 to its return position by way of a return spring 59, the sliding guide 52 of the sliding guide carrier 53, instead of the inclined sliding guide portion 57, can have a v-shaped sliding guide portion 60 which, for the entrainment projections 51 of the dosing slider 15, forms a positive guidance means for movement from its filling position into its emptying position and back into the filling position when the sliding guide carrier is moved out of the readiness position into the rest position (FIG. 22). The vertical sliding guide portion 55 is however also required in that case so that the sliding guide carrier 53 can be moved against the force of the biasing spring 54 into its readiness position without the dosing slider 15 leaving its filling position.

The sliding guides can also be in the form of cam portions in particular in conjunction with a dosing slider 15 which is loaded by a return spring 59. It is particularly desirable if the sliding guide portions are of a rectilinear configuration. However, to achieve a desired transmission ratio, for example to take account of the travel-dependent actuating force when moving the sliding guide carrier 53 out of its readiness position into the rest position, it may also be desirable for the sliding guides to be of a curved configuration, in particular eccentrically curved. In conjunction with a rotational movement it may also be desirable if the sliding guide or the cam portion is of a helical configuration.

The dosing slider 15 can also be moved from its filling position into the emptying position by a cyclically controlled cam or sliding guide wheel and can desirably be retracted by the return spring 59. In the case of a rotational arrangement the sliding guide carrier 53 can also have an eccentrically closed sliding guide and can positively guide the dosing slider 15 between the filling and emptying positions by way of the entrainment projections 51. In the case of a rotating sliding guide carrier 53 it is also possible to provide a cam arrangement, by way of which the dosing slider is moved out of the filling position into the emptying position and desirably retracted by the return spring 59. It is also possible to provide a corresponding arrangement with an eccentric cam disc. Corresponding arrangements are diagrammatically shown in FIGS. 23 to 27.

Direct coupling of the dosing slider 15 and the flap 42 or piston 59 for movement of the dosing slider out of the filling position into the emptying position, preferably in conjunction with the return spring 59, is also conceivable.

The actuating energy for the movement of the sliding guide carrier 53 out of its readiness position into the rest position is desirably afforded by way of the biasing spring 54. By means of suitable actuating devices a user of the inhaler 1 can store that necessary actuating energy in the device insofar as the sliding guide carrier 53 is moved from its rest position into its readiness position against the force of the biasing spring 54. That is described in greater detail hereinafter.

The sliding guide carrier 53, as part of the device for inhalation-triggered automatic movement of the dosing slider 15 out of its filling position into the emptying position, is arrested in its readiness position by the trigger device which has already been further described in greater detail herebefore. Desirably for that purpose the thrust rod 43 which has already been described in greater detail engages into a corresponding recess or projection of the sliding guide carrier 53 as soon as the sliding guide carrier 53 has reached its readiness position. The sliding guide carrier 53 can only return to its rest position when, by virtue of a sufficiently high level of inhalation suction flow, the flap 42 is deflected and the thrust rod 43 is moved sufficiently far that it comes out of engagement with the sliding guide carrier 53 and the sliding guide carrier 53 can be moved by the force of the biasing spring 54 out of its readiness position into the rest position.

Desirably the biasing spring 54 is in the form of a leaf spring (see FIG. 56) or a shaped spring. Such a spring can be easily produced, it can be of a contour which is adapted to the space circumstances in the inhaler and it can possibly be formed by a suitable plastic material which is also fibre-reinforced, and can be in one piece with other components of the inhaler, for example by injection moulding. Such a one-part configuration together with the sliding guide carrier 53 or a part of the housing 2 would be desirable. In the same fashion the return spring 59 for the dosing slider 15 can also be in the form of a leaf spring or shaped spring.

When constricted lateral space circumstances are involved, it may also be desirable if the biasing spring 54 and/or the return spring 59 is in the form of a coil spring. In particular that structural configuration is appropriate for the return spring 59. It may also be desirable, in particular in conjunction with a rotationally actuated drive rocker 82, if the biasing spring 54 and/or the return spring 59 is a spiral spring or a torsion spring. Particularly for the return spring 59 but also for the biasing spring 54, it may also be desirable if it is an elastically deformable shaped body. For that purpose, for example in relation to the return spring 59, it is appropriate to injection-mould on the dosing slider 15 such a shaped body, for example in the form of a suitable thermoplastic elastomer, which can then serve as a traction spring. It may also be desirable for the biasing spring 54 if it is injection-moulded for example in the form of an elastically deformable shaped body on the sliding guide carrier 53 or the bottom of the housing 2.

In particular for the biasing spring 54 it is also appropriate for that spring to be formed by a compressed air storage means. Here for example a part of the sliding guide carrier 53 can be in the form of a piston which engages into a hermetically closed cylinder so that the volume of air in the cylinder is compressed when the sliding guide carrier 53 is moved from its rest position into the readiness position. As soon as the sliding guide carrier 53 is released by the trigger device the volume of air in the cylinder can expand and thus drive the sliding guide carrier 53 into its rest position.

In order to achieve uniform actuating forces for the dosing slider 15 it may be desirable for the biasing spring 54 to have a non-linear spring characteristic.

Figure 32:
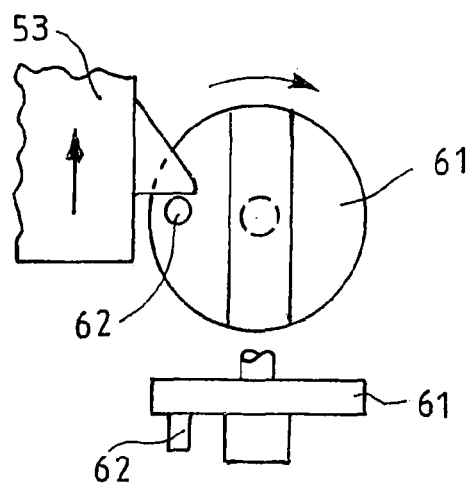

In accordance with the invention there are a number of possible options for operating devices, by which a user of the inhaler 1 can move the sliding guide carrier 53 from its rest position into its readiness position against the force of the biasing spring 54. One possible option is for the biasing force to be applied by means of a rotary knob 61 coupled to an entrainment portion 62, by way of which the sliding guide carrier 53 is displaced out of its rest position into the readiness position when the rotary knob 61 is turned. The actuating force can be altered, with the biasing force of the biasing spring 54 remaining the same, by the spacing of the entrainment portion 62 from the axis of rotation of the knob 61. It will be appreciated however that limitations in terms of structural space are to be taken into consideration. Such an arrangement is shown in the diagrammatic view in FIG. 32.

Figure 33:
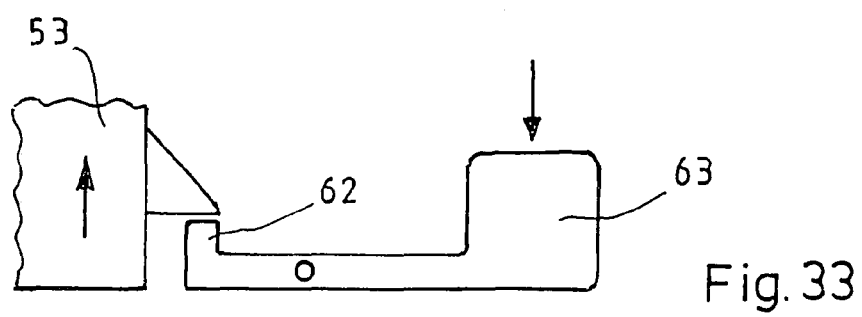

Actuation of the sliding guide carrier can also be effected by way of an actuating button 63 which can act directly with a translatory movement on the sliding guide carrier 53 or which can act on the sliding guide carrier 53 by way of rotary pivot point. In the last-mentioned variant the actuating force required with a given biasing force of the biasing spring 54 can be set by adjustment of the lever lengths. It will be appreciated that such an arrangement also involves a limitation due to the structural space in the housing 2 of the inhaler 1. Such a view is shown in principle in FIG. 33.

Figure 34:
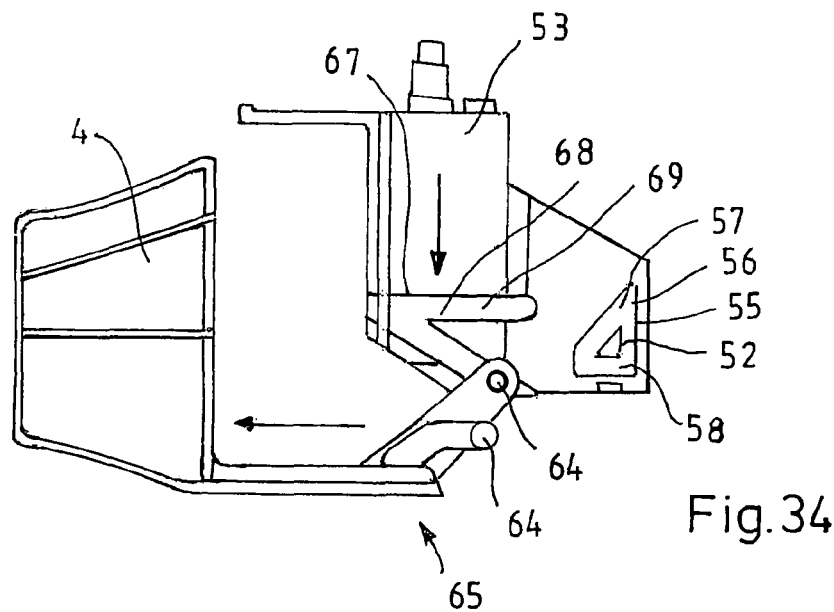

It is particularly preferred in accordance with the invention however for actuation of the sliding guide carrier 53 from its rest position into the readiness position to be coupled to the movement of the closure cap 4 out of the closure position into the readiness position. As already mentioned the protective or closure cap 4 is non-losably connected to the inhalation device. Desirably the closure cap 4 includes two pairs of entrainment portions 64 which are arranged at the rearward portion 65 of the closure cap 4. In the embodiment of an inhaler 1 according to the invention as shown in FIGS. 12 and 13 a pair of those entrainment portions 64 run in a sliding guide 66 in the housing 2. That firstly makes it possible for the closure cap to be guided in the longitudinal direction from the front side 8 of the inhaler 1 until the closure cap 4 can be pivoted downwardly past the mouthpiece 5. In that case longitudinal mobility of the closure cap 4 with respect to the housing 2 is achieved by way of the preferably linear sliding guide 66. A further pair of entrainment portions 64 co-operate with an actuating sliding guide 67, which is complementary thereto, in the sliding guide carrier 53. In that arrangement the actuating sliding guide 67 includes an inclined sliding guide portion which is so inclined that it falls away rearwardly, as viewed from the front side 8 of the inhaler, and is open downwardly. When the sliding guide carrier is in its rest position and the closure cap is in its closure position the entrainment portion 64 engages into the rear lower end of the inclined sliding guide portion. If now the closure cap 4 is pulled forwardly in order to be pivotable past the mouthpiece 5, the sliding guide carrier 53 is actuated by the longitudinal movement of the closure cap and therewith the pair of entrainment portions 64, by way of the inclined sliding guide portion 68, from its rest position into the readiness position downwardly against the force of the biasing spring 54. The closure cap 4 can now be pivoted into its operative position and the mouthpiece 5 is accessible to the patient to carry out an inhalation process. When inhalation is successfully effected the sliding guide carrier 53 moves back into its rest position. The closure cap can now be pivoted upwardly and pushed rearwardly into the inhaler. In that case the entrainment portions 64 come into engagement again with the rear lower end of the inclined sliding guide portion 68 of the sliding guide carrier 53. That can be seen from the diagrammatic view in FIG. 34.

Figure 35:
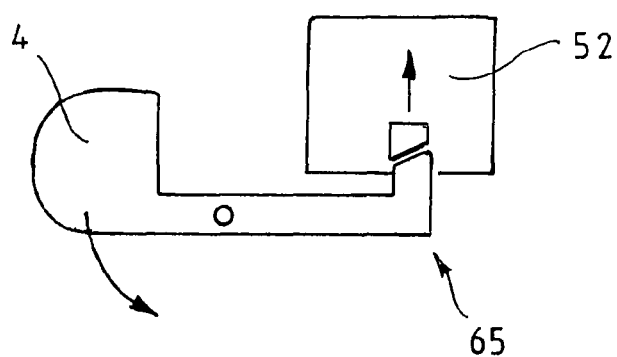

The actuating sliding guide 67 in the sliding guide carrier 53 desirably also has a second sliding guide portion 69 which extends substantially horizontally, in particular parallel to the sliding guide 66 in the housing 2. That second sliding guide portion 69 does not have a direct function but only serves to afford the patient the possible option of being able to move the closure cap 4 into the closure position again without successful inhalation having been effected. With that configuration the sliding guide carrier 53 is still in its lower readiness position and without the second sliding guide portion 69 the closure cap 4 could not be pushed rearwardly, with the entrainment portions 64. Such a functional extent is particularly desirable to provide that for example a pharmacist can demonstrate handling of the inhalation device without a dose having to be directly taken therefrom. As a dose could only be inhaled by an adequate inhalation airflow, that would otherwise have the result that a patient would have to inhale a dose of a medicament, at a time which is possibly not prescribed by the physician. Desirably, the second sliding guide portion 69 is closed at its end so that, when the sliding guide carrier 53 is in its readiness position and the closure cap 4 in the closure position, the sliding guide carrier 53, in addition to being securely held in its readiness position by the thrust rod 43 of the trigger device, is additionally secured in its readiness position by the entrainment portions 64 of the closure cap 4 so that, even for example when an inhaler 1 in the stressed condition is dropped, the entrainment portions 64 of the closure cap 4, by way of the second or complementary sliding guide portion 69, reliably prevent delivery of a dose of the drug into the dosing passage. Desirably the actuating or complementary sliding guide 67 is inclined through an angle α of between 15° and 45° with respect to the sliding guide 66 in the form of a guide means, in the housing 2. For adaptation of the actuating forces to the travel-dependent biasing force of the biasing spring 54, it may also be desirable if the complementary or actuating sliding guide 67 extends in a non-rectilinear configuration. As an alternative to the arrangement involving entrainment portions 64 and the actuating or complementary sliding guide 67, the closure cap 4 can also have a pressure lever, by way of which a sliding guide carrier 53 can be directly or indirectly moved into its readiness position. That is appropriate in particular when, in comparison with the arrangement described as the preferred one, the readiness position of the sliding guide carrier 53 is disposed above the rest position. Such an arrangement is diagrammatically shown in FIG. 35.

Figure 36:
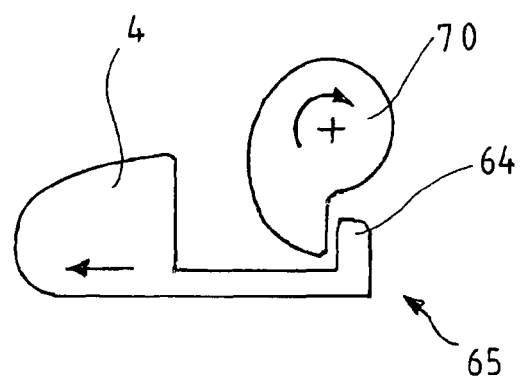

It may however also desirable for an eccentric disc to be actuated by way of the entrainment portions 64 on the closure cap 4, in which case the rectilinear actuation of the closure cap is converted into a rotary movement about the fixing axis of the eccentric disc 70 and the sliding guide carrier 53 is moved by way of the eccentric disc into its readiness position against the force of the biasing spring 54. That is appropriate in particular in conjunction with a biasing spring 54 in the form of a coil spring or a torsion spring. Such an arrangement is diagrammatically shown in FIG. 36.

Figure 2:
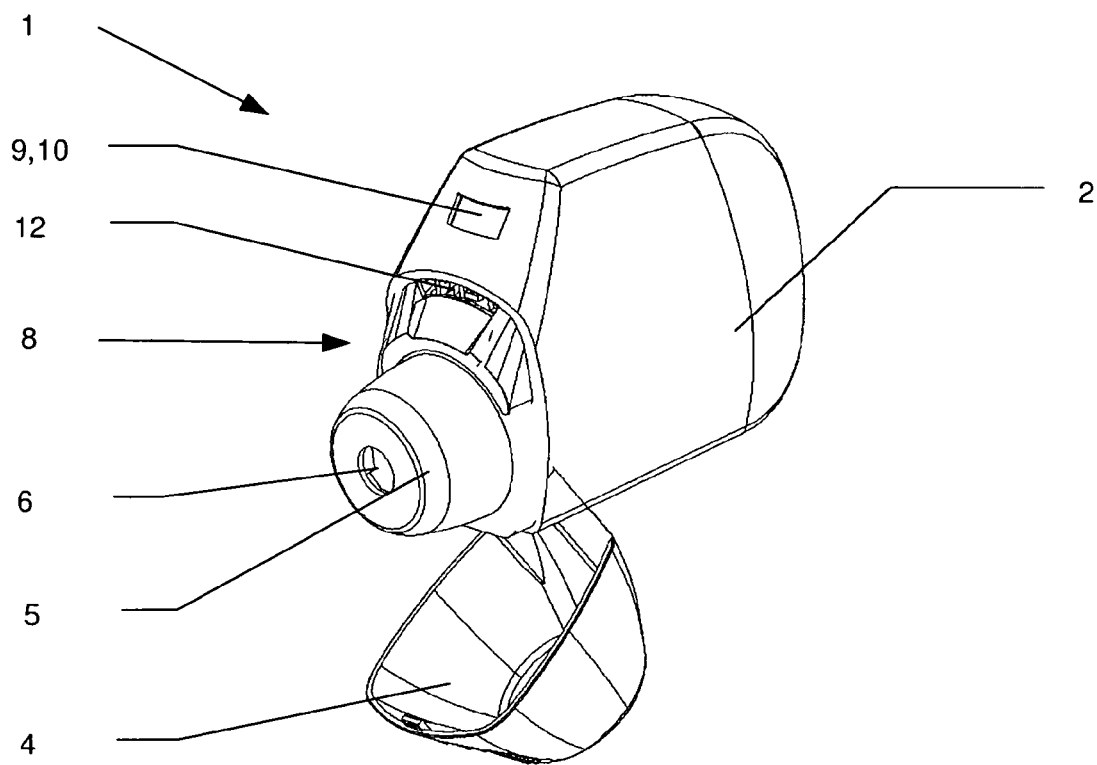
FIG. 2 shows a perspective view of an embodiment of an inhalation device according to the invention with the closure cap opened.
Figure 17:
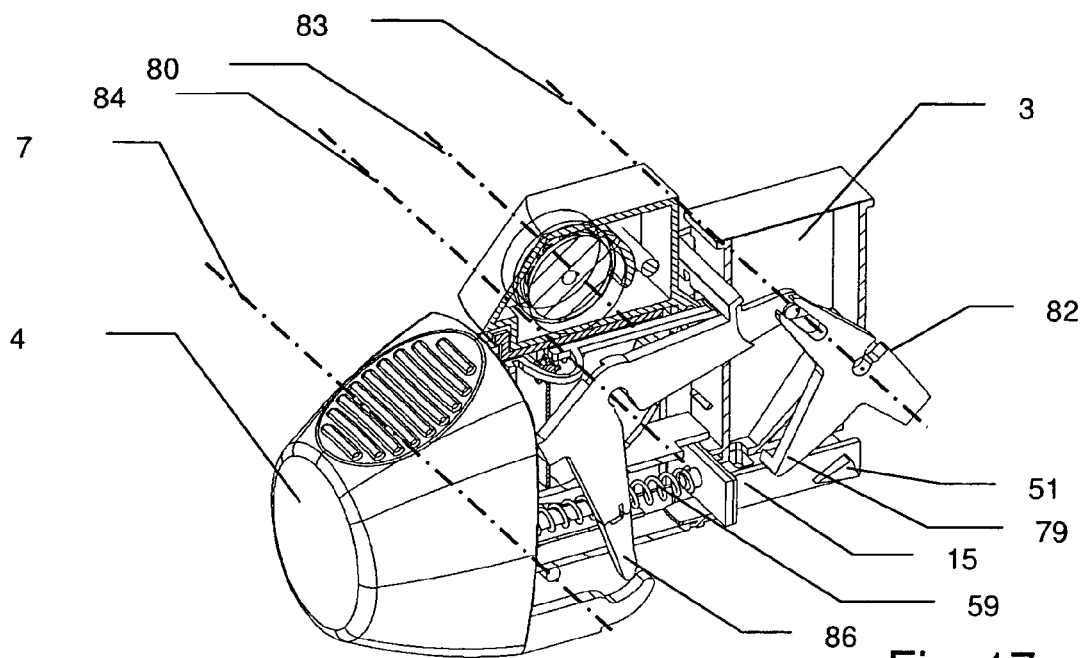
FIG. 17 shows a perspective view of an embodiment of an inhalation device according to the invention with the closure cap in the closure position with the housing removed, with further components being partially omitted.
Figure 18:
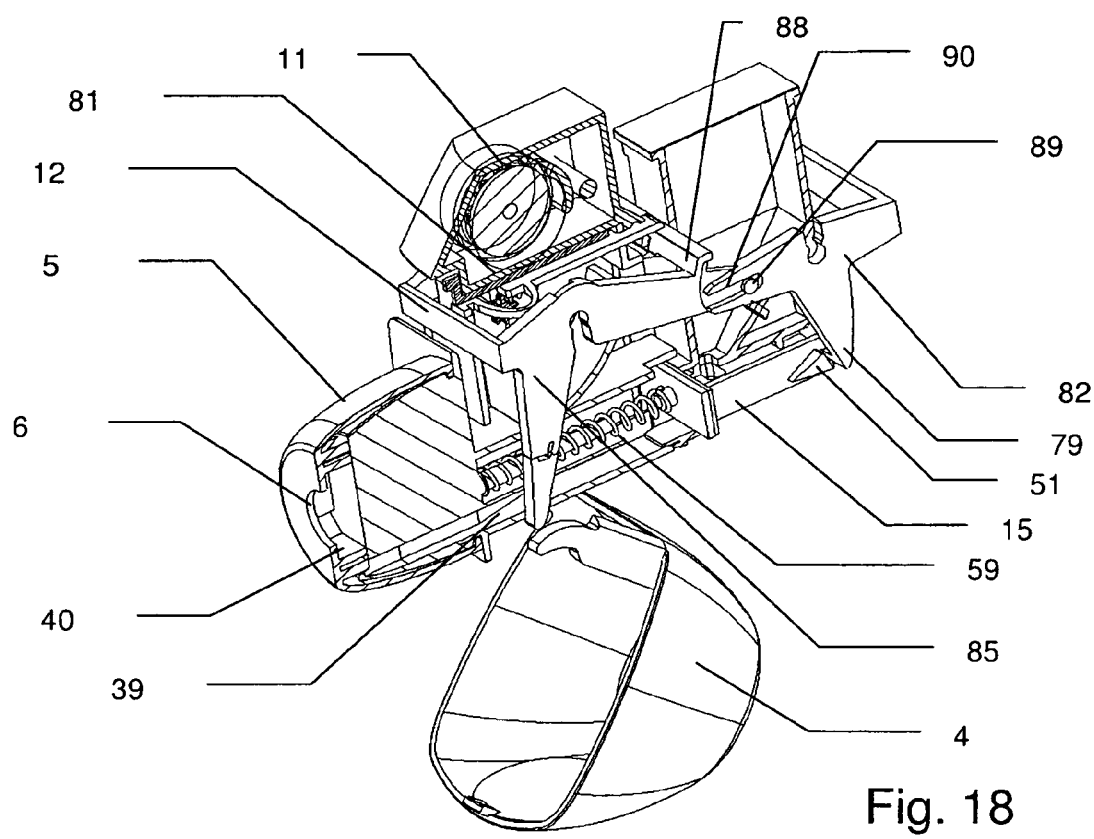
FIG. 18 shows a perspective view of an embodiment of an inhalation device according to the invention with the closure cap in the operative position with the housing removed, with further components being partially omitted.

In another particularly preferred embodiment of an inhaler 1 according to the invention the biasing of the dosing mechanism is achieved by a purely rotational movement of the protective cap 4. That embodiment can be particularly clearly seen in FIGS. 1, 2, 11, 17 and 18. In that respect FIGS. 1 and 17 show the inhaler 1 with its closure cap 4 in its closure position. For the sake of clarity the view in FIG. 17 omits the housing 2 and some further parts of the inhaler 1. FIGS. 2 and 18 show the inhaler 1 with its closure cap 4 in its operative position, that is to say with the protective cap 4 open. For the sake of simplicity of the drawing the housing 2 and some further parts of the inhaler 1 are also omitted from FIG. 18. FIG. 17 shows the arrangement of the individual parts of the inhaler 1 with the dosing mechanism in the released condition, that is to say the biasing spring 54 (not shown in this Figure) is relieved of stress and the drive element in the form of the drive rocker 82 is in its rest position. FIG. 18 shows the arrangement of the individual parts of the inhaler 1 with the dosing mechanism stressed by opening of the closure cap 4, that is to say the biasing spring 54 (not shown in this Figure) is stressed and the drive element in the form of the drive rocker 82 is in its readiness position. In that operative condition of the inhaler 1 inhalation can be effected by the patient at any time, by the patient drawing in air through the mouthpiece and triggering a dosing operation when a trigger airflow is exceeded, as described hereinbefore.

The closure cap 4 has at least one entrainment portion 64 and a transmission rocker 85 which is operatively connected to the drive rocker 82 pivotable about a first pivot axis 83, the transmission rocker 85 being pivotable about a second pivot axis 84, while the closure cap is pivotable out of the closure position into the operative position about the (third) axis 7. The at least one entrainment portion 64 of the closure cap 4 engages behind at least one operative end 86 of the transmission rocker 85 upon opening of the closure cap 4 so that the drive rocker 82 is movable by the movement of the closure cap 4 about the third axis 7 out of the closure position into the operative position by way of the transmission rocker 85 against the force of the biasing spring 54, out of its rest position into its readiness position.

The drive rocker 82 and the transmission rocker 85 are in engagement with each other in such a way that their rotation about the first and second pivot axes 83 and 84 takes place in opposite relationship. As a result the moments of inertia upon triggering of drug delivery substantially cancel each other out so that the patient is only slightly adversely affected by return forces which are perceived as a knock and corresponding noise. Advantageously in that respect the drive rocker 82 and the transmission rocker 85 are of such a design configuration and dimensions that the moment of inertia of the drive rocker 82 about the first pivot axis 83 and the moment of inertia of the transmission rocker 85 about the second pivot axis 84 are of approximately equal magnitude.

Advantageously the at least one operative end 86 of the transmission rocker 85 is so designed that, upon actuation of the closure cap 4 from the closure position into the operative position about the third axis 7 the operative end 86 is engaged in positively locking relationship by the at least one entrainment portion 64 of the closure cap 4 and the moment applied by the at least one entrainment portion 64 is transmitted to the transmission rocker 85 if the dosing mechanism is not already prestressed. Upon the return of the closure cap 4 from the operative position into the closure position and of the transmission rocker 85 which is returned to the rest position by triggering of a dosing operation, the operative end 86 elastically evades the entrainment portion 64. For that purpose the operative end 86 is connected to the rest of the transmission rocker 85 by way of a film hinge 87 arranged at the end more remote from the mouthpiece 5. In that way it is possible for the closure cap to be moved into a protecting condition over the mouthpiece again even when a drug dose has not yet been taken.

Desirably the transmission rocker 85 is of a symmetrical configuration relative to the longitudinal central plane of the inhaler 1 and includes two rocker elements which are arranged on both longitudinal sides of the inhalation device pivotably about the second pivot axis 84 and are connected together with at least one yoke 86, wherein the thrust rod 43 holds the transmission rocker 85 in the prestressed position of the drive rocker 82 by engagement with the yoke 88 when the flap 42 is in its rest position and the thrust rod 43 clears the travel of the yoke 88 and therewith the transmission rocker 85 when the flap 43 is deflected out of its rest position at least by a predetermined amount so that the transmission rocker 85 and the drive rocker 82 are movable from their readiness position into their rest position by the biasing spring 54.

Figure 21:
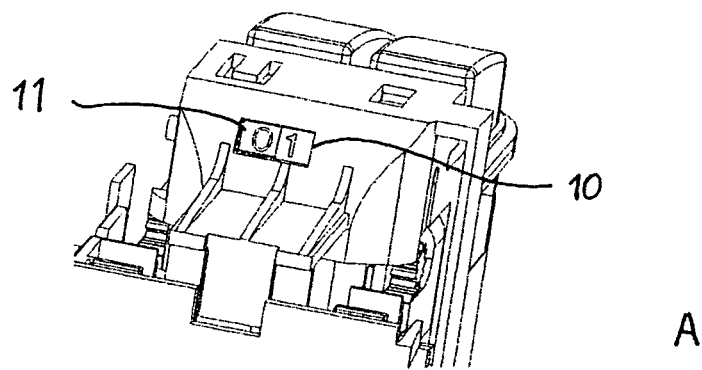
FIG. 21 shows an enlarged view of a part of the embodiment of an inhalation device of FIG. 19 with the housing removed.
Figure 21:
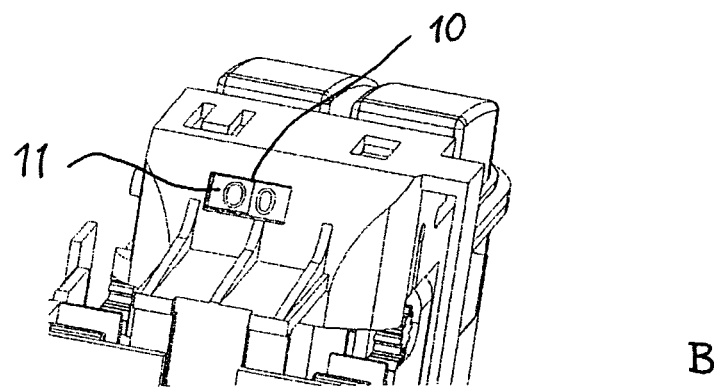
Figure 21:
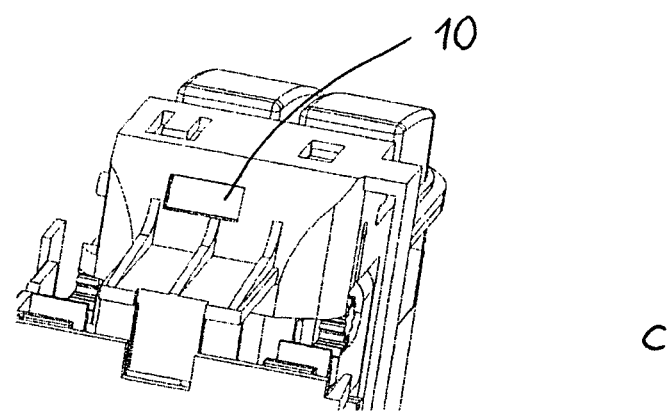
Figure 55:
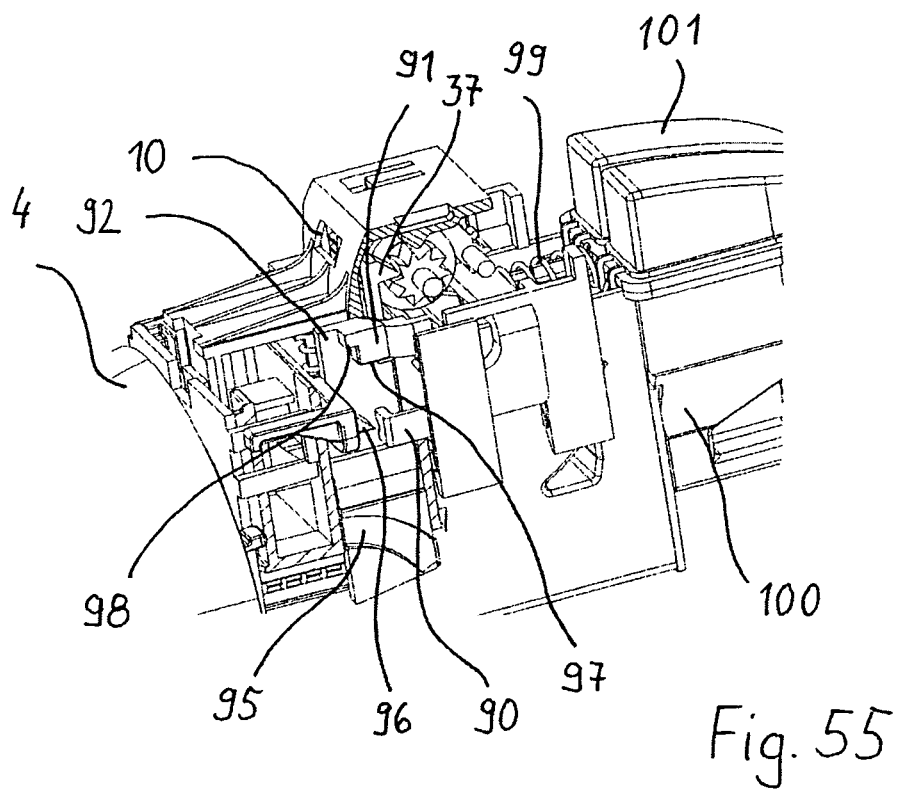
FIG. 55 shows an enlarged detailed sectional view of actuation of a counting device according to the invention with the embodiment of the inhalation device from FIGS. 19-21, 28-31 and 48 to 54.

As already mentioned hereinbefore an inhaler 1 according to the invention includes a counting device 11 for accurate-dose representation preferably of the number of doses which can still be taken from the stored drug supply, by way of the display 10. For that purpose the counting device 11 can advantageously be formed by a known two-digit or three-digit drum counter. Such drum counters can be inexpensively made from plastic material and can therefore also be easily disposed of with the inhaler 1 after the expiry of the working life thereof. In comparison with an electronic counter which has already been proposed for such purposes, this has the advantage that the inhaler 1 does not have to be broken up as an expensive and complicated procedure after the expiry of its useful life so that electronic components can be sent separately for specific processing and disposal in accordance with the prescribed procedure. The drum counter can in the usual fashion be driven by way of a stepping switching mechanism 37 by the sliding guide carrier and is advanced by 1 with each stroke movement performed by the sliding guide carrier 53, see FIG. 55. Advantageously in that respect the arrangement is such that the counting device counts downwards to represent the doses that still remain. The starting value of the display 10 must therefore be set to a value corresponding to the filling amount of doses of the drug in the storage chamber 13 of the cartridge 3 less a safety value to take account of fluctuations in the filling amount or possible settling effects in the drug powder. After a predetermined number of doses have been counted down, an index is displayed, for example in the form of a coloured emphasis which indicates a consumed supply of drug. A sequence of the last three actuations of such an inhaler is depicted in FIG. 21, steps A, B and C.

Furthermore the preferred inhaler 1 according to the invention is provided with a locking device which, upon the attainment of a predetermined number of delivered doses, blocks the closure cap 4 in such a way that the closure cap 4 is no longer movable into the closure position. The locking device includes a locking stirrup 71 which comprises two limbs 72 connected by a yoke 73. The yoke 73 of the locking stirrup 71 is pressed against the drum counter by a spring 74, preferably a leaf or shaped spring, see FIG. 12.

Desirably the drum counter is of such a design that each drum has a groove 75 so that the grooves 75 of the drums are aligned when a displayed counter state 000 is reached. The locking stirrup 71 is arranged in such a way that the yoke 73 is engaged by the spring 74 into the aligned grooves 75 of the drums and thus the entire locking stirrup 71 is displaced by a distance. In that case the ends of the limbs 72, which are not connected by the yoke 73, engage into the path of movement of the entrainment portions 64 of the closure cap 4 and/or into the sliding guide of the housing 2 so that the entrainment portions 64 can no longer be displaced along the sliding guide 66 and thus the closure cap 4 can no longer be moved into the closure position. Desirably the engagement by the limbs 72 of the locking stirrup 71 is so far removed from the closure position of the closure cap 4 that the closure cap 4 projects from the housing 2 so markedly detectably (FIGS. 11, 54) that even a less well-informed patient clearly perceives that and knows that the stored supply of drug in that inhaler 1 is consumed.

Finally, it is possible to mount to the yoke 73 of the locking device 71 a signal plate 76 so that, upon blocking engagement of the locking device 71 or upon engagement of the yoke 73 into the grooves 75, the signal plate 76 is pivoted in front of the display 10. The signal plate 76 can carry a signal colour and/or can be labelled with an item of text "EMPTY" or a similar item of information which unmistakably indicates to the patients that the stored supply of drug in that inhaler 1 has been exhausted and no further dose is to be obtained from that inhaler 1. Instead of a drum counter it is also possible to use a strip running mechanism as the display 10. Instead of the grooves 75, a hole can be provided in the strip at a suitable location so that a pin or the like on the yoke 73 can engage into the hole in the strip in order to actuate the locking device 71 and the signal plate 76.

Figure 11:
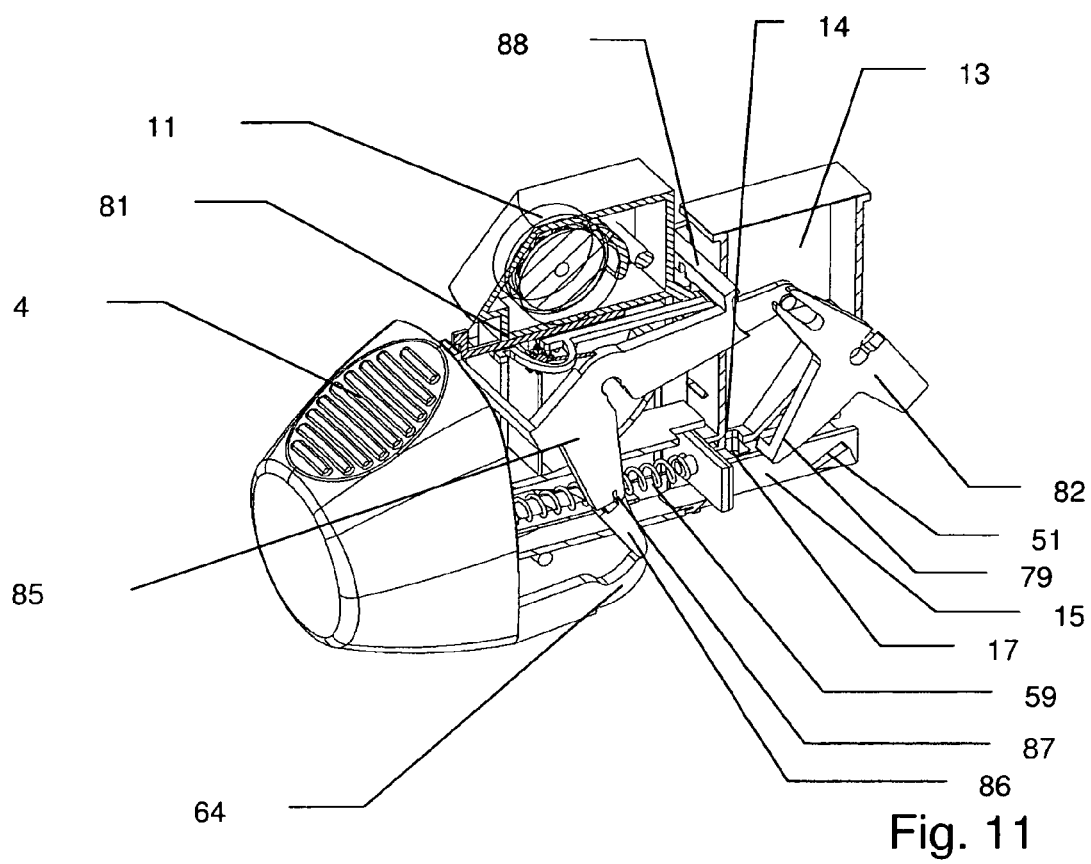
FIG. 11 shows a perspective view of an embodiment of an inhalation device according to the invention after engagement of the locking device with the housing removed, with further components being partially omitted.

In the particularly preferred embodiment of an inhaler 1 as shown in FIGS. 11 and 17 the locking device has a spring lever blocking rod 81 which, upon the attainment of a predetermined number of delivered doses, is movable from a rest position (FIGS. 17, 18) into a blocking position and which in its blocking position engages in blocking relationship into the path of the closure cap 4 so that the closure cap 4 can no longer be moved into the closure position (FIG. 11). That arrangement provides for both particularly clear signaling and also prevents (futile) further use of the inhalation device 1 and thus unwanted under-dosing. In that arrangement the blocking rod 81 can be coupled in spring-loaded relationship to the counting device 11, as described hereinbefore, and is arrested in its blocking position for example by a locking pawl (not shown) or a latching tooth so that the blocking rod 81 cannot be pushed back into its rest position against the force of its actuating spring. That ensures that the blocking condition cannot be undone without destroying component parts of the inhaler 1. In that case the blocking rod 81 can be designed with a signal colour so that the blocked condition is more clearly perceptible.

For the particular situation of use of an inhaler 1 according to the invention for emergency medicine the locking element in the form of the locking stirrup 71 or the blocking rod 81 can be omitted in order to comply with corresponding regulations. More specifically the view is sometimes taken that, in this specific situation of use, the possible option of still being able if necessary to inhale residual amounts from the storage chamber 13, even if the nominal number of doses has already been taken, should have priority over protection from under-dosing when there is an insufficient stored supply of drug, such protection being ensured by the blocking action.

The procedure involved in a usual process of using a preferred embodiment of an inhaler 1 according to the invention is shown in FIGS. 37 to 47. The illustrated embodiment and the view represented correspond to the embodiment in FIGS. 1, 2, 11, 17 and 18. For the sake of better visibility of the different positions of the components therefore the references from FIGS. 11, 17 and 18 have not been repeated here.

Figure 37:
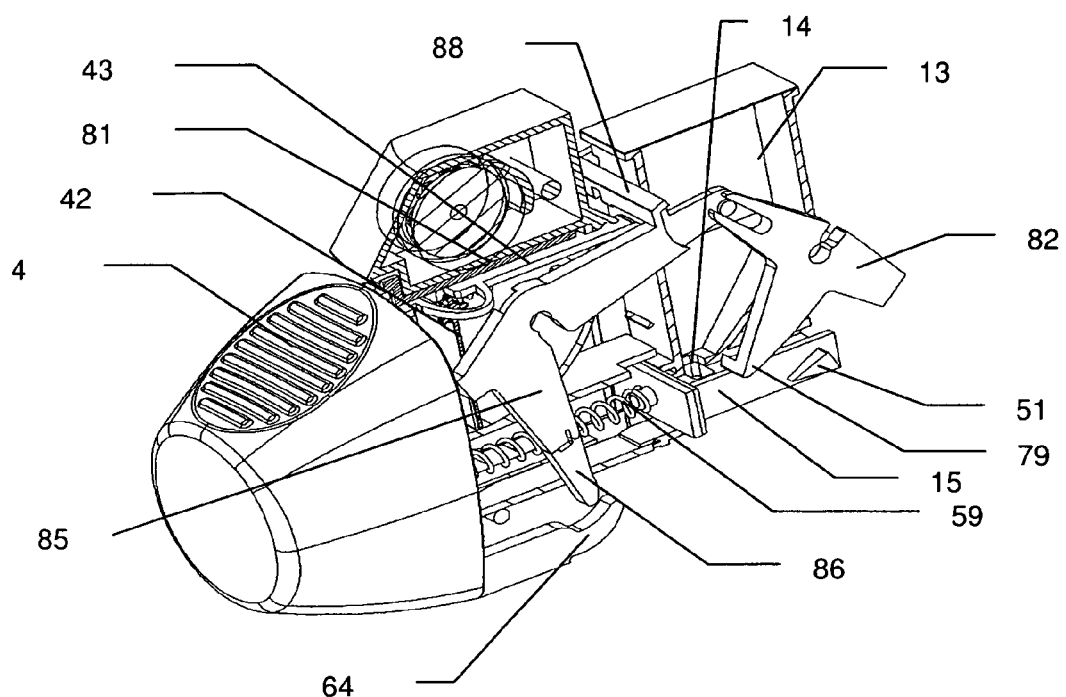
FIGS. 37 to 47 show the inhaler from FIGS. 11, 17 and 18 in various operating conditions in a usual use procedure.

FIG. 37 shows the inhaler 1 with closed closure cap 4 and with the dosing mechanism in the relieved condition, that is to say the biasing spring 54 (not shown in this Figure) is relieved of stress and the drive element in the form of the drive rocker 82 is in its rest position.

Figure 38:
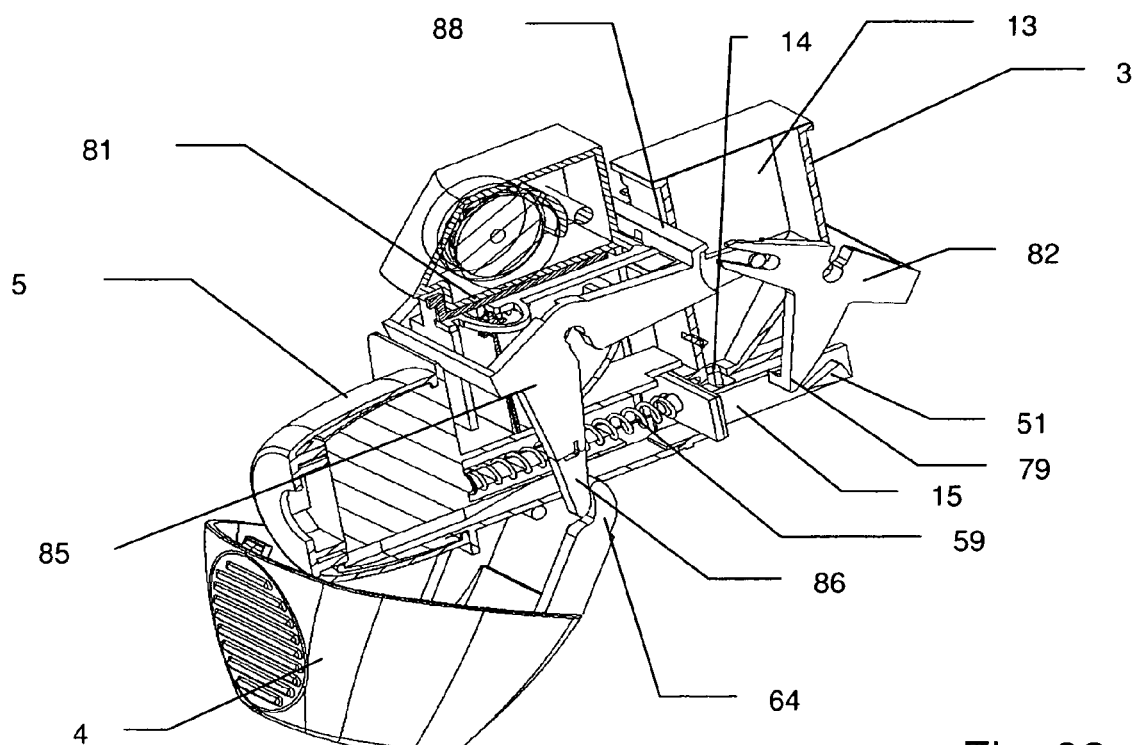
Figure 39:
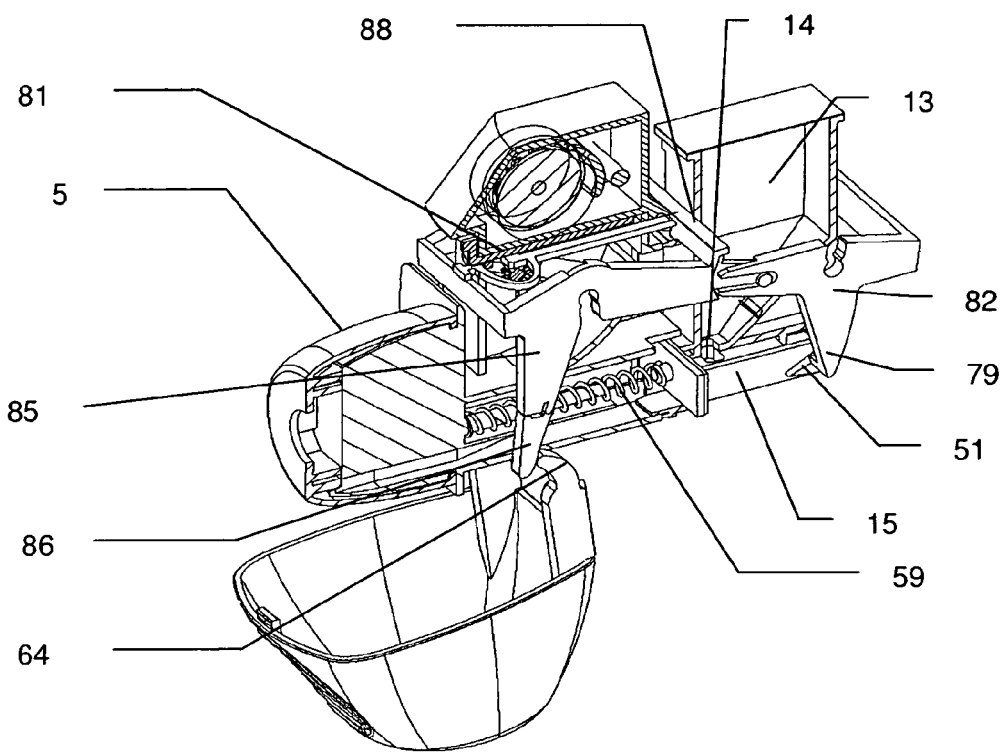
Figure 56:
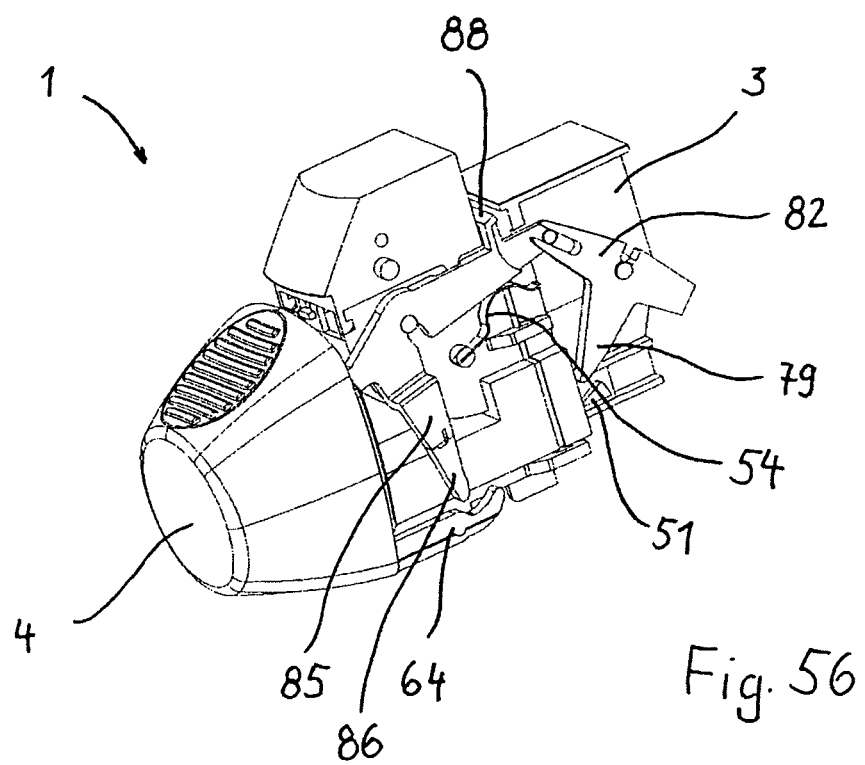
FIG. 56 is a perspective view of the embodiment of an inhalation device according to the invention as shown in FIGS. 11, 17 and 18.

FIG. 38 shows the inhaler 1 during a first phase of pivoting the closure cap 4 open. In the pivotal movement of the closure cap 4 about the (third) pivot axis 7 entrainment portions 64 of the closure cap 4 engage behind the operative end 86 of the transmission rocker 85 and thereby pivot the transmission rocker 85 about the second pivot axis 84. The transmission rocker 85 engages with entrainment portions 89 into an opening 90 in the drive rocker 82 and entrains it in the pivotal movement of the transmission rocker 85 so that the drive rocker 82 is pivoted about the first pivot axis 83 against the force of the biasing spring 54 (FIG. 56). Arms 79 of the drive rocker 82 move relative to the entrainment projections 51 of the dosing slider 15, which are in the form of a ramp in the direction of movement of the dosing slider 15, so that the arms 79 are spread open by the ramp. As soon as the arms 79 have passed the ramp of the entrainment projections 51 of the dosing slider 15, they snap together again (FIG. 39) and can subsequently entrain the dosing slider 15 in movement in the opposite direction.

When the operative position of the closure cap 4 is reached (see FIG. 18) the dosing mechanism is stressed and the transmission rocker 85 and the drive rocker 82 are secured in the biased readiness position by the thrust rod 43.

Figure 40:
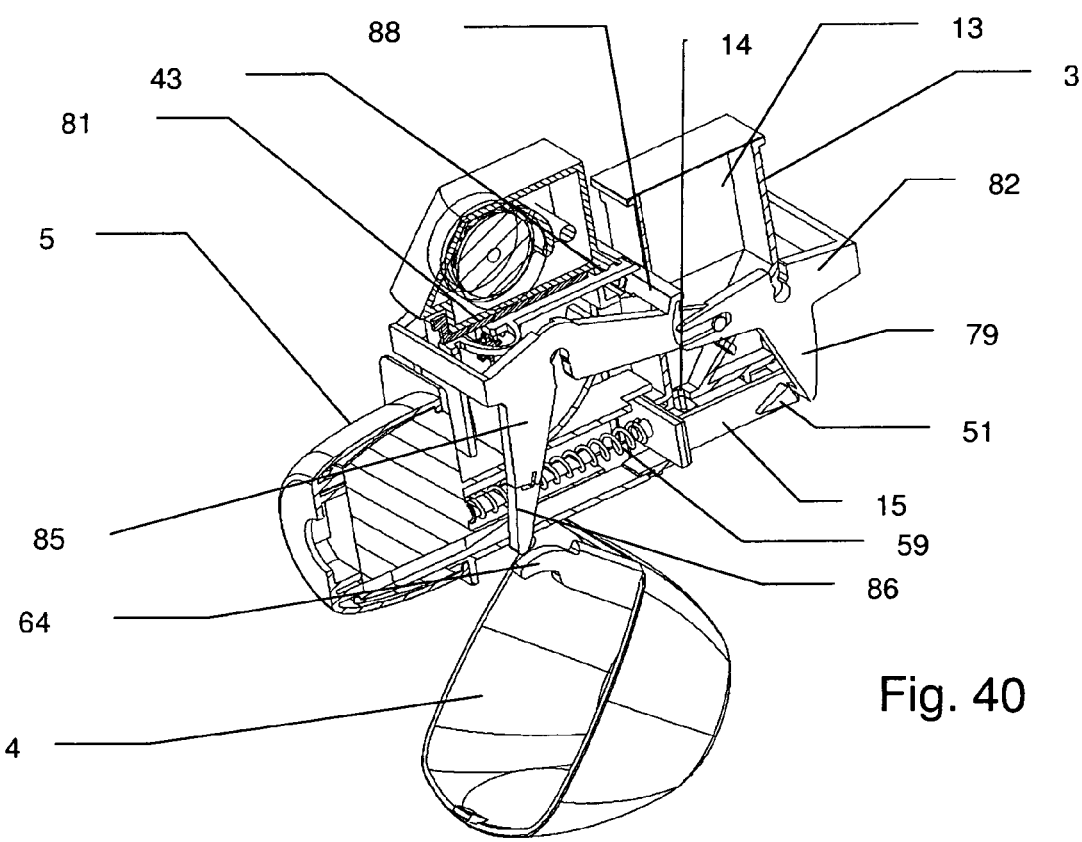

When now a patient sucks an airflow through the inhaler 1 the flap 42 is deflected out of its rest position (FIG. 40). In that operative condition the dosing slider 15 is still in its filling position and the cartridge 3 is sealed off with respect to the ambient atmosphere.

Figure 41:
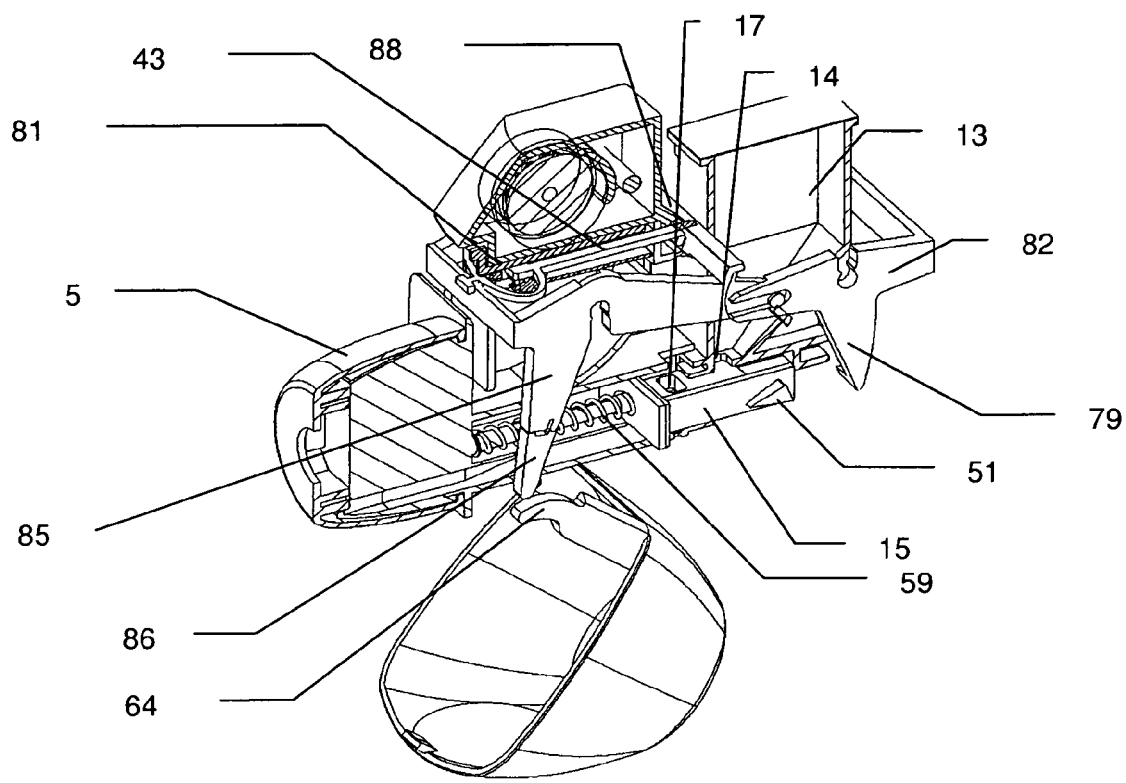

When the predetermined minimum airflow in the air passage 39 is exceeded by the patient breathing in and thus the flap 42 is deflected beyond the trigger threshold, as shown in FIG. 41, the thrust rod 43 is pulled forward by the movement of the flap 42 beyond the trigger threshold to such an extent that it comes out of engagement with the yoke 88 of the transmission rocker 85 and thus the automatic movement of the dosing mechanism is enabled. Driven by the force of the biased biasing spring 54 the drive rocker 82 and the transmission rocker 85 pivot back in the direction of the rest position. In that case the arms 79 of the drive rocker 82 push the dosing slider 15 out of its filling position into its emptying position by way of the entrainment projections 51 of the dosing slider 15 so that the drug powder is discharged out of the dosing cavity 17 of the dosing slider 15 by means of the airflow produced by the patient and finally discharged through the inhalation opening 6 of the mouthpiece 5.

Figure 42:
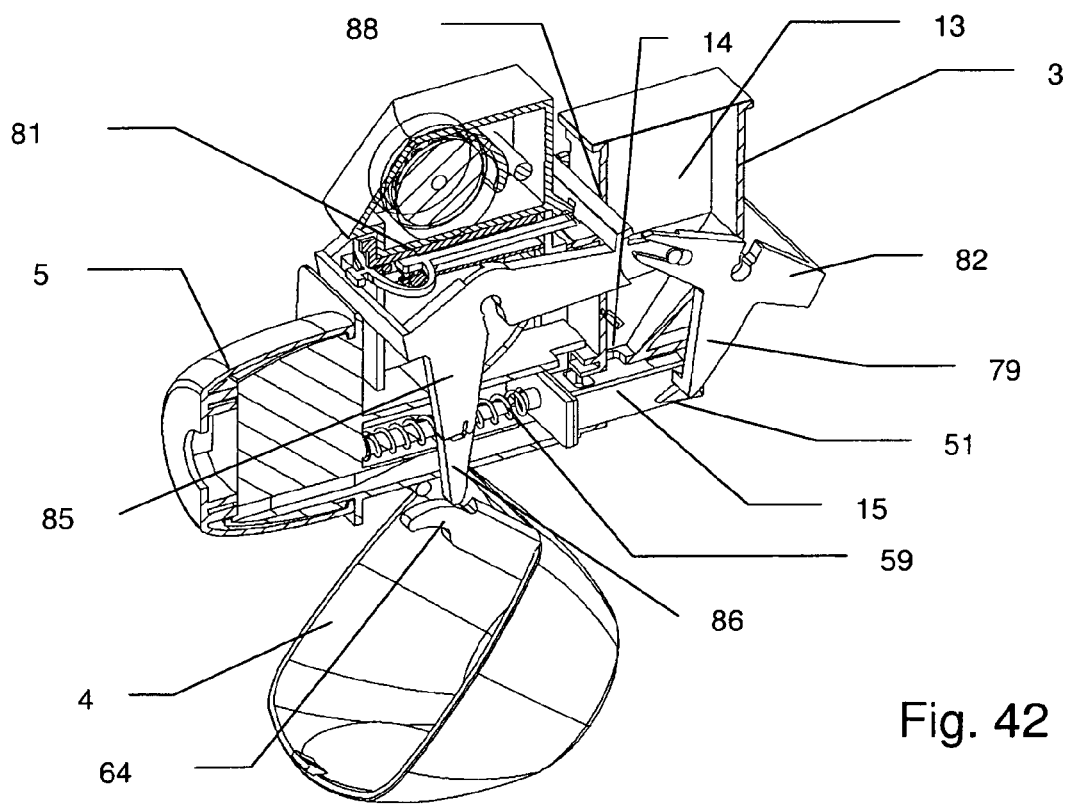
Figure 43:
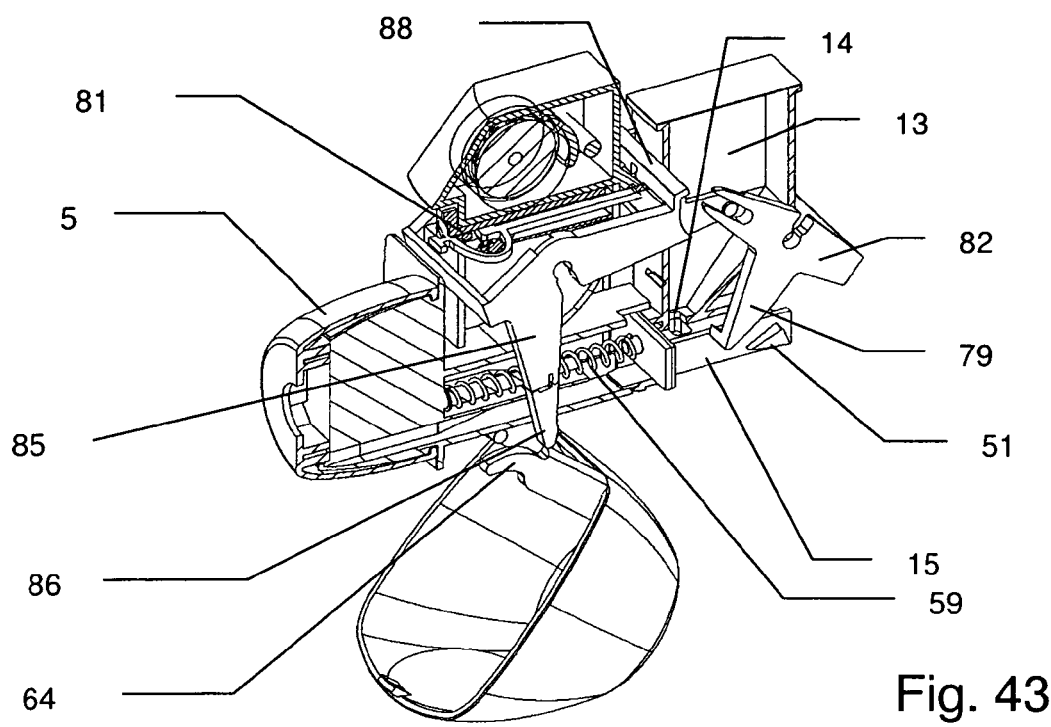

After the emptying position of the dosing slider 15 is reached further pivotal movement of the drive rocker 82 and the transmission rocker 85 provides that the arms 79 of the drive rocker 82 come out of engagement with the entrainment projections 51 of the dosing slider 15 and the dosing slider 15 is pushed back into its filling position by the force of the return spring 59 and thus sealing integrity of the cartridge 3 is ensured again (FIGS. 42 and 43). Hermetic sealing integrity of the cartridge 3 and in particular the storage chamber 13 is therefore interrupted only for fractions of a second, namely the period of time required for the dosing slider 15 to be conveyed out of the filling position into the emptying position and back again. That period of time is only determined by the configuration of the device and cannot be influenced by the user.

Figure 44:
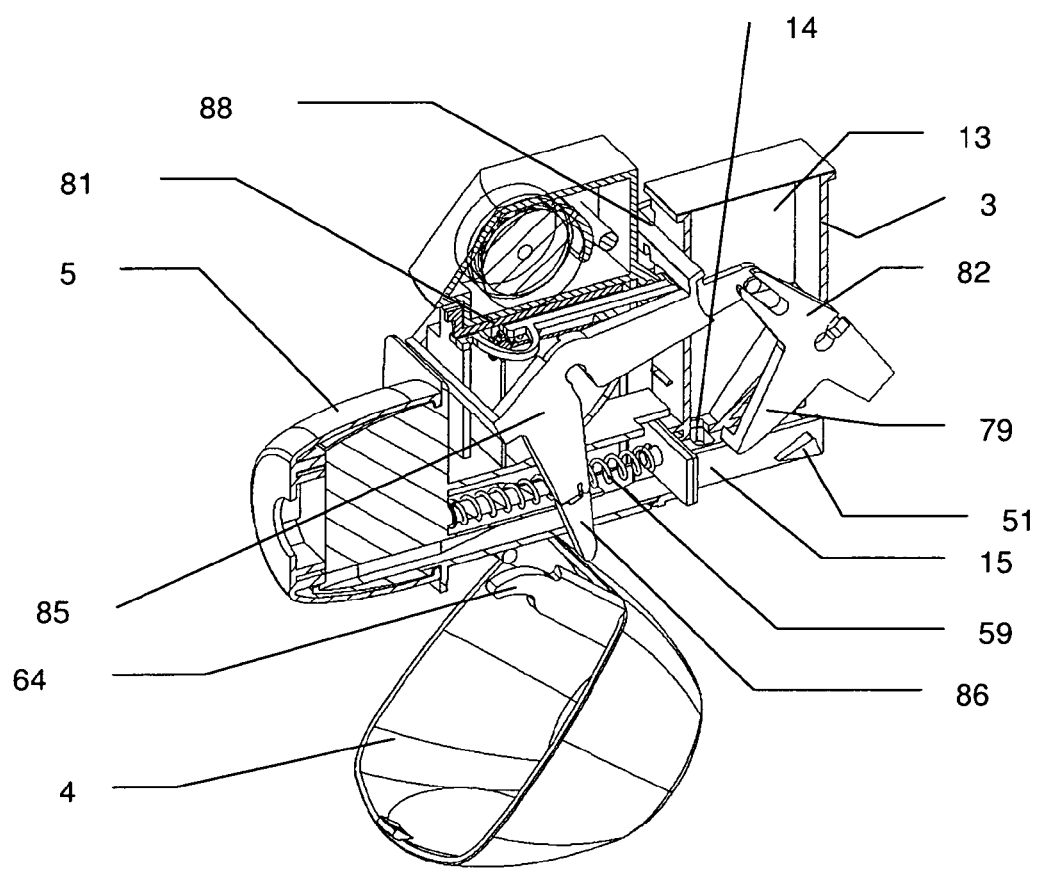
Figure 45:
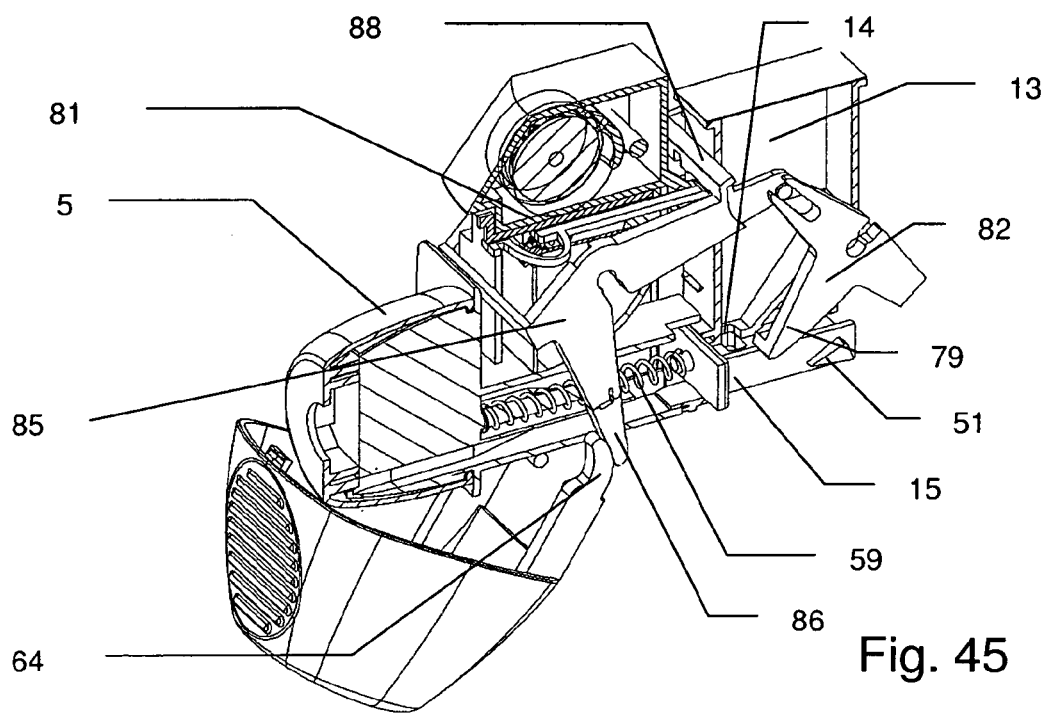
Figure 46:
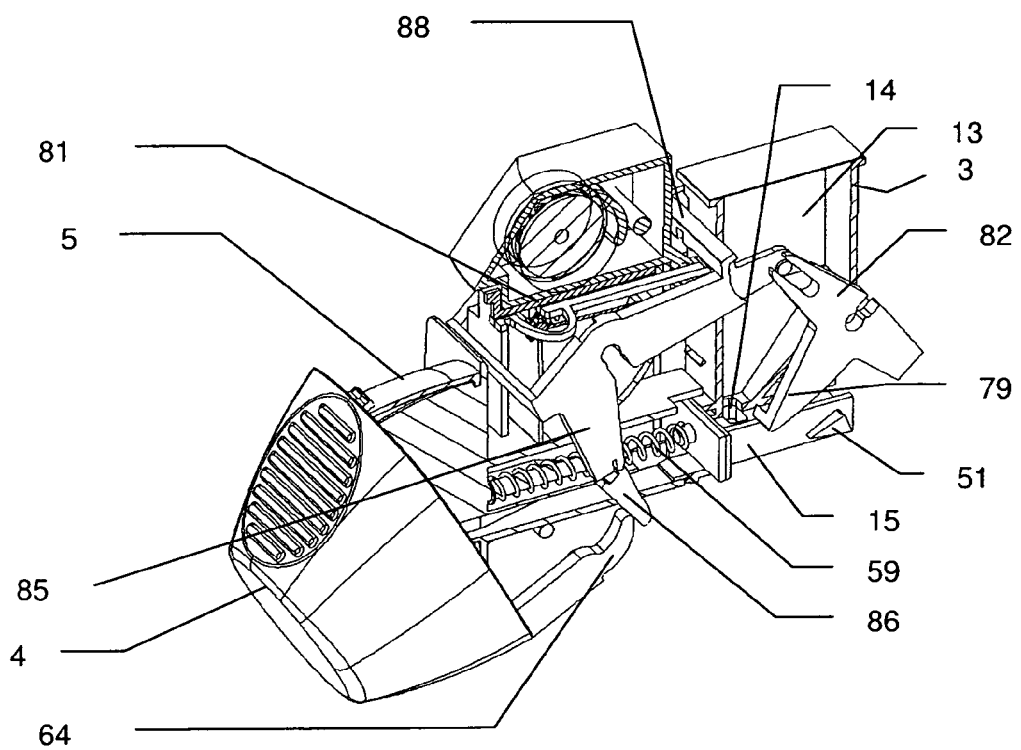
Figure 47:
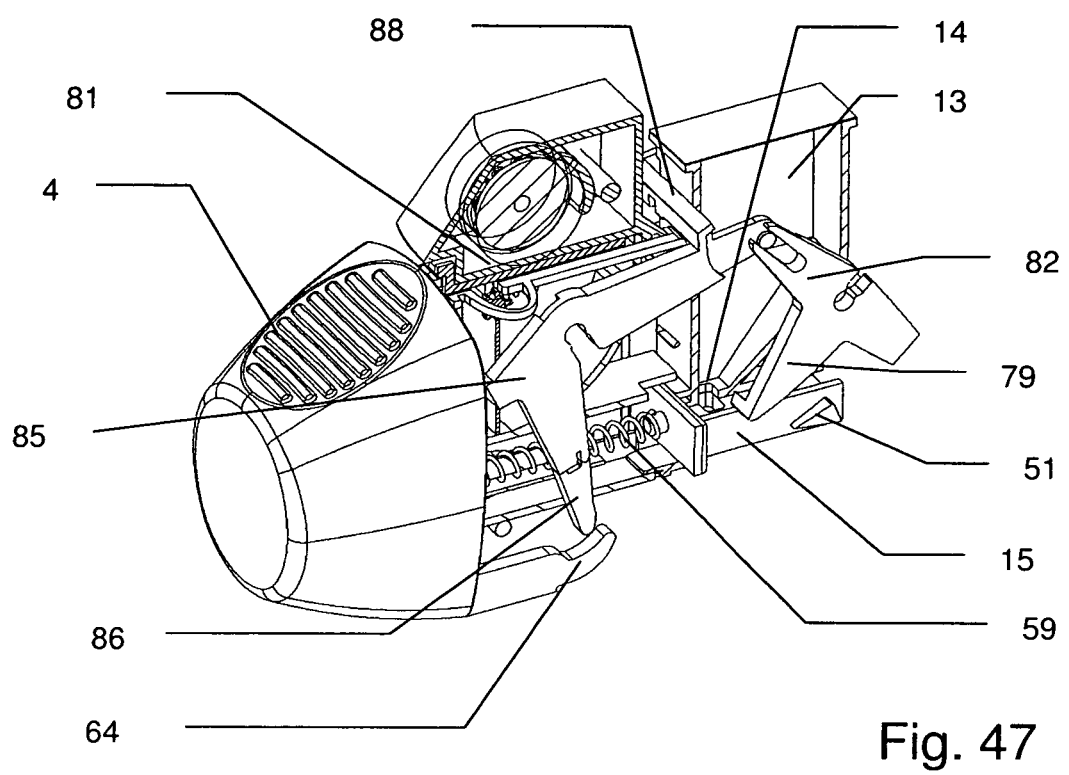

The patient can now pivot the closure cap 4 back into the closure position again (FIG. 44). In that case the entrainment portions 64 of the closure cap 4 knock against the operative ends 86 of the transmission rocker 85 (FIG. 45). In that case the operative ends 86 move away from the entrainment portions 64 by virtue of pivoting by way of the film hinges 87 (FIG. 46) and pivoting back into their starting position again after passing the entrainment portions 64 (FIG. 47) as soon as the closure cap 4 is closed so that it is engaged by the entrainment portions 64 again in the next activation. That arrangement also ensures that the closure cap 4 can be opened and closed again even when the dosing mechanism is in a stressed condition with the transmission rocker 85 and the drive rocker 82 in the readiness position.

The embodiment of an inhalation device according to the present invention shown in FIGS. 19-21, 28-31 and 48 to 55 is particularly useful in a number of medical applications if the at least one storage chamber 13 is provided by a cartridge holder device 100 and a lid 101, wherein the lid 101 has a shape capable of receiving the drug powder content of the storage chamber 13 in an upside-down position of the inhalation device 1. That allows pre-mounting of the cartridge holder 100 and the dosing slider 13 during manufacture of the inhalation device including testing. The lid 101 may serve as an open-top cartridge and filled with the appropriate amount of drug powder in the pharmaceutical manufacturing line, and directly inserted into the inhalation device 1 held upside down. So the inhalation device can be delivered ready to use from the medicament manufacturer. The lid 101 is sealingly fixed onto the cartridge holder by snap connectors 102.

As can be seen from FIGS. 19-21, 28-31 and 48 to 55 the cartridge holder device 100 comprises two storage chambers each covered by a lid 101, wherein the cartridge holder device 100 comprises a twin dosing slider 15. This allows easy and accurate dosing from two different drug reservoirs 13, for instance for the combination of medicaments which may not be stored together to avoid degradation. Further, with the embodiment shown in FIGS. 19-21, 28-31 and 48 to 55, the cartridge holder device 100 comprises two storage chambers 13 each covered by a lid 101, wherein the cartridge holder device 100 comprises a twin dosing slider 15.

Figure 19:
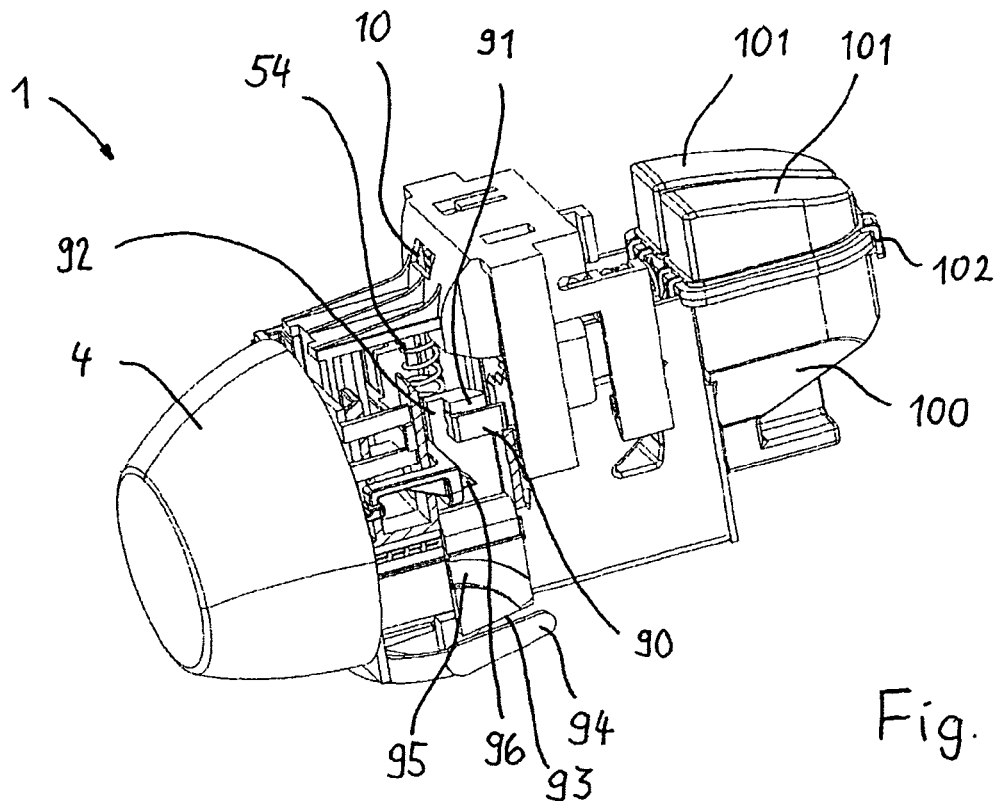
FIG. 19 shows a perspective view of another embodiment of an inhalation device according to the invention with the closure cap in the closure position with the housing removed, with further components being partially omitted to increase legibility.
Figure 20:
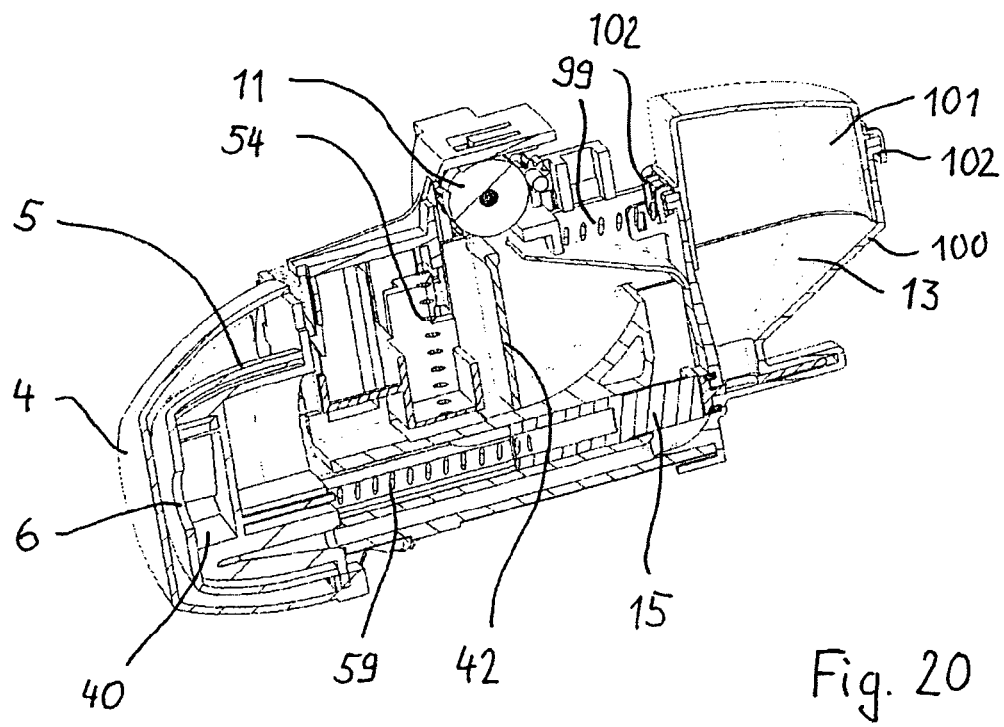
FIG. 20 shows a sectional view of the inhalation device of FIG. 19.

In the inhalation device 1 the trigger device 43 has an engagement portion 90 interacting with a stepped stop element 91 of the drive element 53, 82, wherein the stepped stop element 91 has a first step 97 and the drive element is arrested in an intermediate position when the engagement portion 90 of the trigger device 43 interacts with the first step 97. In this state, dosing of the medicament will take place. The stepped stop element 91 has a second step 98 and the drive element 53, 82 is held in its rest position when the engagement portion 90 of the trigger 43 device interacts with the second step 98. In this state the closure cap 4 is closed, the drive element 53, 82 is in rest position and the flap 42 closed, as shown in FIGS. 19 and 20.

Figure 28:
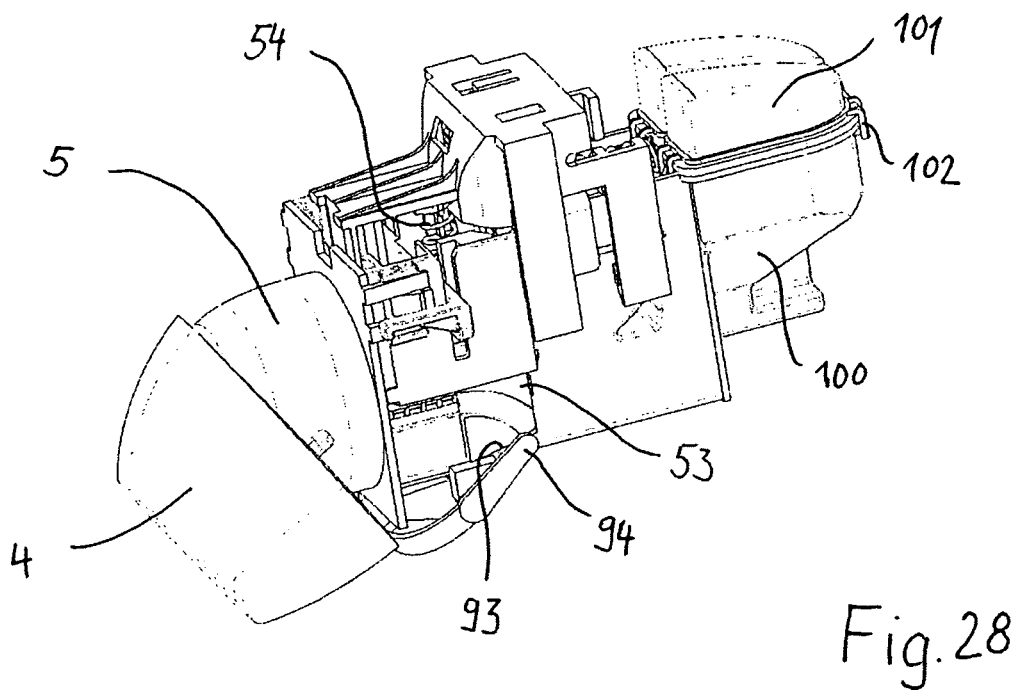
FIGS. 28 and 29 show a perspective view of the embodiment of an inhalation device of FIG. 19 according to the invention with the closure cap slightly opened with the housing removed.
Figure 29:
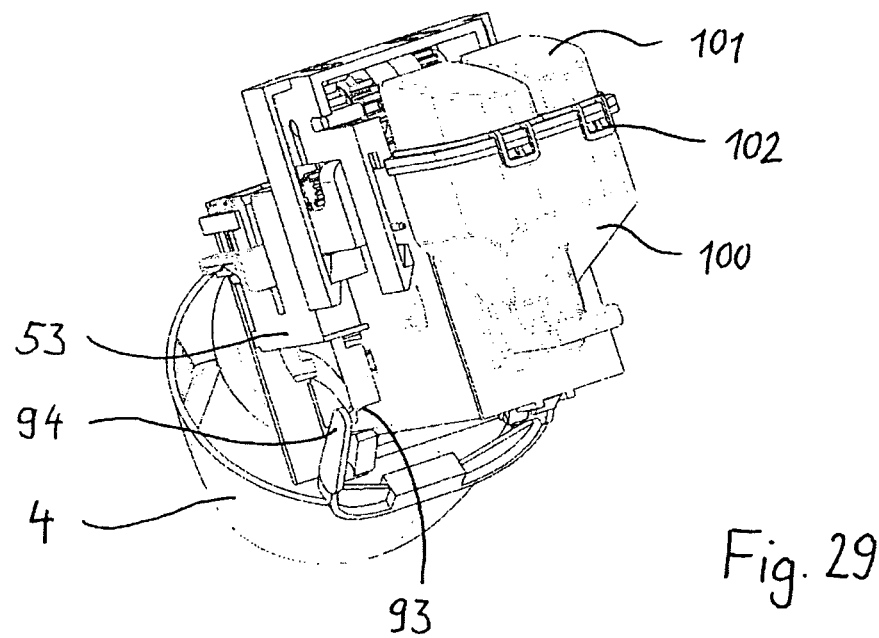

When starting from the rest position of the drive element 53, 82 the closure cap 4 will be opened, the cap 4 rotates about axis 84. The entrainment portion 94 of the cap 4 engages with the sliding guide 93 formed at the bottom edge of the drive element 53, 82, thus, moving the drive element 53, 82 upwardly against the force of biasing spring 54, as shown in FIGS. 28 and 29.

Figure 30:
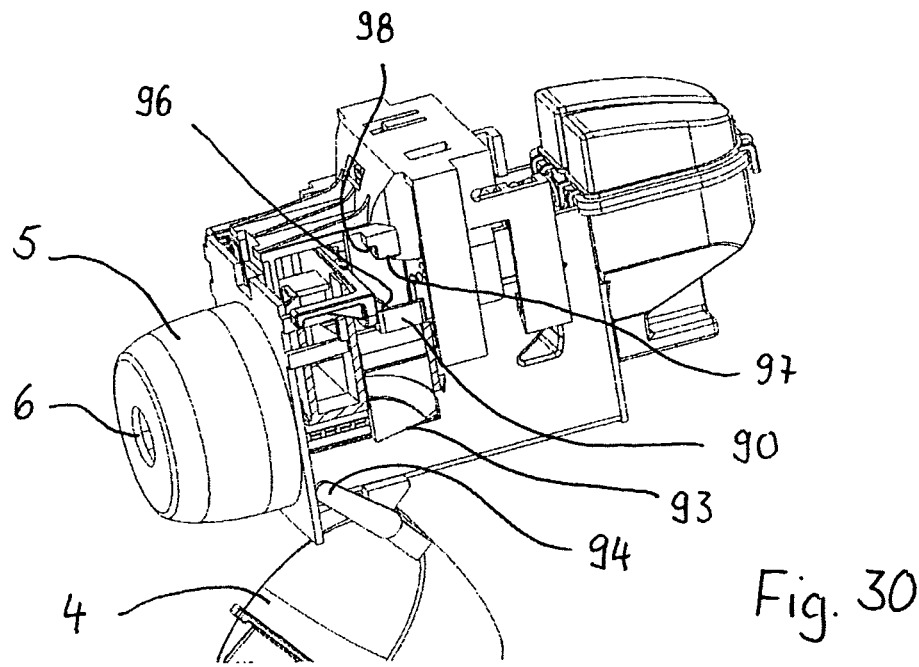
FIG. 30 shows a perspective view of the embodiment of an inhalation device of FIG. 19 according to the invention with the closure cap fully opened, with the housing removed.
Figure 31:
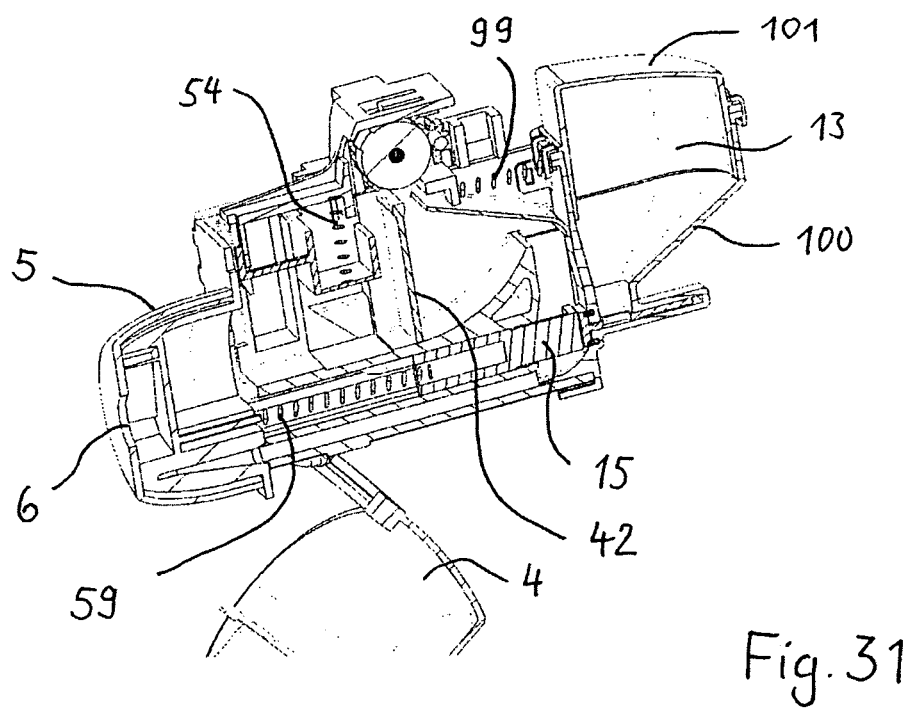
FIG. 31 shows a sectional view of the inhalation device of FIG. 30, FIGS. 32 to 36 show diagrammatic views illustrating the principle of alternative arrangements for the actuation of the sliding guide carrier.

When the operative position of the closure cap 4 is reached as shown in FIGS. 30 and 31, the dosing mechanism is tensioned and the drive element 53 is secured by the engagement portion 90 of the trigger device 43 interacting with projection 96 of the drive element 53. The flap 42 is closed. In this position it is possible to close and re-open the closure cap 4 without adverse effects. The inhalation device is now ready for inhaling.

Figure 48:
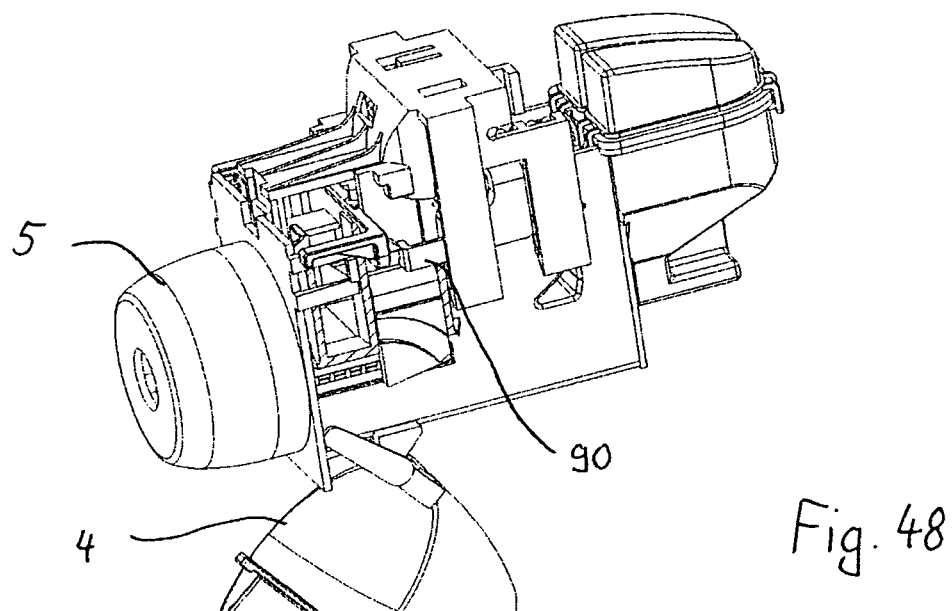
FIGS. 48 to 54 show the inhalation device from FIGS. 19-21 and 28-31 in various operating conditions in a usual use procedure.
Figure 49:
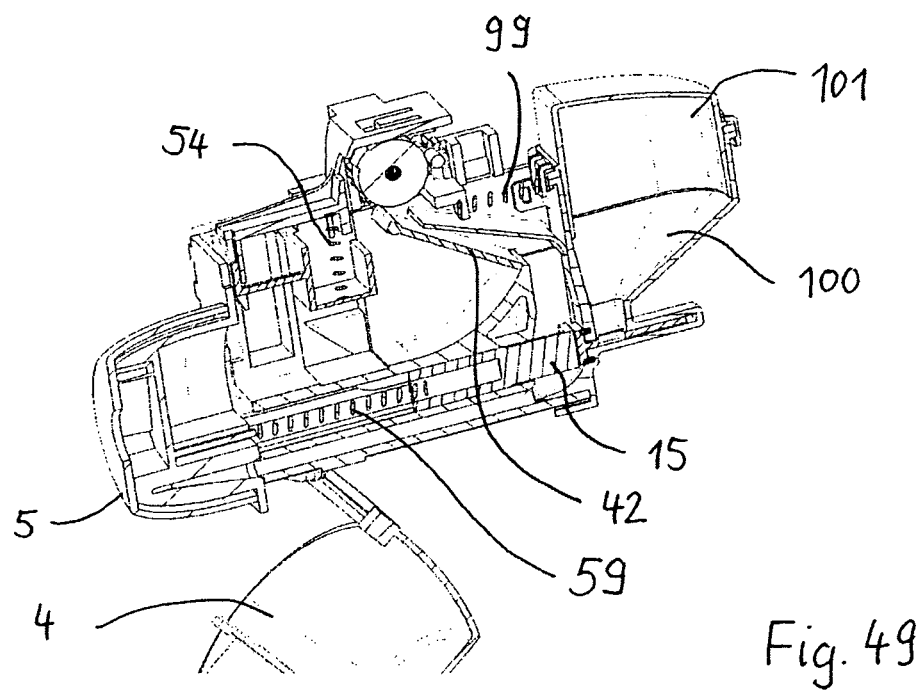
Figure 50:
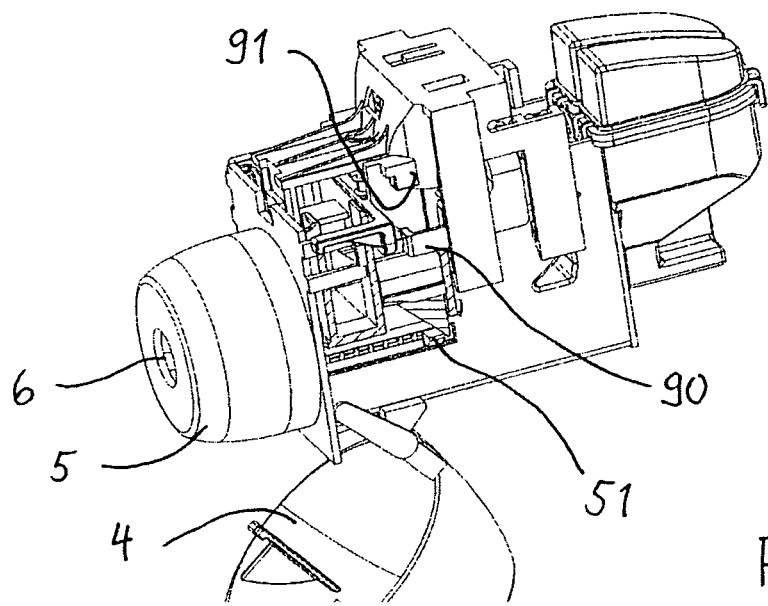
Figure 51:
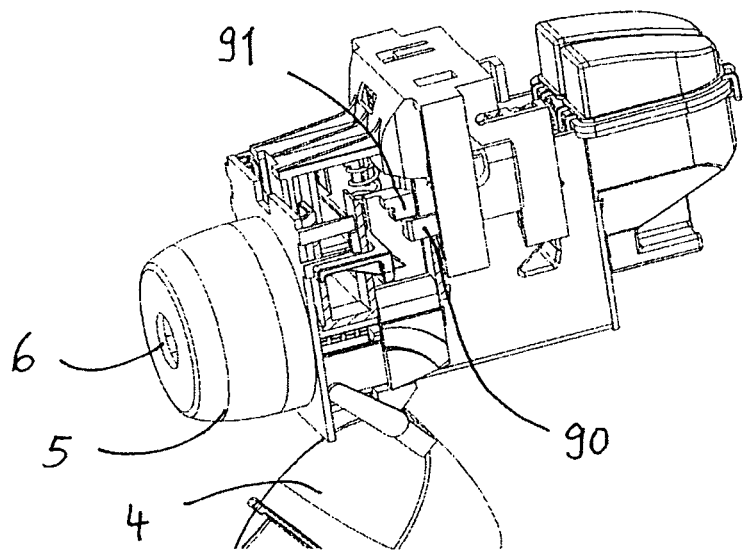
Figure 52:
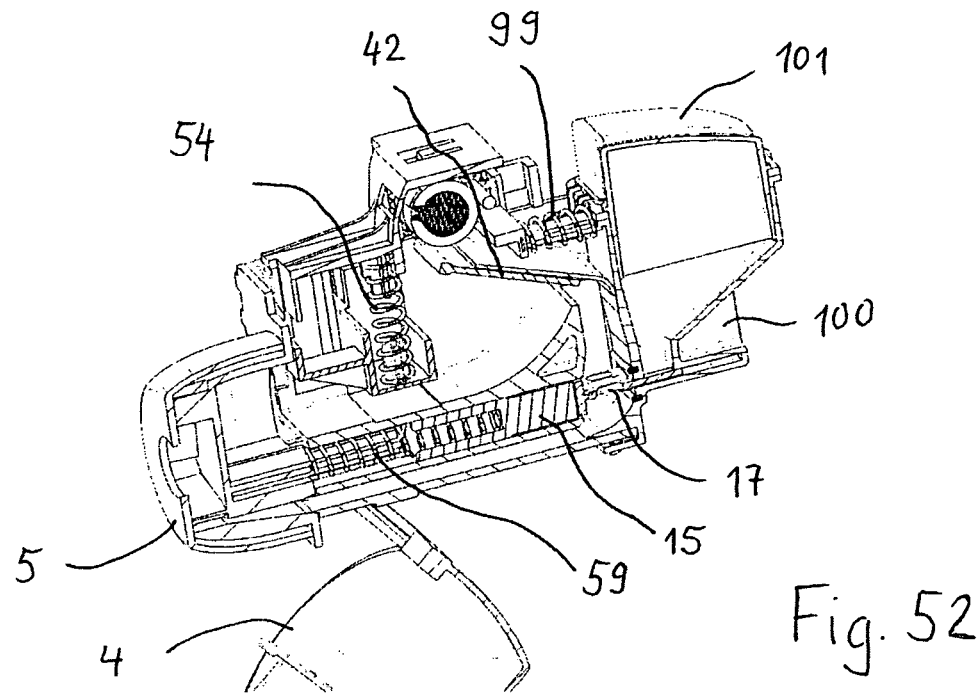

When a patient starts inhaling through the mouthpiece 5, the flap 42 starts to pivot about a pivot axis 80 against the force of spring 99 thereby retracting engagement portion 90 of the trigger device 43 interacting with projection 96 of the drive element 53, see FIGS. 48 and 49.

On release of the drive element 53 from engagement portion 90 of the trigger device 43 interacting with projection 96 drive element 53 starts travelling downwards, thereby engaging entrainment projections 51 of the dosing slider 15 for movement of the dosing slider 15. Those entrainment projections 51 of the dosing slider 15 co-operate with corresponding recesses of an actuating device 53 for the dosing slider in the inhaler, see FIG. 50. So, the dosing slider 15 will be retracted from the dosing slider channel 16 until the slider 15 reaches its emptying position, FIG. 51. At the same time engagement portion 90 of the trigger device 43 engages with the first step 97. As long as the flap 42 keeps fully open due to inhaling, the drive element 53 is arrested in an intermediate position when the engagement portion 90 of the trigger device 43 interacts with the first step 97, thus keeping the dosing slider 15 in its emptying position, see FIG. 52.

Figure 53:
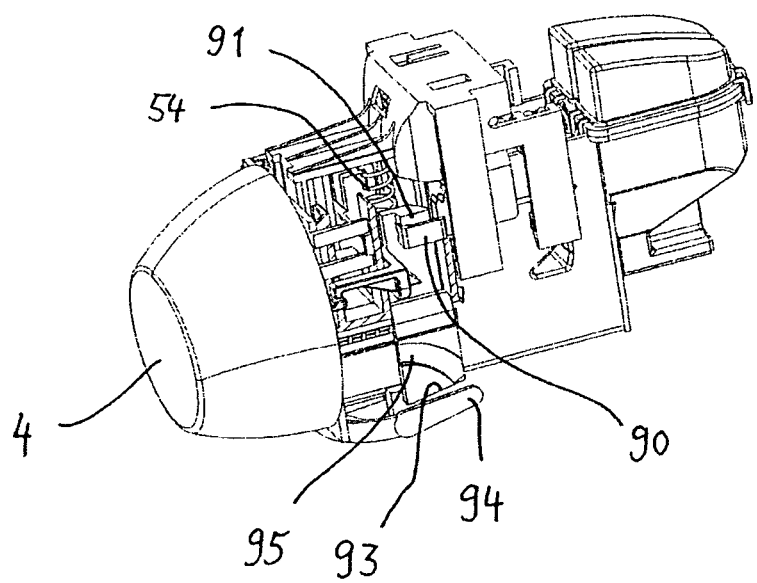

Once the inhalation process is completed and the flap 42 returned to its initial position, second step 98 and the drive element 53, 82 is held in its rest position when the engagement portion 90 of the trigger 43 device interacts with the second step 98. In this state the closure cap 4 may be closed, and the cycle completed, as shown in FIG. 53 compared to FIGS. 19 and 20 at the beginning.

Figure 54:
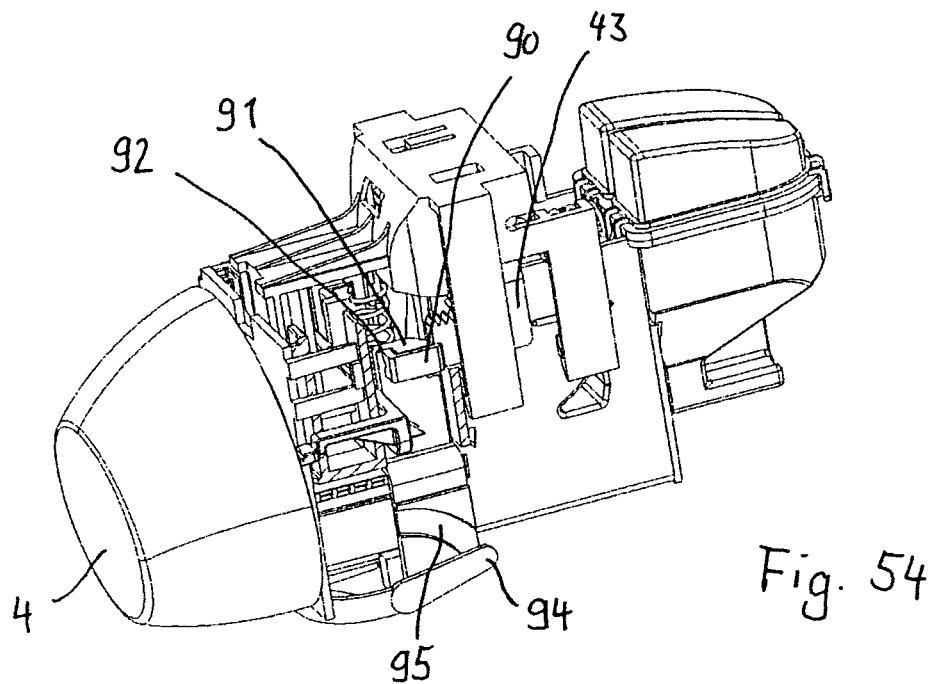

The counting device 11 is connected to the engagement portion 90 of the trigger device 43 and the stepped stop element 91 of the drive element 53, 82 has an opening or recess 92, and the drive element 53, 82 is urged by the biasing spring 54 to a blocking position as shown in FIG. 54, when the engagement portion 90 engages with the opening or recess 92, once removal of a predetermined number of doses has been removed from the inhalation device 1, thus the storage chamber 13 is considered empty, and the device should no longer be used.

The invention claimed is:

1. An inhalation device for powder drugs comprising:
at least one storage chamber for accommodating a plurality of drug powder doses and a dosing device which includes at least one dosing slider which is movable approximately with a translatory movement in a dosing slider passage at least from a filling position into an emptying position;
a device for inhalation-triggered automatic movement of the dosing slider from its filling position into the emptying position;
a return device for automatic movement of the dosing slider back into the filling position;
said at least one storage chamber has at least one outlet opening through which the powder drug can issue under the influence of the force of gravity and the dosing slider has at least one dosing cavity, wherein the dosing cavity in the filling position is under the outlet opening and the dosing slider is movable out of its filling position into the emptying position approximately transversely with respect to the outflow direction of the drug powder from the outlet opening of the at least one storage chamber;
a mouthpiece having an inhalation opening and an air passage which is in flow communication with the mouthpiece and through which a patient can suck an airflow for inhalation, wherein the dosing cavity in the emptying position of the dosing slider is in the air passage; and
a trigger device arranged in the air passage for signalling when a predetermined minimum airflow in the air passage is exceeded, the trigger device comprising a pivotably mounted, directly or indirectly spring-loaded flap arranged in the air passage and the air passage in the region of the flap is of a cross-sectional area which is large in relation to the inhalation opening, the flap coupled to a thrust rod which is operatively connected to the device for inhalation-triggered automatic movement of the dosing slider in such a way that the device for inhalation-triggered automatic movement of the dosing slider is held in a biased position by the thrust rod when the flap is in its rest position and the thrust rod releases the device for inhalation-triggered automatic movement of the dosing slider when the flap is deflected out of its rest position at least by a predetermined amount, wherein the coupling between the flap and the thrust rod is formed by way of a toothed ring segment on the flap and a portion on the thrust rod, which is in the form of a rack.

2. An inhalation device according to claim 1 wherein the dosing slider passage with the at least one dosing slider and the storage chamber is sealed off relative to the environment at least in the filling position of the dosing slider.

3. An inhalation device according to claim 1 further comprising a valve device in the air passage in order to substantially close the air passage, wherein the valve device is operatively connected to the trigger device for inhalation-triggered opening of a substantial part of the flow cross-section of the air passage when a predetermined minimum airflow in the air passage is signalled as being exceeded.

4. An inhalation device according to claim 3 wherein the valve device is part of the device for inhalation-triggered automatic movement of the dosing slider.

5. An inhalation device according to claim 1 wherein the flap is pivotable about a pivot axis and the pivot axis extends through or close to the centre of gravity of the flap.

6. An inhalation device according to claim 1 wherein the flap is pivotable about an axis and has a claw which is pivotable together with the flap about the axis and which holds a spring-loaded securing element and the contact face of which, with the securing element, is formed by a sliding or rolling pairing, wherein the securing element is operatively connected to the device for inhalation-triggered automatic movement of the dosing slider in such a way that the device for inhalation-triggered automatic movement of the dosing slider is held in a biased position by the securing element when the flap is in its rest position and the securing element releases the device for inhalation-triggered automatic movement of the dosing slider when the flap is deflected out of its rest position by at least a predetermined amount.

7. An inhalation device according to claim 1 wherein the trigger device has a piston connected to the air passage and the air passage in the region of the piston has a cross-section which is large in relation to the inhalation opening, wherein the piston is coupled to a thrust rod which is operatively connected to the device for inhalation-triggered automatic movement of the dosing slider in such a way that the device for inhalation-triggered automatic movement of the dosing slider is held in a biased position by the thrust rod when the piston is in its rest position and the thrust rod releases the device for inhalation-triggered automatic movement of the dosing slider when the piston is deflected out of its rest position by at least a predetermined amount by a predetermined minimum airflow in the air passage, which is initiated by a user of the inhalation device.

8. An inhalation device according to claim 1 wherein the device for inhalation-triggered automatic movement of the dosing slider out of its filling position into the emptying position has a drive element which can be moved into a readiness position against the force of a biasing spring and which has at least one sliding guide, an entrainment portion or a cam portion which is operatively connected to the dosing slider in its filling position and is releasably arrested in its readiness position by a trigger device, wherein the sliding guide, the entrainment portion or the cam portion is so designed that the drive element upon a movement out of the readiness position into a rest position moves the dosing slider at least into the emptying position thereof by way of entrainment portions.

9. An inhalation device according to claim 8 wherein the trigger device has an engagement portion interacting with a stepped stop element of the drive element, wherein the stepped stop element has a first step and the drive element is arrested in an intermediate position when the engagement portion of the trigger device interacts with the first step, and a second step and the drive element is held in its rest position when the engagement portion of the trigger device interacts with the second step.

10. An inhalation device according to claim 9 wherein the dosing slide is held in the emptying position by entrainment portions of the drive element and the dosing slide, respectively, in the intermediate position of the drive element.

11. An inhalation device according to claim 9 wherein there is further provided a counting device for detecting the number of delivered drug doses, wherein the counting device individually detects each dosing operation and is connected to a locking device which blocks the closure cap upon the attainment of a predetermined number of delivered doses so that the closure cap is no longer movable into the closure position.

12. An inhalation device according to claim 11 wherein the counting device is connected to the engagement portion of the trigger device and that the stepped stop element of the drive element has an opening or recess, and the drive element is urged by the biasing spring to a blocking position, when the engagement portion engages with the opening or recess.

13. An inhalation device according to claim 12 wherein the drive element in its blocking position engages blockingly into the path of the closure cap so that the closure cap can no longer be moved into the closure position.

14. An inhalation device according to claim 11 wherein the counting device includes a dose-accurate display.

15. An inhalation device according to claim 11 wherein the locking device has a spring-loaded locking element which engages into a groove which is opened at a predetermined number of doses and in that case blockingly engages into a sliding guide of the mechanism of the closure cap so that the closure cap can no longer be moved into the closure position.

16. An inhalation device according to claim 15 wherein the locking element of the locking device is coupled to a signal plate which is displayed upon blocking engagement of the locking device.

17. An inhalation device according to claim 11 wherein the locking device has a spring-loaded blocking rod which is movable from a rest position into a blocking position upon the attainment of a predetermined number of delivered doses and in its blocking position engages blockingly into the path of the closure cap so that the closure cap can no longer be moved into the closure position.

18. An inhalation device according to claim 8, further comprising a return device for automatic movement of the dosing slider back into the filling position, the return device including a return spring.

19. An inhalation device according to claim 18 wherein the dosing slider is connected to the return spring and the sliding guide, the entrainment portion or the cam portion is also so designed that in the rest position of the drive element the dosing slider can return into the filling position due to the force of the return spring.

20. An inhalation device according to claim 18 wherein the drive element in its rest position is out of engagement with the dosing slider.

21. An inhalation device according to claim 8 wherein the drive element is formed by a linearly movable sliding guide carrier.

22. An inhalation device according to claim 8 further comprising a return device for automatically moving the dosing slider back into the filling position, wherein the return device includes a further sliding guide portion.

23. An inhalation device according to claim 8 wherein the sliding guide or the cam portion is of a rectilinear configuration.

24. An inhalation device according to claim 8 wherein the sliding guide or the cam portion is of a curved configuration, in particular of an eccentrically curved configuration or of a helical configuration.

25. An inhalation device according to claim 8 wherein the drive element is formed by a drive rocker pivotable about a first pivot axis.

26. An inhalation device according to claim 25 further comprising a closure cap for the mouthpiece, wherein the closure cap is non-closably connected to the inhalation device and is movable from a closure position in which the closure cap covers the mouthpiece into an operative position in which the mouthpiece is accessible to a patient; and wherein the closure cap has at least one entrainment portion and a transmission rocker which is operatively connected to the driver rocker and which is pivotable about a second pivot axis and the closure cap is pivotable out of the closure position into the operative position about a third axis, wherein the at least one entrainment portion of the closure cap co-operates with at least one operative end of the transmission rocker in such a way that the drive rocker is movable out of its rest position into its readiness position by the movement of the closure cap about the third axis out of the closure position into the operative position by way of the transmission rocker against the force of the biasing spring.

27. An inhalation device according to claim 26 wherein the drive rocker and the transmission rocker are in mutual engagement in such a way that their rotation takes place in opposite relationship about the first and second pivot axes.

28. An inhalation device according to claim 27 wherein the moment of inertia of the drive rocker about the first pivot axis and the moment of inertia of the transmission rocker about the second pivot axis are approximately equal.

29. An inhalation device according to claim 26 wherein the at least one operative end of the transmission rocker is of such a configuration that the operative end is connected in positively locking relationship by the at least one entrainment portion of the closure cap upon movement of the closure cap out of the closure position into the operative position about the third axis and transmits the moment applied by the at least one entrainment portion to the transmission rocker and elastically evades the entrainment portion upon movement of the closure cap out of the operative position into the closure position.

30. An inhalation device according to claim 26 wherein the transmission rocker has two rocker elements which are arranged on both longitudinal sides of the inhalation device pivotably about the second pivot axis and are connected together with at least one yoke, wherein the thrust rod holds the transmission rocker in the biased position of the drive rocker by engagement with the yoke when the flap is in its rest position and the thrust rod enables the travel movement of the yoke when the flap is deflected out of its rest position at least by a predetermined amount so that the transmission rocker and the drive rocker are movable by the biasing spring out of their readiness position into their rest position.

31. An inhalation device according to claim 8 wherein the biasing spring and/or the return spring is a spring selected from a group of springs consisting of a coil spring, a spiral spring, a torsion spring, an elastically deformable shaped body and a compressed air storage means, wherein preferably the biasing spring has a non-linear characteristic.

32. An inhalation device according to claim 8 further comprising a rotary knob which is operatively connected to the drive element and which has an operating handle, wherein the drive element can be moved into its readiness position against the force of the biasing spring by a user with the rotary knob.

33. An inhalation device according to claim 8 further comprising an actuating button operatively connected to the drive element, wherein the drive element can be moved into its readiness position against the force of the biasing spring with the actuating button by a user.

34. An inhalation device according to claim 1 further comprising a closure cap for the mouthpiece, wherein the closure cap is non-closably connected to the inhalation device and is movable from a closure position in which the closure cap covers the mouthpiece into an operative position in which the mouthpiece is accessible to a patient.

35. An inhalation device according to claim 34 wherein the device for inhalation-triggered automatic movement of the dosing slider out of its filling position into the emptying position has a drive element which can be moved into a readiness position against the force of a biasing spring and which has at least one sliding guide, an entrainment portion or a cam portion which is operatively connected to the dosing slider in its filling position and is releasably arrested in its readiness position by a trigger device, wherein the sliding guide, the entrainment portion or the cam portion is so designed that the drive element upon a movement out of the readiness position into a rest position moves the dosing slider at least into the emptying position thereof by way of entrainment portions;
  wherein the drive element is formed by a linearly movable sliding guide carrier; and
  wherein the closure cap or the sliding guide carrier has one or more entrainment portions and the closure cap is movable out of the closure position and is pivotable into the operative position, wherein the closure cap or the sliding guide carrier has a sliding guide complementary to the entrainment portion or portions in such a way that the sliding guide carrier is movable by the movement of the closure cap out of the closure position into the operative position against the force of the biasing spring from its rest position into its readiness position.

36. An inhalation device according to claim 35 wherein the complementary sliding guide has a track for the entrainment portion or portions so that the closure cap is also movable in the readiness position of the sliding guide into the closure position.

37. An inhalation device according to claim 36 wherein the track is such that the sliding guide carrier is fixed in its readiness position by entrainment portions of the closure cap independently of the trigger device when the closure cap is in its closure position.

38. An inhalation device according to claim 35 wherein the complementary sliding guide is inclined with respect to the guide at an angle $\alpha$ of between 15° and 45°.

39. An inhalation device according to claim 35 wherein the complementary sliding guide extends non-rectilinearly.

40. An inhalation device according to claim 35 wherein the closure cap has at least one entrainment portion and the closure cap is movable out of the closure position along a guide substantially rectilinearly into an intermediate position and is pivotable out of the intermediate position into the operative position, wherein the inhalation device further has an eccentric disc operatively connected to the sliding guide carrier so that the eccentric disc is rotated by the entrainment portion of the closure cap upon the rectilinear movement thereof about a fixing axis in such a way that the sliding guide carrier is movable from its rest position into its readiness position by the movement of the closure cap out of the closure position into the intermediate position by way of the eccentric disc against the force of the biasing spring.

41. An inhalation device according to claim 35 wherein the closure cap has a pressure lever and the closure cap is pivotable out of the closure position into the operative position, wherein the pressure lever of the closure cap is pivotable about an axis in such a way that the sliding guide carrier is movable from its rest position into its readiness position by the movement of the closure cap out of the closure position into the operative position by way of the pressure lever against the force of the biasing spring.

42. An inhalation device according to claim 1 wherein the at least one storage chamber has at least one outlet opening through which the powder drug can issue under the influence of the force of gravity, and a filling opening which is disposed substantially in opposite relationship to the outlet opening, wherein the filling opening is sealingly closed.

43. An inhalation device according to claim 42 wherein the filling opening is closed with an aluminum blister film and sealed with a LDPE layer.

44. An inhalation device according to claim 1 wherein the dosing slider passage has at its one end towards the environment an opening through which a part of the dosing slider can pass and a contact surface for a seal is provided around the opening, wherein the dosing slider has a sealing surface which is provided in a plane approximately in transverse relationship with its direction of movement out of the filling position into the emptying position.

45. An inhalation device according to claim 44 wherein an elastic seal is provided on the dosing slider and/or the contact surface, wherein the elastic seal is formed by injection on the dosing slider passage and/or the dosing slider.

46. An inhalation device according to claim 45 wherein the elastic seal can be formed by a sealing rib on the dosing slider passage and/or the dosing slider, which is sealingly deformable by a biasing force which holds the dosing slider in the dosing slider passage.

47. An inhalation device according to claim 1 wherein the inhalation device further has a display for signalling inhalation readiness and/or successful delivery of the medicament.

48. An inhalation device according to claim 1 further comprising a breaking-down device for breaking down agglomerates and the like in the drug powder in flow communication with the mouthpiece, wherein the mouthpiece and the breaking-down device are removable for cleaning by the user and the mouthpiece and the breaking-down device are so adapted that they can only be removed or fitted together or are of a one-piece nature.

49. An inhalation device according to claim 1 wherein the at least one storage chamber is provided by a cartridge holder device and a lid, wherein the lid has a shape capable of receiving the drug powder content of the storage chamber in an upside-down position of the inhalation device.

50. An inhalation device according to claim 49 wherein the lid is sealingly fixed onto the cartridge holder by snap connectors.

51. An inhalation device according to claim 49 wherein the cartridge holder device comprises two storage chambers each covered by a lid, wherein the cartridge holder device comprises a twin dosing slider.

\* \* \* \* \*